United States Patent [19]
Müller et al.

[11] Patent Number: 5,521,206
[45] Date of Patent: May 28, 1996

[54] HETEROCYCLICALLY SUBSTITUTED PHENYLACETIC ACID DERIVATIVES AND THEIR USE IN MEDICAMENTS

[75] Inventors: Ulrich Müller; Klaus Mohrs; Jürgen Dressel, all of Wuppertal; Rudolf Hanko, Dusseldorf; Walter Hübsch; Michael Matzke, both of Wuppertal; Ulrich Niewöhner, Wermelskirchen; Siegfried Raddatz, Cologne; Thomas Krämer, Wuppertal; Matthias Müller-Gliemann, Wuppertal; Hans-Peter Belleman, Wuppertal; Martin Beuck, Erkrath; Stanislav Kazda, Wuppertal; Stefan Wohlfeil, Hilden, all of Germany

[73] Assignee: Bayer Aktiengesellschaft, Leverkusen, Germany

[21] Appl. No.: 227,913

[22] Filed: Apr. 15, 1994

Related U.S. Application Data

[63] Continuation of Ser. No. 870,130, Apr. 15, 1992, abandoned.

[30] Foreign Application Priority Data

Apr. 26, 1991 [DE] Germany .......................... 41 13 693.4
Jan. 16, 1992 [DE] Germany .......................... 42 00 954.5

[51] Int. Cl.$^6$ ...................... A61K 31/415; C07D 233/60
[52] U.S. Cl. .................... 514/400; 548/333.5; 548/338.1
[58] Field of Search ............................ 546/278; 548/250, 548/252, 253, 254, 315.1, 316.4, 317.1, 317.5, 318.1, 318.5, 319.1, 319.5, 320.1, 320.5, 321.5, 322.5, 323.1, 324.1, 324.5, 326.1, 331.5, 332.1, 332.5, 333.1, 333.5, 334.5, 335.1, 338.1, 333.5, 338.1; 514/341, 381, 397, 400, 400

[56] References Cited

U.S. PATENT DOCUMENTS 5,183,810  2/1993  Greenlee et al. ........................ 514/63

FOREIGN PATENT DOCUMENTS

| 0284375 | 3/1988 | European Pat. Off. . |
| 0399732 | 5/1990 | European Pat. Off. . |
| 0399731 | 5/1990 | European Pat. Off. . |
| 0407102 | 6/1990 | European Pat. Off. . |
| 9112002 | 8/1991 | WIPO . |

OTHER PUBLICATIONS

Int. J. Peptide Protein Res., vol. 13, 1979, pp. 403–408; "A series of lysyldipeptide derivatives for racemization studies . . . ", N. L. Benoiton et al.

J. Chem. Soc. Perkin Trans., vol. I, 1979, pp. 1706–1707; "A mild and convenient preparation of t-butyl esters . . . ", S. R. Adapa et al.

J. Chem. Soc., Chem. Commun, 1986, pp. 167–168, 1986; "Mono-and bi-metallic catalysed formate-halide . . . ", C. Buchan et al.

Schwartz et al, Physiological Reviews, vol. 70, No. 4, Oct. (1990) "Developmental Mechanisms Underlying Pathology of Arteries", p. 1177.

Prescott et al, "Angiotensin-converting Enzyme Inhibitor versus . . . ", Am. J. of Pathology, vol. 139, No. 6, Dec. 1991, p. 1291 ff.

De la Llera–Moya et al, "Etoposide Treatment Suppresses Atherosclerotic", Arteriosclerosis and Thrombosis 1992, vol. 12, p. 1363 ff.

Medical Research Reviews, vol. 12, No. 2, 149–191 (1992) "The Discovery of DuP 753, a Potent, Orally Active Nonpeptide Angiotension II Receptor Antagonist".

John J. Sheehan, J. Am. Chem. Soc. 95, 1973, pp. 875–879.

Frank E. Frerman, *The Journal of Biological Chemistry*, 1982, pp. 7087–7093.

N. Leo Benoiton, Int. J. Peptide Protein Res. 17, 1981, pp. 197–204.

R. V. Vizgert, Russian Chemical Reviews, Jan. 1963, pp. 1–20.

Russell Ross, "The Smooth Muscle Cell", in *The Journal of Cell Biology*, 1971, pp. 172–186.

Haust, M. D., Reaction Patterns of Intimal Mesenchyme To Injury, and Repair In Atherosclerosis, Adv. Exp. Med. Biol., 43, 35–57 (1974).

*Primary Examiner*—Patricia L. Morris
*Attorney, Agent, or Firm*—Sprung Horn Kramer & Woods

[57] ABSTRACT

The invention relates to phenylacetic acid derivatives of the formula

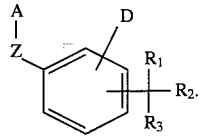

which are substituted by a five-membered nitrogen heterocycle bonded via an N atom. They are prepared by reaction of phenylacetic acid derivatives substituted with leaving groups with the appropriate nitrogen heterocycles and can be used as active substances in medicaments for the treatment of high blood pressure and atherosclerosis.

7 Claims, No Drawings

HETEROCYCLICALLY SUBSTITUTED PHENYLACETIC ACID DERIVATIVES AND THEIR USE IN MEDICAMENTS

This application is a continuation, of application Ser. No. 07/870,130, filed Apr. 15, 1992 now abandoned.

The invention relates to new heterocyclically substituted phenylacetic acid derivatives, processes for their preparation, and their use in medicaments, in particular as hypotensive and anti-atherosclerotic agents.

It is known that renin, a proteolytic enzyme, cleaves the decapeptide angiotensin I, which is in turn degraded in the lungs, the kidneys or other tissues to the hypertensive octapeptide angiotensin II, from angiotensinogen in vivo. The various effects of angiotensin II, such as, for example, vasoconstriction, $Na^+$ retention in the kidneys, aldosterone release in the adrenal gland and increase in tone of the sympathetic nervous system act synergistically in the sense of an increase in blood pressure.

Moreover, angiotensin II has the property of promoting the growth and the replication of cells such as, for example, of heart muscle cells and smooth muscle cells, where these grow at an increased rate and proliferate in various disease states (for example hypertension, atherosclerosis and cardiac insufficiency).

In addition to the inhibition of renin activity, a possible start for intervention in the renin-angiotensin system (RAS) is the inhibition of the activity of angiotensin converting enzyme (ACE) and the blockade of angiotensin II receptors.

Moreover, heterocyclic compounds having A II-antagonistic action are known from the publications EP 407,102, EP 399,731; EP 399,732 and EP 324,347.

The invention relates to heterocyclically substituted phenylacetic acid derivatives of the general formula (I)

in which

A represents a heterocyclic radical, bonded via a nitrogen atom, of the formula in which E, G, L and M are identical or different and denote cycloalkyl having 3 to 8 carbon atoms, hydrogen, tetrazolyl, halogen, perfluoroalkyl having up to 6 carbon atoms or a group of the formula $-OR^4$, $-CO-R^5$, $-C(R^6)=N-NR^7-Q$, $-C(R^8)=C((CH_2)_a-R)((CH_2)_b-T)$, $-CH(R^8)-CH((CH_2)_a-R)((CH_2)_b-T)$, $NR^9R^{10}$ or $-CONH-CH(C_6H_5)-CH_2OH$ in which $R^4$ denotes hydrogen, straight-chain or branched alkyl or acyl having up to 8 carbon atoms or phenyl which is in turn monosubstituted or disubstituted by identical or different halogen, hydroxyl or nitro or by straight-chain or branched alkyl or alkoxy each having up to 8 carbon atoms, or denotes a hydroxyl protective group, denotes hydrogen, hydroxyl or straight-chain or branched alkyl or alkoxy each having up to 8 carbon atoms or a group of the formula $-NR^9R^{10}$ or $-NR^9-SO_2R^{11}$, in which $R^9$ and $R^{10}$ are identical or different and denote hydrogen, straight-chain or branched alkyl or acyl each having up to 8 carbon atoms or phenyl which is optionally substituted by nitro, cyano, halogen, trifluoromethyl or by straight-chain or branched alkyl having up to 6 carbon atoms, $R^{11}$ is straight-chain or branched alkyl having up to 8 carbon atoms, benzyl, 2-phenylvinyl or phenyl which is optionally monosubstituted or disubstituted by identical or different halogen or trifluoromethyl or by straight-chain or branched alkyl or alkoxy each having up to 6 carbon atoms, $R^6$, $R^7$ and $R^8$ are identical or different and denote hydrogen, hydroxyl, acetoxy, straight-chain or branched alkyl having up to 8 carbon atoms or phenyl, Q denotes a group of the formula $-C\equiv N$, $-CO-NR^{12}R^{13}$, $-SO_2-NR^{14}R^{15}$ or $-CO-NR^{16}-SO_2R^{17}$, in which $R^{12}$, $R^{13}$, $R^{14}$, $R^{15}$ and $R^{16}$ are identical or different and have the abovementioned meaning of $R^9$ and $R^{10}$ and are identical to or different from this, $R^{17}$ has the abovementioned meaning of $R^{11}$ and is identical to or different from this, a and b are identical or different and denote a number 0, 1, 2, 3 or 4, R denotes hydrogen or phenyl, thienyl or furyl which are optionally monosubstituted to trisubstituted by identical or different carboxyl, straight-chain or branched alkyl, alkoxy or alkoxycarbonyl each having up to 8 carbon atoms, nitro, hydroxyl, halogen, trifluoromethyl or trifluoromethoxy, T denotes hydrogen or a group of the formula —OR$^{4'}$ or —CO—R$^{5'}$, in which R$^{4'}$ and R$^{5'}$ have the abovementioned meaning of R$^4$ and R$^5$ and are identical to or different from this, or E, G, L and M denote straight-chain or branched alkyl, alkenyl or alkadienyl each having up to 10 carbon atoms which are optionally monosubstituted or disubstituted by halogen or by a 5- to 7-membered, saturated or unsaturated heterocyclic ring having up to 4 heteroatoms from the series comprising N, S and O, by phenyl or cycloalkyl having 3 to 8 carbon atoms or by one of the groups —OR$^{4''}$, —CO—R$^{5''}$, 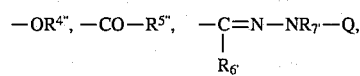

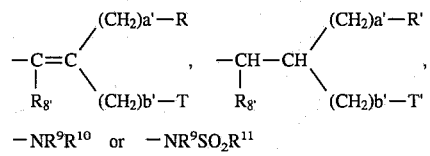

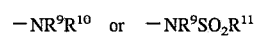

in which

R$^{4''}$, R$^{5''}$, R$^{6'}$, R$^{7'}$, R$^{8'}$, a', b', R' and T' have the abovementioned meaning of R$^4$, R$^5$, R$^6$, R$^7$, R$^8$, a, b, R and T and are identical to or different from this, and R$^9$, R$^{10}$ and R$^{11}$ have the abovementioned meaning or each of E and G, G and L or L and M, together with the heterocycle, form a 5- to 7-membered, saturated, partially unsaturated or aromatic carbocyclic or heterocyclic ring which is fused onto this, the latter optionally having up to 4 heteroatoms from the series comprising N, S and O, where these fused-on rings are optionally monosubstituted to trisubstituted by identical or different halogen or by a group of the formula —V—W or W, in which V denotes a straight-chain or branched alkylene having up to 6 carbon atoms, W denotes hydrogen or a group of the formula —OR$^{4''}$, —CO—R$^{5''}$ or —NR$^{9'}$R$^{10'}$, in which R$^{4''}$ and R$^{5''}$ have the abovementioned meaning, and R$^{9'}$ and R$^{10'}$ have the abovementioned meaning of R$^9$ and R$^{10}$ and are identical to or different from this, Z represents unbranched alkyl, alkenyl or alkynyl each having up to 4 carbon atoms, D represents hydrogen, halogen, nitro, hydroxyl, trifluoromethyl, trifluoromethoxy, straight-chain or branched alkyl, alkoxy or alkoxycarbonyl each having up to 6 carbon atoms, cyano, carboxyl or the group —NR$^9$R$^{10}$, in which R$^9$ and R$^{10}$ have the abovementioned meaning, R$^1$ and R$^2$ are identical or different and represent hydrogen, hydroxyl or straight-chain or branched alkyl having up to 10 carbon atoms, which is optionally substituted by halogen, cycloalkyl having 3 to 8 carbon atoms or phenyl, which can in turn be substituted by halogen, nitro, hydroxyl or by straight-chain or branched alkyl or alkoxy each having up to 8 carbon atoms, represent cycloalkyl or cycloalkenyl having 3 to 12 carbon atoms or phenyl, which are optionally substituted by halogen or by straight-chain or branched alkyl or alkoxy each having up to 6 carbon atoms, or R$^1$ and R$^2$, together with the carbon atom, form a 3- to 7-membered, saturated or unsaturated carbocycle which is optionally monosubstituted or disubstituted by identical or different straight-chain or branched alkyl or alkoxy each having up to 6 carbon atoms, phenyl, hydroxyl or halogen, R$^3$ represents tetrazolyl, or represents a group of the formula —C≡N, —CO—R$^{18}$, —CO—NR$^{19}$R$^{20}$, —CO—NR$^{21}$—SO$_2$—R$^{22}$ or —SO$_2$—NR$^{23}$R$^{24}$, in which R$^{18}$ denotes hydroxyl, straight-chain or branched alkoxy having up to 10 carbon atoms or phenoxy, R$^{19}$ and R$^{20}$ are identical or different, have the abovementioned meaning of R$^9$ and R$^{10}$ and are identical to or different from this, or R$^{19}$ has the abovementioned meaning and R$^{20}$ denotes a group of the formula

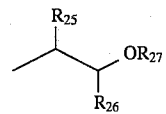

in which

R$^{25}$ and R$^{26}$ are identical or different and denote hydrogen, phenyl, benzyl or a 5- to 7-membered, saturated heterocycle each having up to 3 heteroatoms from the series comprising N, S and O, which can in turn be monosubstituted or disubstituted by halogen, hydroxyl, nitro, cyano, hydroxyl, carboxyl or by straight-chain or branched alkyl, alkoxy or alkoxycarbonyl each having up to 8 carbon atoms, R$^{27}$ denotes hydrogen or straight-chain or branched alkyl or acyl each having up to 8 carbon atoms, R$^{21}$, R$^{23}$ and R$^{24}$ are identical or different and have the abovementioned meaning of R$^9$ and R$^{10}$ and are identical to or different from this, and R$^{22}$ has the abovementioned meaning of R$^{11}$ and is identical to or different from this or denotes a radical of the formula

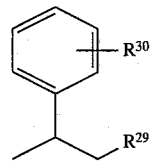

in which

R$^{29}$ denotes hydroxyl, carboxyl or straight-chain or branched alkoxycarbonyl having up to 6 carbon atoms, and R³⁰ denotes hydrogen or halogen, and their salts.

The heterocyclically substituted phenylacetic acid derivatives according to the invention can also be present in the form of their salts. In general, salts with organic or inorganic bases or acids may be mentioned here.

In the context of the present invention, physiologically acceptable salts are preferred. Physiologically acceptable salts of the heterocyclically substituted phenylacetic acid derivatives can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Physiologically acceptable salts can also be metal or ammonium salts of the compounds according to the invention which have a free carboxyl group. Particularly preferred are, for example, sodium, potassium, magnesium or calcium salts, and also ammonium salts which are derived from ammonia, or organic amines such as, for example, ethylamine, di- or triethylamine, di- or triethanolamine, dicyclohexylamine, dimethylaminoethanol, arginine, lysine or ethylenediamine.

The compounds according to the invention can exist in stereoisomeric forms which behave either as image and mirror image (enantiomers) or which do not behave as image and mirror image (diastereomers). The invention relates both to the enantiomers and diastereomers or their respective mixtures. The racemic forms can be resolved into the steroisomerically uniform constituents in a known manner just like the diastereomers [cf. E. L. Eliel, Stereochemistry of Carbon Compounds, McGraw Hill, 1962].

Heterocycle in general represents a 5- to 7-membered, preferably 5- to 6-membered, saturated or unsaturated ring which as heteroatoms can contain up to 2 oxygen, sulphur and/or nitrogen atoms. 5- and 6-membered rings having an oxygen, sulphur and/or up to 2 nitrogen atoms are preferred. The following are mentioned as preferred: thienyl, furyl, pyrrolyl, pyrazolyl, pyridyl, pyrimidyl, pyrazinyl, pyridazinyl, thiazolyl, oxazolyl, imidazolyl, pyrrolidinyl, piperidinyl, piperazinyl or tetrazolyl.

Preferred compounds of the general formula (I) are those in which

A represents a heterocyclic radical, bonded via a nitrogen atom, of the formula

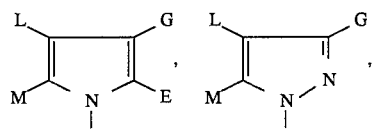,

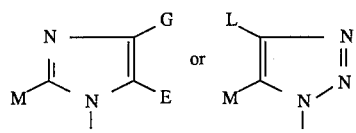

in which

E, G, L and M are identical or different and denote hydrogen, tetrazolyl, cyclopropyl, cyclopentyl, cyclohexyl, fluorine, chlorine, bromine, iodine, perfluoroalkyl having up to 4 carbon atoms or a group of the formula

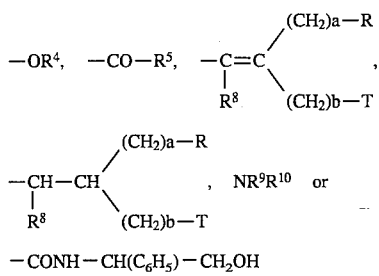

—CONH—CH(C₆H₅)—CH₂OH in which

R⁴ denotes hydrogen, straight-chain or branched alkyl or acyl each having up to 6 carbon atoms or phenyl which is in turn substituted by fluorine, chlorine, bromine, hydroxyl or nitro or by straight-chain or branched alkyl or alkoxy each having up to 6 carbon atoms, or denotes methoxyethoxymethyl, R⁵ denotes hydrogen, hydroxyl or straight-chain or branched alkyl or alkoxy each having up to 6 carbon atoms or a group of the formula —NR⁹R¹⁰ or —NR⁹—SO₂R¹¹, in which R⁹ and R¹⁰ are identical or different and denote hydrogen, straight-chain or branched alkyl or acyl each having up to 6 carbon atoms or phenyl which is optionally substituted by nitro, trifluoromethyl, fluorine, chlorine or bromine or by straight-chain or branched alkyl having up to 4 carbon atoms, R¹¹ denotes straight-chain or branched alkyl having up to 6 carbon atoms, benzyl, 2-phenylvinyl or phenyl which is optionally substituted by fluorine, chlorine, bromine or trifluoromethyl or by straight-chain or branched alkyl or alkoxy each having up to 4 carbon atoms, R⁸ denotes hydrogen, hydroxyl, acetoxy, straight-chain or branched alkyl having up to 6 carbon atoms or phenyl, a and b are identical or different and denote a number 0, 1, 2 or 3, R denotes hydrogen or phenyl, thienyl or furyl which are optionally monosubstituted or disubstituted by identical or different carboxyl, straight-chain or branched alkyl, alkoxy or alkoxycarbonyl each having up to 6 carbon atoms, nitro, hydroxyl, fluorine, chlorine, bromine, trifluoromethyl or trifluoromethoxy, T denotes hydrogen or a group of the formula —OR⁴' or —CO—R⁵', in which R⁴' and R⁵' have the abovementioned meaning of R⁴ and R⁵ and are identical to or different from this, or E, G, L and M denote straight-chain or branched alkyl, alkenyl or alkadienyl each having up to 8 carbon atoms which are optionally monosubstituted or disubstituted by fluorine, bromine, chlorine, phenyl, tetrazolyl, cyclopropyl, cyclopentyl or cyclohexyl or by one of the groups

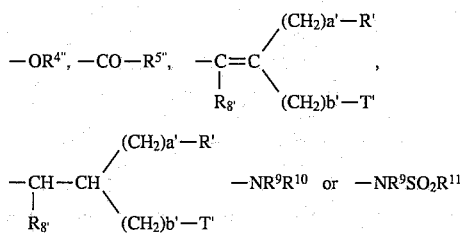
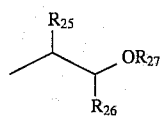

in which
R$^{4''}$, R$^{5''}$, R$^{8'}$, a', b', R' and T' have the abovementioned meaning of R$^4$, R$^5$, R$^8$, a, b, R and T and are identical to or different from this,
and
R$^9$, R$^{10}$ and R$^{11}$ have the abovementioned meaning, or each of E and G, G and L or L and M, together with the heterocycle, form a cyclopentyl, cyclopentenyl, cyclohexyl, cyclohexenyl, phenyl, pyridyl, thienyl or pyrimidinyl ring fused onto this, where these rings are optionally monosubstituted or disubstituted by identical or different fluorine, chlorine or bromine or by a group of the formula —V—W or W,
in which
V denotes straight-chain or branched alkylene having up to 4 carbon atoms,
W denotes hydrogen or a group of the formula —OR$^{4''}$, —CO—R$^{5''}$ or —NR$^{9'}$R$^{10'}$,
in which
R$^{4''}$ and R$^{5''}$ have the abovementioned meaning,
and
R$^{9'}$ and R$^{10'}$ have the abovementioned meaning of R$^9$ and R$^{10}$ and are identical to or different from this, Z represents unbranched alkyl, alkenyl or alkynyl each having up to 3 carbon atoms, D represents hydrogen, fluorine, chlorine, bromine, trifluoromethyl, carboxyl or straight-chain or branched alkyl, alkoxy or alkoxycarbonyl each having up to 4 carbon atoms, R$^1$ and R$^2$ are identical or different and represent hydrogen, hydroxyl or straight-chain or branched alkyl having up to 8 carbon atoms, which is optionally substituted by fluorine, chlorine, bromine, cyclopropyl, cyclopentyl, cyclohexyl or phenyl which can in turn be substituted by fluorine, chlorine or bromine or by straight-chain or branched alkyl or alkoxy each having up to 6 carbon atoms, represent cyclobutyl, cyclopentyl, cyclohexyl, cycloheptyl, cyclooctyl or phenyl which are optionally substituted by fluorine, chlorine or bromine or by straight-chain or branched alkyl or alkoxy each having up to 4 carbon atoms, or R$^1$ and R$^2$ together form a cyclopropyl, cyclopentyl or cyclohexyl ring which is optionally substituted by straight-chain or branched alkyl or alkoxy each having up to 4 carbon atoms, phenyl, fluorine or chlorine, R$^3$ represents tetrazolyl, or
represents a group of the formula —C≡N, —CO—R$^{18}$, —CO—NR$^{19}$R$^{20}$, —CO—NR$^{21}$—SO$_2$R$^{22}$ or —SO$_2$—NR$^{23}$R$^{24}$,
in which
R$^{18}$ denotes hydroxyl, straight-chain or branched alkoxy having up to 8 carbon atoms or phenoxy,
R$^{19}$ and R$^{20}$ are identical or different and have the abovementioned meaning of R$^9$ and R$^{10}$ and are identical to or different from this or
R$^{19}$ has the abovementioned meaning
and
R$^{20}$ denotes a group of the formula

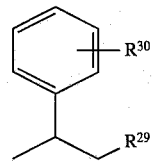

in which
R$^{25}$ and R$^{26}$ are identical or different and denote hydrogen, phenyl, benzyl, pyridyl or thienyl which can in turn be mono- or disubstituted by hydroxyl, carboxyl, fluorine, chlorine or bromine or by straight-chain or branched alkyl, alkoxy or alkoxycarbonyl each having up to 6 carbon atoms,
R$^{27}$ denotes hydrogen or straight-chain or branched alkyl or acyl each having up to 6 carbon atoms,
R$^{21}$, R$^{23}$ and R$^{24}$ are identical or different and have the abovementioned meaning of R$^9$ and R$^{10}$ and are identical to or different from this,
R$^{22}$ has the abovementioned meaning of R$^{11}$ and is identical to or different from this, or denotes a radical of the formula

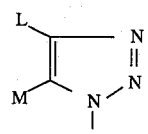

in which
R$^{29}$ denotes hydroxyl, carboxyl or straight-chain or branched alkoxycarbonyl having up to 6 carbon atoms,
and
R$^{30}$ denotes hydrogen, fluorine or chlorine,
and their salts.

Particularly preferred compounds of the general formula (I) are those in which
A represents an imidazole ring, bonded via a nitrogen atom, of the formula

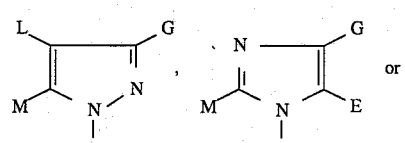

in which
E, G, L and M are identical or different and denote cyclopropyl, hydrogen, tetrazolyl, fluorine, iodine, chlorine, bromine, trifluoromethyl, perfluoroalkyl having up to 4 carbon atoms or a group of the formula —OR$^4$, —CO—R$^5$, 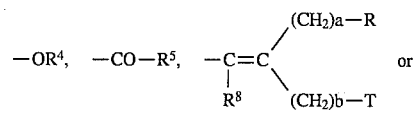 or

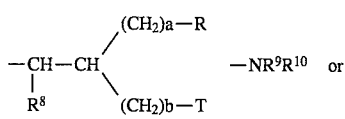 —NR$^9$R$^{10}$ or

—CONH—CH(C$_6$H$_5$)—CH$_2$OH in which
R$^4$ denotes hydrogen, straight-chain or branched alkyl or acyl each having up to 4 carbon atoms or phenyl which is in turn substituted by fluorine or chlorine or by straight-chain or branched alkyl or alkoxy each having up to 4 carbon atoms, or denotes methoxyethoxymethyl, R$^5$ denotes hydrogen, hydroxyl or straight-chain or branched alkyl or alkoxy each having up to 4 carbon atoms or a group of the formula —NR$^9$R$^{10}$ or —NR$^9$—SO$_2$R$^{11}$,
in which
R$^9$ and R$^{10}$ are identical or different and denote hydrogen or straight-chain or branched alkyl or acyl each having up to 4 carbon atoms,
R$^{11}$ denotes straight-chain or branched alkyl having up to 4 carbon atoms, benzyl, 2-phenylvinyl or phenyl which is optionally substituted by fluorine, chlorine, bromine or trifluoromethyl or by methyl or ethyl, R$^8$ denotes hydrogen, hydroxyl, acetoxy or straight-chain or branched alkyl having up to 4 carbon atoms, a and b are identical or different and denote a number 0, 1 or 2, R denotes hydrogen or phenyl, thienyl or furyl which are optionally substituted by carboxyl, straight-chain or branched alkyl, alkoxy or alkoxycarbonyl each having up to 4 carbon atoms, fluorine, chlorine or trifluoromethyl, T denotes hydrogen or a group of the formula —OR$^{4'}$ or —CO—R$^{5'}$,
in which
R$^{4'}$ and R$^{5'}$ have the abovementioned meaning of R$^4$ and R$^5$ and are identical to or different from this, or E, G, L and M denote straight-chain or branched alkyl, alkenyl or alkadienyl each having up to 6 carbon atoms, which are optionally monosubstituted or disubstituted by fluorine, chlorine, bromine, tetrazolyl, cyclohexyl or phenyl or by one of the groups —OR$^{4''}$, —CO—R$^{5''}$, 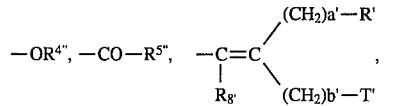,

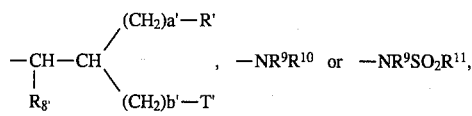, —NR$^9$R$^{10}$ or —NR$^9$SO$_2$R$^{11}$, in which
R$^{4''}$, R$^{5''}$, R$_{8'}$, a', b', R' and T' have the abovementioned meaning of R$^4$, R$^5$, R$^8$, a, b, R and T and are identical to or different from this, and
R$^9$, R$^{10}$ and R$^{11}$ have the abovementioned meaning, or E and G or L and M, together with the heterocycle, form a cyclohexyl, phenyl, thienyl, pyridyl or pyrimidyl ring fused onto this, where these rings are optionally substituted by fluorine, chlorine, bromine or a group of the formula —V—W or W,
in which
V denotes straight-chain or branched alkylene having up to 3 carbon atoms,
W denotes hydrogen or a group of the formula —OR$^{4''}$, —COR$^{5''}$ or —NR$^{9'}$R$^{10'}$,
in which
R$^{4''}$ and R$^{5''}$ have the abovementioned meaning,
R$^{9'}$ and R$^{10'}$ have the abovementioned meaning of R$^9$ and R$^{10}$ and are identical to or different from this, Z represents the —CH$_2$—, —(CH$_2$)$_2$—, —(CH$_2$)$_3$—, —HC=CH— or —C≡C— group, D represents hydrogen, fluorine, chlorine, bromine, trifluoromethyl, trifluoromethoxy or methyl, R$^1$ and R$^2$ are identical or different and represent hydrogen, hydroxyl or straight-chain or branched alkyl having up to 7 carbon atoms, which is optionally substituted by fluorine, chlorine, cyclopropyl, cyclopentyl, cyclohexyl or phenyl which is optionally substituted by fluorine or chlorine or by straight-chain or branched alkyl or alkoxy each having up to 4 carbon atoms, or represent cyclopentyl or cycloheptyl or R$^1$ represents hydrogen
and
R$^2$ represents cyclopentyl, cyclohexyl, cycloheptyl, cyclooctyl or phenyl which are optionally substituted by fluorine or chlorine or by methyl, ethyl or methoxy, or R$^1$ and R$^2$ together form a cyclopropyl, cyclopentyl or cyclohexyl ring which is optionally substituted by methyl, methoxy, phenyl or fluorine, R$^3$ represents tetrazolyl, or
represents a group of the formula —C≡N, —CO—R$^{18}$, —CO—NR$^{19}$R$^{20}$, —CO—NR$^{21}$—SO$_2$R$^{22}$ or —SO$_2$—NR$^{23}$R$^{24}$,
in which
R$^{18}$ denotes hydroxyl, straight-chain or branched alkoxy having up to 6 carbon atoms or phenoxy,
R$^{19}$ and R$^{20}$ are identical or different and have the abovementioned meaning of R$^9$ and R$^{10}$ and are identical to or different from this,
or
R$^{19}$ denotes hydrogen
and
R$^{20}$ denotes a group of the formula

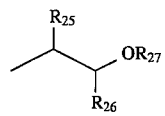

in which
R$^{25}$ and R$^{26}$ are identical or different and denote hydrogen, phenyl or benzyl which can in turn be mon- or disubstituted by hydroxyl, fluorine or chlorine or by straight-chain or branched alkyl having up to 4 carbon atoms, $R^{27}$ denotes hydrogen or straight-chain or branched alkyl or acyl each having up to 4 carbon atoms, $R^{21}$, $R^{23}$ and $R^{24}$ are identical or different and have the abovementioned meaning of $R^9$ and $R^{10}$ and are identical to or different from this, $R^{22}$ has the abovementioned meaning of $R^{11}$ and is identical to or different from this, or denotes a radical of the formula

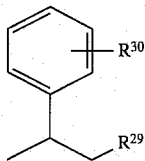

in which
$R^{29}$ denotes hydroxyl, carboxyl, methoxy- or ethoxycarbonyl,
and
$R^{30}$ denotes hydrogen, fluorine or chlorine,
and their salts.

Moreover, a process for the preparation of the compounds of the general formula (I) according to the invention was found, characterised in that compounds of the general formula (II)

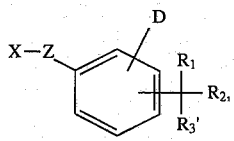

(II)

in which
Z, D, $R^1$ and $R^2$ have the abovementioned meaning,
X represents a typical leaving group such as, for example, chlorine, bromine, iodine, tosylate or mesylate, preferably bromine,
and
$R^{3'}$ represents alkoxycarbonyl having up to 6 carbon atoms or cyano,
are reacted with compounds of the general formula (III)

A—H    (III)

in which
A has the abovementioned meaning, in inert solvents, if appropriate in the presence of a base and if appropriate under a protective gas atmosphere, to give compounds of the general formula (Ia)

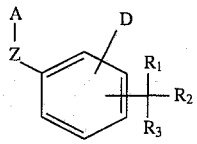

(I)

in which
A, Z, D, $R^1$, $R^2$ and $R^{3'}$ have the abovementioned meaning, in the case of the acids ($R^3$=COOH), the ester or cyano group is hydrolysed by a customary method, in the case of the preparation of the amides and acylsulphonamides ($R^3$=—CO—NR$^{19}$R$^{20}$ or —CO—NR$^{21}$SO$_2$—R$^{22}$), the esters or the acids are either reacted directly after customary activation, if appropriate in the presence of a base, or of an auxiliary, acid-binding agent and/or of a dehydrating agent, with amines or sulphonylamines of the general formulae (IV) or (V)

HNR$^{19}$R$^{20}$    (IV),

HNR$^{21}$SO$_2$R$^{22}$    (V), in which
$R^{19}$, $R^{20}$, $R^{21}$ and $R^{22}$ have the abovementioned meaning,
and in the case that $R^3$ represents the tetrazole ring, the cyano compound (II, $R^{3'}$=CN) is either reacted in the presence of amine hydrochlorides, preferably triethylamine hydrochloride, with sodium azide, or with a tin azide, preferably trimethyltin azide, and, if appropriate, both the substituent D and the substituents E, G, M and L are introduced in any step, preferably by means of the acid step ($R^3$=COOH) by a customary method such as, for example, halogenation, dehydrohalogenation, reduction, oxidation, alkylation or hydrolysis, or converted into other functional groups, if appropriate the isomers are separated, and in the case of the preparation of the salts reacted with an appropriate base or acid.

The process according to the invention can be illustrated by way of example by the following equation:

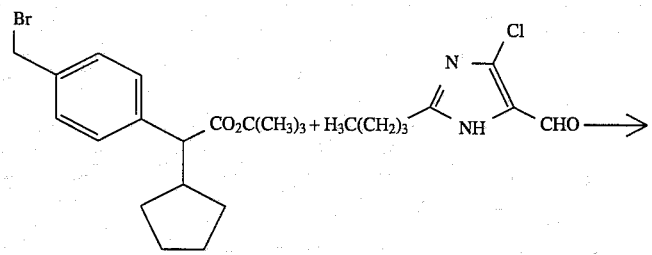

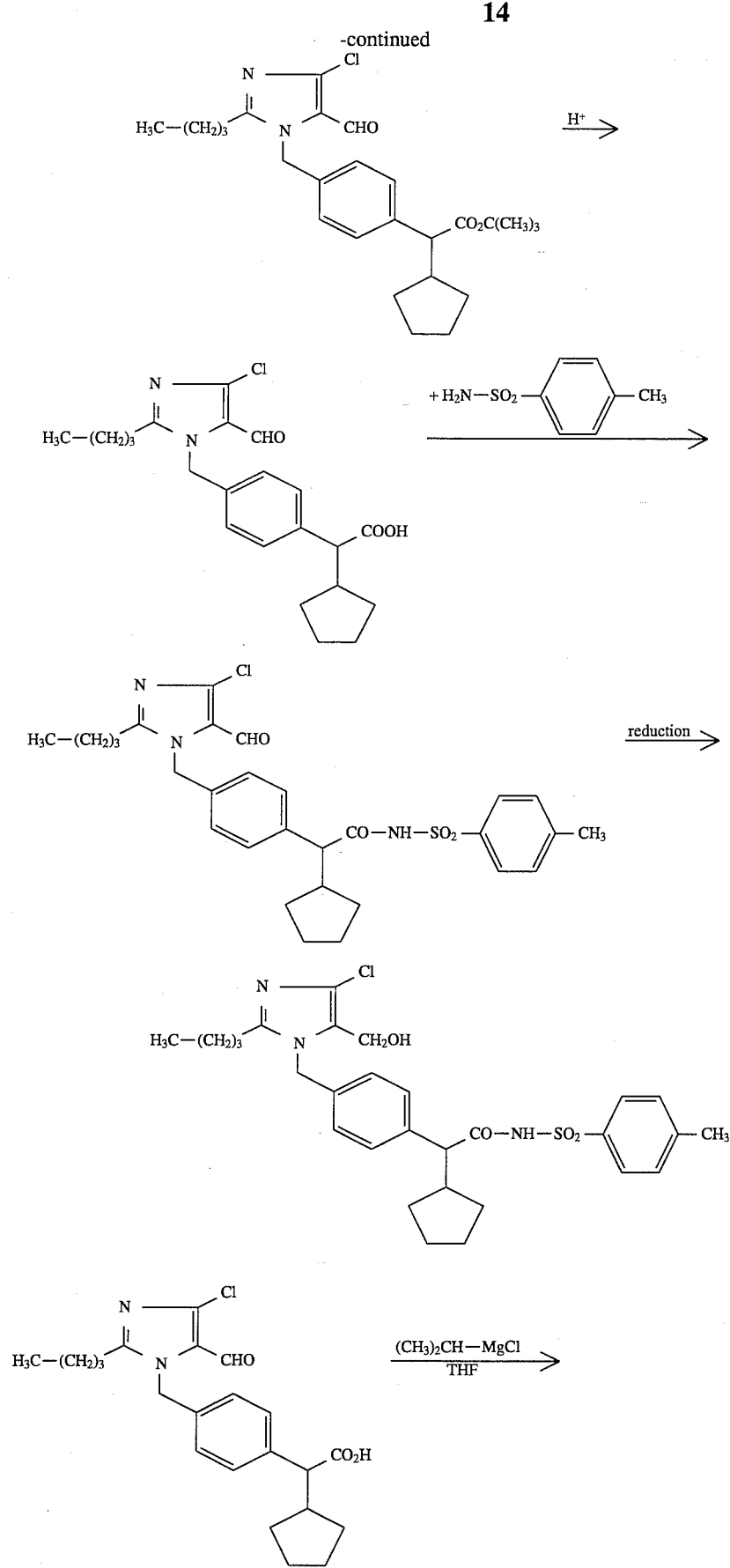

-continued

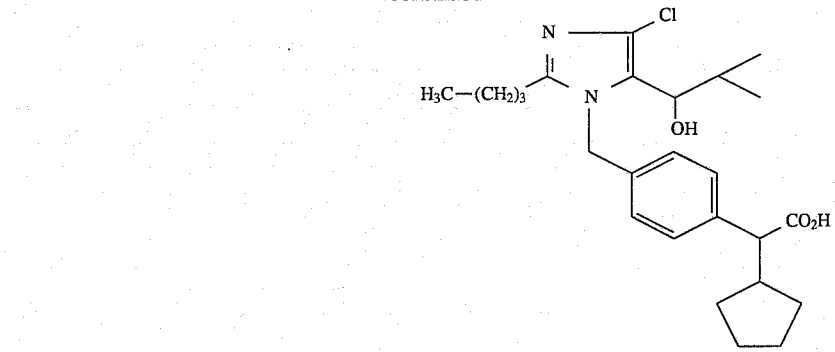

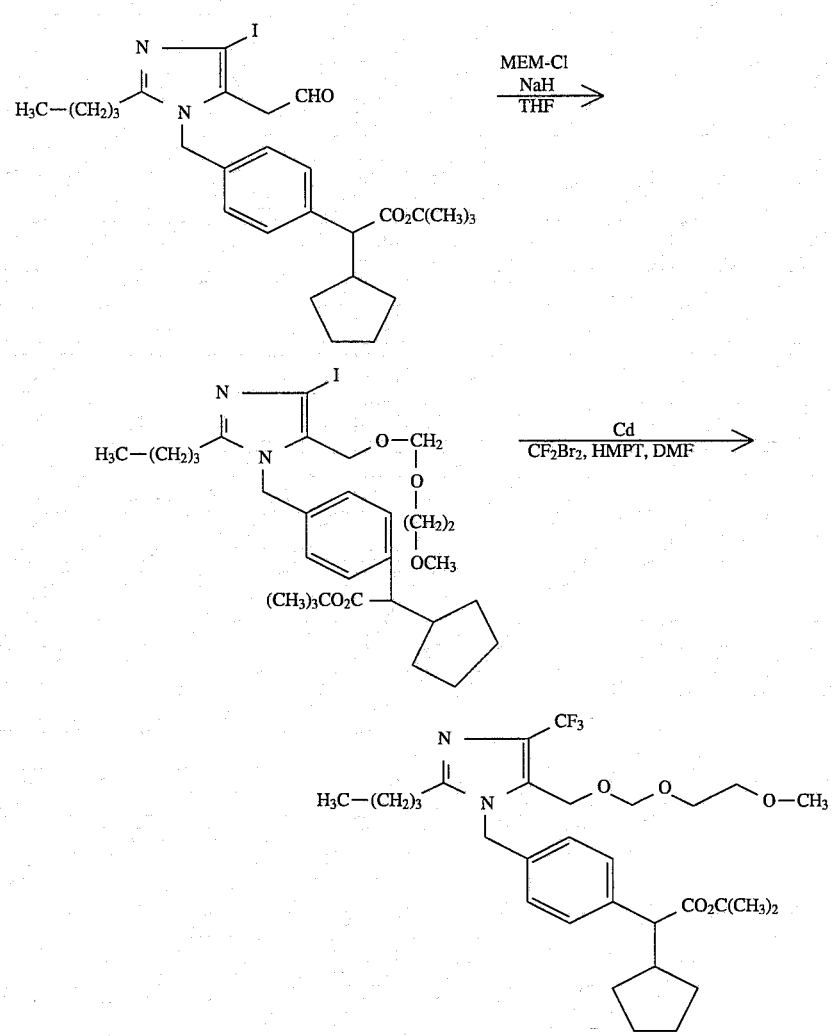

Suitable solvents for the process are customary organic solvents which do not change under the reaction conditions. These preferably include ethers such as diethyl ether, dioxane, tetrahydrofuran or glycol dimethyl ether, or hydrocarbons such as benzene, toluene, xylene, hexane, cyclohexane or mineral oil fractions, or halogenohydrocarbons such as dichloromethane, trichloromethane, tetrachloromethane, dichloroethylene, trichloroethylene or chlorobenzene, or ethyl acetate, triethylamine, pyridine, dimethyl sulphoxide, dimethylformamide, hexamethylphosphoric triamide, acetonitrile, acetone or nitromethane. It is also possible to use mixtures of the solvents mentioned. Dimethylformamide is preferred.

Bases which can be employed for the process according to the invention are in general inorganic or organic bases. These preferably include alkali metal hydroxides such as, for example, sodium hydroxide or potassium hydroxide, alkaline earth metal hydroxides such as, for example, barium hydroxide, alkali metal carbonates such as sodium carbonate or potassium carbonate, alkaline earth metal carbonates such as calcium carbonate, or alkali metal or alkaline earth metal alkoxides such as sodium methoxide or potassium methoxide, sodium ethoxide or potassium ethoxide or potassium tert-butoxide, or organic amines (trialkyl($C_1$–$C_6$)amines) such as triethylamine, or heterocycles such as 1,4-diazabicyclo[2.2.2]octane (DABCO), 1,8-diazabicyclo[5.4.0]undec-7-ene (DBU), pyridine, diaminopyridine, methylpiperidine or morpholine. It is also possible to employ alkali metals, such as sodium or its hydrides such as sodium hydride, as bases. Sodium hydride, potassium carbonate, triethylamine, pyridine and potassium tert-butoxide, DBU or DABCO are preferred.

In general, the base is employed in an amount from 0.05 mol to 10 mol, preferably from 1 mol to 2 mol, relative to 1 mol of the compound of the formula (III).

The process according to the invention is in general carried out in a temperature range from −30° C. to +100° C., preferably from −10° C. to +60° C.

The process according to the invention is in general carried out at normal pressure. However, it is also possible to carry out the process at elevated pressure or at reduced pressure (for example in a range from 0.5 to 5 bar).

Suitable bases for the hydrolysis are the customary inorganic bases. These preferably include alkali metal hydroxides or alkaline earth metal hydroxides such as, for example, sodium hydroxide, potassium hydroxide or barium hydroxide, or alkali metal carbonates such as sodium carbonate or potassium carbonate or sodium hydrogen carbonate, or alkali metal alkoxides such as sodium methoxide, sodium ethoxide, potassium methoxide, potassium ethoxide or potassium tert-butoxide. Sodium hydroxide or potassium hydroxide are particularly preferably employed.

Suitable solvents for the hydrolysis are water or the organic solvents customary for hydrolysis. These preferably include alcohols such as methanol, ethanol, propanol, isopropanol or butanol, or ethers such as tetrahydrofuran or dioxane, or dimethylformamide or dimethyl sulphoxide. Alcohols such as methanol, ethanol, propanol or isopropanol are particularly preferably used. It is also possible to employ mixtures of the solvents mentioned.

The hydrolysis can also be carried out with acids such as, for example, trifluoroacetic acid, acetic acid, hydrochloric acid, hydrobromic acid, methanesulphonic acid, sulphuric acid or perchloric acid, preferably with trifluoroacetic acid.

The hydrolysis is in general carried out in a temperature range from 0° C. to +100° C., preferably from +20° C. to +80° C.

In general, the hydrolysis is carried out at normal pressure. However, it is also possible to work at reduced pressure or at elevated pressure (for example from 0.5 to 5 bar).

When carrying out the hydrolysis, the base is in general employed in an amount from 1 to 3 mol, preferably from 1 to 1.5 mol, relative to 1 mol of the ester. Molar amounts of the reactants are particularly preferably used.

When carrying out the reaction, the carboxylates of the compounds according to the invention are formed in the first step as intermediates which can be isolated. The acids according to the invention are obtained by treating the carboxylates with customary inorganic acids. These preferably include mineral acids such as, for example, hydrochloric acid, hydrobromic acid, sulphuric acid or phosphoric acid. It has proved advantageous in this case in the preparation of the carboxylic acids to acidify the basic reaction mixture from the hydrolysis in a second step without isolation of the carboxylates. The acids can then be isolated in a customary manner. In the case of the basic heterocycles, the salts of the heterocycles with the inorganic acids can also be obtained by treating the solutions of the carboxylates with the abovementioned acids.

The amidation and sulphonamidation with the compounds of the general formulae (IV) and (V) are in general carried out in one of the abovementioned solvents, preferably in tetrahydrofuran or dichloromethane.

The amidation and sulphonamidation may optionally proceed via the activated step of the acid halides (II, $R^3$=CO-halogen), which can be prepared from the corresponding acids by reaction with thionyl chloride, phosphorus trichloride, phosphorus pentachloride, phosphorus tribromide or oxalyl chloride.

The amidation and sulphonamidation are in general carried out in a temperature range from −20° C. to +120° C., preferably from −10° C. to +30° C., and at normal pressure.

In addition to the abovementioned bases, suitable bases for this are preferably triethylamine and/or dimethylaminopyridine, DBU or DABCO.

The base is employed in an amount from 0.5 mol to 10 mol, preferably from 1 mol to 2 mol, relative to 1 mol of the compounds of the general formulae (IV) and (V).

Acid-binding agents which can be employed for the sulphonamidation are alkali metal or alkaline earth metal carbonates such as sodium carbonate or potassium carbonate, alkali metal or alkaline earth metal hydroxides such as, for example, sodium hydroxide or potassium hydroxide, or organic bases such as pyridine, triethylamine or N-methylpiperidine, or bicyclic amidines such as 1,5-diazabicyclo[3.4.0]-non-5-ene (DBN) or 1,5-diazabicyclo[3.4.0]undec-5-ene (DBU). Potassium carbonate is preferred.

Suitable dehydrating reagents are carbodiimides such as, for example, diisopropylcarbodiimide, dicyclohexylcarbodiimide or N-(3-dimethylaminopropyl)-N'-ethylcarbodiimide hydrochloride or carbonyl compounds such as carbonyldiimidazole or 1,2-oxazolium compounds such as 2-ethyl-5-phenyl-1,2-oxazolium-3-sulphonate or propanephosphonic anhydride or isobutyl chloroformate or benzotriazolyloxy-tris-(dimethylamino)phosphonium hexafluorophosphate or diphenyl aminophosphonate or methanesulphonyl chloride, if appropriate in the presence of bases such as triethylamine or N-ethylmorpholine or N-methylpiperidine or dicyclohexylcarbodiimide and N-hydroxysuccinimide [cf. J. C. Sheehan, S. L. Ledis, J. Am. Chem. Soc. 95, 875 (1973); F. E. Frerman et al., J. Biol. Chem. 228, 7087–7093 (1983) and N. Leo Benoton, K. Kuroda, Int. Pept. Res. 13, 403 (1979), 17, 197 (1981) (1981)].

The acid-binding agents and dehydrating reagents are in general employed in an amount from 0.5 mol to 3 mol, preferably from 1 to 1.5 mol, relative to 1 mol of the corresponding carboxylic acids ($R^3$=$CO_2H$).

The hydrolysis of the nitriles is in general carried out in water or one of the abovementioned solvents, preferably in ethanol, isopropanol, ethylene glycol or glycines or their mixtures in the presence of a base, acid, hydrogen peroxide or alkali metal or alkaline earth metal peroxides such as, for example, sodium peroxide.

Suitable bases for the hydrolysis are in general alkali metal or alkaline earth metal hydroxides such as, for example, potassium hydroxide, sodium hydroxide or barium hydroxide. Sodium hydroxide is preferred.

Suitable acids are in general inorganic acids such as, for example, hydrochloric acid or sulphuric acid.

The hydrolysis of the nitriles is in general carried out in a temperature range from −20° C. to +200° C., preferably from +20° C. to +150° C.

The reduction of a double or multiple bond (B=$C_1$–$C_4$-alkenyl or alkynyl) is in general carried out by hydrogenation with hydrogen in the presence of a catalyst such as, for example, platinum or platinum oxides, rhodium, ruthenium, chlorotris(triphenylphosphine)rhodium, or palladium on animal charcoal, preferably with palladium on animal charcoal in a temperature range from 0° C. to +150° C., preferably from +25° C. to +100° C.

Suitable solvents for the hydrogenation are protic solvents such as, for example, methanol or ethanol and/or aprotic solvents such as, for example, tetrahydrofuran, toluene, dimethylformamide, methylene chloride, dioxane or ethyl acetate.

The hydrogenation is carried out at a pressure of 1 to 300 atm, preferably at 1 to 20 atm.

The amount of catalysts employed is 0.05 to 5 mol, preferably 0.1 to 1.5 mol, relative to 1 mol of the compounds of the general formula (I) or (Ia) (B=—HC=CH— or —C≡C—).

The abovementioned derivatisation of the substituents D, E, G, L and M is in general carried out by methods known from the literature, in which, by way of example, the reduction of aldehydes or alkoxycarbonyl compounds to alcohols (a) and the alkylation (b) are intended to be illustrated by the following:

a) The reduction of alkoxycarbonyl compounds or aldehydes to the corresponding alcohols is in general carried out with hydrides, such as lithium aluminium hydride or sodium borohydride, preferably with lithium aluminium hydride in inert solvents such as ethers, hydrocarbons or alcohols or their mixtures, preferably in ethers such as, for example, diethyl ether, tetrahydrofuran or dioxane, or alcohols such as ethanol, in the case of the aldehydes preferably with sodium borohydride in ethanol, in a temperature range from 0° C. to +150° C., preferably from +20° C. to +100° C., at normal pressure.

b) The alkylation is in general carried out in one of the abovementioned solvents using alkylating agents such as, for example, ($C_1$–$C_8$)-alkyl halides, sulphonic acid esters or substituted or unsubstituted ($C_1$–$C_6$)-dialkyl or ($C_1$–$C_{10}$)-diaryl sulphates, preferably methyl iodide, p-toluenesulphonic acid ester or dimethyl sulphate. The alkylation can also be carried out with organometallic compounds, such as, for example, ($C_1$–$C_6$)-alkyllithium compounds, ($C_1$–$C_8$)-alkylmagnesium halides, arylmagnesium halides, in particular the chlorides and bromides, or perfluoro-($C_1$–$C_{10}$)-allylcadmium compounds, it being possible for the respective alkyl chain to be straight-chain or branched.

In these cases, suitable solvents are in particular dimethylformamide, HMPT and tetrahydrofuran.

In the case of the alkyllithium and alkyl- or arylmagnesium halides, the alkylations are carried out in a temperature range from −80° C. to 70° C., preferably from −78° C. to 0° C., and in the case of the perfluorocadmium compounds from room temperature to +100° C., in particular from +40° C. to +80° C.

The compounds of the general formula (II) are known in some cases and can be prepared, for example, by alkylating compounds of the general formula (VI)

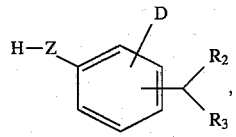

(VI)

in which

Z, D, $R^2$ and $R^{3'}$ have the abovementioned meaning, first with compounds of the general formula (VII)

$$R^{31}—Z \qquad (VII)$$

in which $R^{31}$ has the abovementioned meaning of $R^1$ or $R^2$, but does not represent hydrogen, and Z represents halogen, preferably bromine, in inert solvents, if appropriate in the presence of a base, and in a second step a bromination is carried out on the substituent B by a customary method, if appropriate in the presence of a catalyst.

The alkylation is in general carried out in one of the abovementioned solvents, preferably in dimethylformamide in a temperature range from 0° C. to +70° C., preferably from 0° C. to +30° C. and at normal pressure.

In addition to the abovementioned bases, potassium tert-butoxide is preferably suitable for the alkylation.

The bromination is in general carried out using $Br_2$ or N-bromosuccinimide, preferably using N-bromosuccinimide, in one of the abovementioned solvents, preferably carbon tetrachloride, in a temperature range from 0° C. to +150° C., preferably from 0° C. to +80° C., and at normal pressure.

A suitable starter (catalyst) for the bromination is, for example, azobisisobutyronitrile, dibenzoyl peroxide, preferably azobisisobutyronitrile, the starter being employed in an amount from 0.01 mol to 0.1 mol, preferably from 0.01 mol to 0.05 mol, relative to 1 mol of the compound of the general formula (VI).

The compounds of the general formula (VI) are known per se or can be prepared by known methods [cf. J. Chem. Soc., Perkin Trans. 1, (9), 1706–1707; J. Chem. Soc., Chem. Commun., (2), 167–168].

The compounds of the general formula (VII) are known per se [cf. Beilstein 5, 19/5, 24/5, 29] or can be prepared from the corresponding alcohols or cycloalkenes according to a customary method.

The compounds of the general formula (III) are also known per se [cf., for example, Beilstein 25, 163; 23, 45; U.S. Pat. No. 4,355,040] or can be prepared by a customary method.

The compounds of the general formula (Ia) are new and can be prepared by the abovementioned processes.

The compounds of the general formulae (IV) and (V) are known or can be prepared by known processes [cf., for example, Beilstein 11/104, R. V. Vizgert, Uspekhi, Khimii 32, 3 (1963); Russian Chem. Rev. 32, 1 (1969); Beilstein 4, 87].

The heterocyclically substituted phenylacetic acid derivatives (I) according to the invention exhibit an unforeseeable, useful spectrum of pharmacological action.

The compounds according to the invention have a specific A-II antagonistic action, as they competitively inhibit the binding of angiotensin II to the receptors. They suppress the vasoconstrictory and aldosterone secretion-stimulating effects of angiotensin II. They moreover inhibit the proliferation of smooth muscle cells.

They can therefore be employed in medicaments for the treatment of arterial hypertension and atherosclerosis. Moreover, they can be employed for the treatment of coronary heart diseases, cardiac insufficiency, disorders of cerebral function, ischaemic brain diseases, peripheral circulatory disorders, functional disorders of the kidney and adrenal gland, bronchospastic and vascular diseases of the airways, sodium retention and oedemas.

Investigation of the inhibition of the contraction induced by agonists

Rabbits of either sex are stunned by a blow to the neck and bled out, or occasionally anaesthetised with Nembutal (about 60–80 mg/kg i.v.) and sacrificed by opening the thorax. The thorax aorta is removed, freed from adhering connective tissue, divided into ring segments 1.5 mm wide and individually taken under an initial loading of about 3.5 g into 10 ml organ baths containing 5% carbon dioxide 95% oxygen-gassed Krebs-Henseleit nutrient solution temperature-controlled at 37° C. of the following composition: 119 mmol/l of NaCl; 2.5 mmol/l of $CaCl_2 \times 2\ H_2O$; 1.2 mmol/l of $KH_2PO_4$; 10 mmol/l of glucose; 4.8 mmol/l of KCl; 1.4 mmol/l of $MgSO_4 \times 7\ H_2O$ and 25 mmol/l of $NaHCO_3$.

The contractions are determined isometrically by means of Statham UC2 cells via bridge amplifiers (ifd Mülheim or DSM Aalen) and digitalised and evaluated by means of A/D converters (System 570, Keithley Munich). The agonist dose-response curves (DRC) are carried out hourly. With each DRC, 3 or 4 individual concentrations are applied to the baths at 4 min intervals. After completion of the DRC and the following washing-out cycles (16 times in each case for about 5 sec/min with the abovementioned nutrient solution), a stirring or incubation phase of 28 minutes follows, in the course of which the contractions as a rule reach the starting value again.

The height of the 3rd DRC in the normal case is used as a reference quantity for the evaluation of the test substance to be investigated in further passages, which test substance is applied to the baths in the following DRCs in an increasing dosage in each case at the start of the incubation time. Each aorta ring is in this case always stimulated for the whole day with the same agonists.

Anonists and their standard concentrations
(applications volume per individual dose=100 µl):

| | | |
|---|---|---|
| KCl | 22.7; 32.7; 42.7; 52.7 | mmol/l |
| 1-noradrenaline | $3 \times 10^{-9}$; $3 \times 10^{-8}$; $3 \times 10^{-7}$; $3 \times 10^{-6}$ | g/ml |
| Serotonin | $10^{-8}$; $10^{-7}$; $10^{-6}$; $10^{-5}$ | g/ml |
| B-HT 920 | $10^{-7}$; $10^{-6}$; $10^{-5}$ | g/ml |
| Methoxamine | $10^{-7}$; $10^{-6}$; $10^{-5}$ | g/ml |
| Angiotensin II | $3 \times 10^{-9}$; $10^{-8}$; $3 \times 10^{-8}$; $10^{-7}$ | g/ml |

To calculate the $IC_{50}$ (the concentration at which the substance to be investigated causes a 50% inhibition), the effect is in each case based on the 3rd=submaximal agonist concentration.

The compounds according to the invention inhibit the contraction of the isolated rabbit aorta induced by angiotensin II in a dose-dependent manner. The contraction induced by potassium depolarisation or other agonists was not inhibited or only inhibited weakly at high concentrations.

TABLE A

Inhibition of the vascular contractions of isolated aorta rings of rabbits in vitro
$IC_{50}$ (mol/l) against contractions induced by:

| Ex. No.: | AII | KCl |
|---|---|---|
| I | $>2.2 \times 10^{-4}$ | — |
| II | $4.1 \times 10^{-6}$ | $>10^{-4}$ |

Moreover, the compounds according to the invention inhibit the specific binding of radioactive angiotensin II in a concentration-dependent manner.

Interaction of the compounds according to the invention with the angiotensin II receptor on membrane fractions of the adrenal cortex (cattle)

Adrenal cortices of cattle (ACs), which have been freshly removed and carefully freed from the gland medulla are comminuted in sucrose solution (0.32M) with the aid of an Ultra-Turrax (Janke & Kunkel, Staufen i.B.) to give a coarse membrane homogenate and partially purified in two centrifugation steps to give membrane fractions.

The investigations of receptor binding are carried out on partially purified membrane fractions of bovine ACs using radioactive angiotensin II in an assay volume of 0.25 ml which in particular contains the partially purified membranes (50–80 µg), $^3$H-angiotensin II (3–5 nM), test buffer solution (50 mM tris, pH 7.2, 5 mM $MgCl_2$, 0.25% BSA) and the substances to be investigated. After an incubation time of 60 min at room temperature, the unbound radioactivity of the samples is separated by means of moistened glass fibre filters (Whatman GF/C) and the bound radioactivity is measured spectrophotometrically in a scintillation cocktail after washing the protein with ice-cold buffer solution (50 mM tris/HCl, pH 7.4, 5% PEG 6000). The analysis of the raw data was carried out using computer programs to give $K_i$ and/or $IC_{50}$ values ($K_i$: $IC_{50}$ values corrected for the radioactivity used; $IC_{50}$ values: concentration at which the substance to be investigated causes a 50% inhibition of the total binding of the radio ligand).

Investigation of the inhibition of the proliferation of smooth muscle cells by the compounds according to the invention To determine the antiproliferative action of the compounds, smooth muscle cells are used which have been obtained from the aortas of rats by the media explant technique [R. Ross, J. Cell. Biol. 50, 172, 1971]. The cells are inoculated in suitable culture dishes, as a rule 24-hole plates, and cultured at 37° C. for 2–3 days in medium 199 containing 7.5% FCS and 7.5% NCS, 2 mM L-glutamine and 15 mM HEPES, pH 7.4 in 5% $CO_2$. The cells are then synchronised by withdrawal of serum for 2–3 days and then stimulated to growth with AII, serum or other factors. Test compounds are added at the same time. After 16–20 hours, 1 µCi of $^3$H-thymidine is added and after a further 4 hours the incorporation of this substance into the TCA-precipitatable DNA of the cells is determined.

The new active compound can be converted in a known manner into the customary formulations, such as tablets, coated tablets, pills, granules, aerosols, syrups, emulsions, suspensions and solutions, using inert, non-toxic, pharmaceutically suitable excipients or solvents. In this case, the therapeutically active compound should in each case be present in a concentration of about 0.5 to 90% by weight of the total mixture, i.e. in amounts which are sufficient in order to achieve the dosage range indicated.

The formulations are prepared, for example, by extending the active compounds with solvents and/or excipients, if appropriate using emulsifiers and/or dispersants, it optionally being possible to use organic solvents as auxiliary solvents, for example in the case of the use of water as a diluent.

Administration is carried out in a customary manner, preferably orally or parenterally, in particular perlingually or intravenously.

In the case of parenteral use, solutions of the active compound can be employed using suitable liquid excipient materials.

In general, it has proved advantageous on intravenous administration to administer amounts of about 0.001 to 1 mg/kg, preferably about 0.01 to 0.5 mg/kg of body weight to achieve effective results, and on oral administration the dosage is about 0.01 to 20 mg/kg, preferably 0.1 to 10 mg/kg, of body weight.

In spite of this, it may be necessary to depart from the amounts mentioned, in particular depending on the body weight or the type of application route, on individual behaviour toward the medicament, or the manner of its formulation and the time or interval at which administration takes place. Thus, in some cases it may be sufficient to manage with less than the abovementioned minimum amount, while in other cases the upper limit mentioned must be exceeded. In the case of the administration of relatively large amounts, it may be advisable to divide these into several individual doses over the course of the day.

Solvents
A=dichloromethane:methanol=10:1
B=dichloromethane:methanol=50:1
C=dichloromethane:methanol=20:1
D=petroleum ether:ethyl acetate=1:2
E=petroleum ether:ethyl acetate=2:1
F=methylene chloride:methanol=9:1
G=methylene chloride:methanol:acetic acid=9:1:0.1
H=ethyl acetate:petroleum ether=7:3
I=ethyl acetate:petroleum ether=3:7
J=ethyl acetate:petroleum ether=4:1
K=ethyl acetate:petroleum ether=1:1
L=ethyl acetate:petroleum ether=10:1
M=petroleum ether:ethyl acetate=5:1
N=petroleum ether:ether=5:1
O=toluene:dioxane:glacial acetic acid=75:21:3
P=methylene chloride:methanol=95:5
Q=ethyl acetate:methanol=4:1

Definition of Isomers:
4 dia=mixture of the four possible diastereomers if two asymetric C-atoms are present in the molecule
dia A/rac=racemic diastereomer with higher $R_f$-value
dia B/rac=racemic diastereomer with lower $R_f$-value
dia A/ent=diastereomer with higher $R_f$-value (one enantiomer)
dia B/ent=diastereomer with lower $R_f$-value (one enantiomer)
2 dia/ent=mixture of two enantiomerically pure diastereomers
rac=racemate
ent=enantiomer
Starting compounds

EXAMPLE 1 tert-Butyl 4-methylphenylacetate

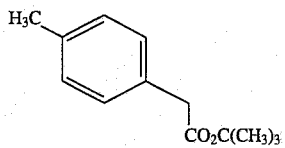

450 g (3 mol) of 4-methylphenylacetic acid, 1.13 l (12 mol) of tert-butanol and 90 g (0.74 mol) of dimethylaminopyridine are dissolved in 2 l of dichloromethane. After addition of 680 g (3.3 mol) of dicyclohexylcarbodiimide, dissolved in 400 ml of dichloromethane, the mixture is stirred at 25° C. for 20 h, the precipitated urea is filtered off with suction and washed with 200 ml of dichloromethane, and the organic phase is washed twice each with 500 ml of 2N hydrochloric acid and water. The organic phase is concentrated and distilled.

Yield: 408 g (66% of theory)
Boiling point: 73°–78° C./0.2 mm

EXAMPLE 2 tert-Butyl 2-cyclopentyl-2-(4-methylphenyl)acetate

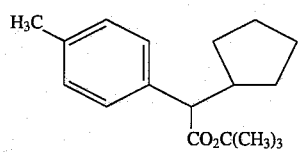

33.5 g (0.3 mol) of potassium tert-butoxide are initially introduced into 100 ml of DMF at 0° C. with exclusion of moisture, and 51.6 g (0.25 mol) of tert-butyl 4-methylphenylacetate in 250 ml of DMF are added dropwise. The mixture is stirred at 0° C. for 30 min and 32.2 ml (0.3 mol) of cyclopentyl bromide in 150 ml of DMF are added dropwise at 5°–15° C. and the mixture is stirred at 25° C. for 20 h. After concentration, the residue is partitioned between water/diethyl ether, and the ether phase is dried over sodium sulphate and concentrated. The product crystallises out.

Yield: 67 g (97.5% of theory)
Solidification point: 51°–53° C.

EXAMPLE 3 tert-Butyl 2-(4-bromomethyl-phenyl)-2-cyclopentyl-acetate

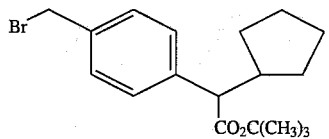

27.4 g (0.1 mol) of tert-butyl 2-cyclopentyl-2-(4-methylphenyl)-acetate are dissolved in 200 ml of carbon tetrachloride and the solution is heated to boiling. After addition of 0.82 g of azobisisobutyronitrile, 18.7 g (0.105 mol) of N-bromosuccinimide are added in portions and the mixture is then refluxed for 1 h, cooled to 0° C. and filtered off from the succinimide. After concentration of the filtrate the product precipitates. It is washed with petroleum ether (40/60) and dried.

Yield: 20 g (57% of theory)
Solidification point 73°–76° C.

EXAMPLE 4 tert-Butyl 2-(4-trifluoromethanesulphonyloxy-phenyl)-2-cyclopentyl-acetate

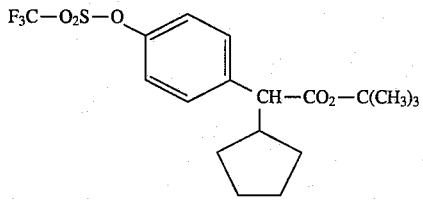

14.1 g (55 mmol) of trifluoromethanesulphonic anhydride are added at 0° C. to a solution of 13.8 g (50 mmol) of tert-butyl 2-(4-hydroxy-phenyl)-2-cyclopentyl-acetate in 25 ml of pyridine. The solution is stirred at room temperature for a further 2 h and then poured into ice-water. The customary aqueous work-up yields 19.3 g of a crude product which is chromatographed on silica gel (CH$_2$Cl$_2$).

Yield: 18.7 g (91.4% of the title compound).
R$_f$(CH$_2$Cl$_2$): 0.9.

EXAMPLE 5 tert-Butyl 2-(4-vinyl-phenyl)-2-cyclopentyl-acetate

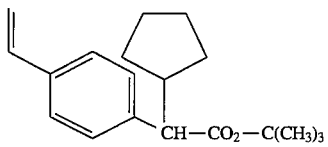

2.04 g (5 mmol) of the compound from Example 4, 1.58 g (5 mmol) of tributylvinyltin and 1.27 g (30 mmol) of LiCl are added to a solution of 46 mg of trifurylphosphine and 50 mg of Pd(dba)$_2$ in 20 ml of N-methylpyrrolidinone. The solution is stirred at room temperature for 16 h, then water is added and it is worked up with water. The crude product obtained is chromatographed on silica gel. 1.14 g (80.0%) of the title compound are obtained.

R$_f$ (petroleum ether/ether 20:1):0.6.

EXAMPLE 6 tert-Butyl 2-[4-(2-hydroxyethyl)phenyl]-2-cyclopentyl-acetate

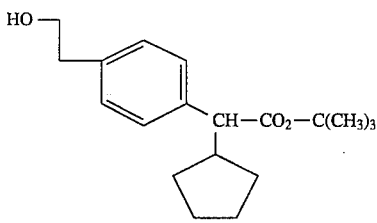

188 mg (1.54 mmol) of borabicyclononane are added at 0° C. to a solution of 400 mg (1.4 mmol) of the compound of Example 5 in 0.3 ml of CH$_2$Cl$_2$ and the mixture is in each case then stirred at room temperature for 2 h and at 80° C. for 2 h. 100 µl of H$_2$O (5.6 mmol), 473 µl of H$_2$O$_2$ (4.6 mmol) and 513 µl of NaOH (3M, 1.54 mmol) are then added and the mixture is stirred at 60° C., and then at room temperature for 16 h. The customary aqueous work-up yields 647 mg of a crude product which is chromatographed on silica gel.

Yield: 134 mg (34.5%) of the title compound.
R$_f$ (petroleum ether/ether 1:1):0.24.

EXAMPLE 7 tert-Butyl 2-[4-(2-toluenesulphonyloxyethyl)phenyl]-2-cyclopentyl-acetate

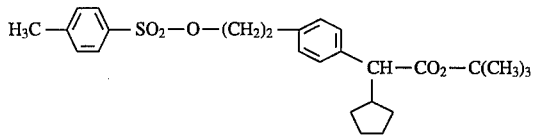

65 mg (0.34 mmol) of toluenesulphonyl chloride are added at 4° C. to a solution of 100 mg (0.33 mmol) of the compound of Example 6, 48 mg (0.34 mmol) of triethylamine and 4 mg (0.03 mmol) of dimethylaminopyridine in 350 µl of CH$_2$Cl$_2$ and the mixture is stirred at 4° C. for 4 h and then at room temperature for 1 h. 12 µl (0.66 mmol) of H$_2$O are added to the solution, and it is stirred at room temperature for 0.5 h, 4 µl of acetic acid are added and the mixture is worked up with water. A crude product is obtained which, after chromatography on silica gel (cyclohexane/ether 15:1), yields 103 mg (67%) of the title compound.

R$_f$ (petroleum ether/ether 1:1):0.78.

EXAMPLE 8 tert-Butyl 2-[4-(3-hydroxypropenyl)phenyl]-2-cyclopentyl-acetate

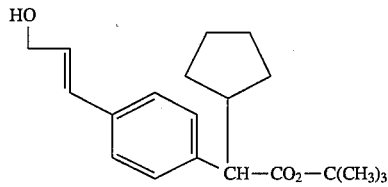

1.7 g (5.0 mmol) of 3-tributylstannyl-3-propenol, 46 mg of trifurylphosphine, 1.27 g (30 mmol) of LiCl and 50 mg of Pd(dba)$_2$ are added to a solution of 2.04 g (5.0 mmol) of the compound of Example 4 in 10 ml of N-methylpyrrolidinone. The solution formed is stirred at room temperature for 4.5 h and then worked up with water. The crude product obtained is chromatographed on silica gel (petroleum ether/ethyl acetate 5:1). 830 mg (52.5% of theory) of the title compound are obtained.

R$_f$ (petroleum ether/ether 7:3):0.34.

EXAMPLE 9 tert-Butyl 2-[4-(3-hydroxypropyl)phenyl]-2-cyclopentyl-acetate

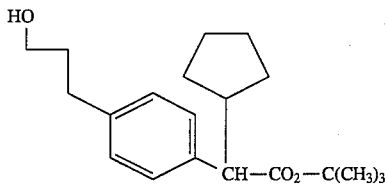

300 mg (0.94 mmol) of the compound of Example 8 are added to a suspension of 90 mg of Pd on calcium carbonate in 4 ml of ethanol and the mixture is hydrogenated with H$_2$ at 50° C. and a pressure of 90 bar for 4.0 h. The reaction mixture obtained is filtered off from the catalyst through a double layer of silica gel and Celite and all volatile components are removed in vacuo. The residue obtained is chromatographed on silica gel (petroleum ether/ethyl acetate 40:1). 234 mg (78%) of the title compound are obtained.

R$_f$ (petroleum ether/ether 7:3):0.34.

EXAMPLE 10 tert-Butyl 2-[4-(3-toluenesulphonyloxypropyl)phenyl]-2-cyclopentyl-acetate

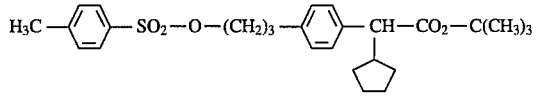

96 μl (0.69 mmol) of triethylamine and 8 mg (0.06 mmol) of dimethylaminopyridine at 0° C. are added to a solution of 200 mg (0.63 mmol) of the compound of Example 9 in 650 μl of CH₂Cl₂. 131 mg (0.69 mmol) of toluenesulphonyl chloride are added at this temperature and the mixture obtained is slowly allowed to warm to room temperature. After 16 h, 23 μl (1.26 mmol) of H₂O are added, and the mixture is stirred for 0.5 h and worked up with water. The crude product obtained is chromatographed on silica gel (petroleum ether/ethyl acetate 40:1). 170 mg (57% of theory) of the title compound are obtained.

R_f (petroleum ether/ethyl acetate 20:1):0.15.

EXAMPLE 11 tert-Butyl 2,2-dimethyl-2-(4-methylphenyl)acetate

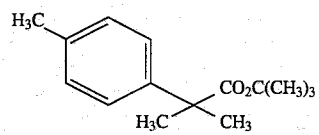

30 g (0.145 mol) of tert-butyl 4-methylphenylacetate in 175 ml of DMF are added dropwise with stirring at 0° C. to 19.6 g (0.175 mmol) of potassium tert-butoxide in 70 ml of DMF. After stirring for 30 min, 25 g (0.175 mol) of methyl iodide in 100 ml of DMF are slowly added dropwise with exclusion of light. After warming to room temperature, the mixture is stirred overnight, again cooled to 0° C. and the sequence is repeated by means of addition of potassium tert-butoxide in DMF and methyl iodide in DMF.

After concentration, the residue is partitioned between diethyl ether and water, the water phase is extracted with ether twice more, and the combined ether phases are dried over sodium sulphate and concentrated.

Yield: 26.5 g (78% of theory).

EXAMPLE 12

Methyl 2-(4-bromomethyl-phenyl)-acetate

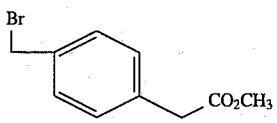

5 g (22 mmol) of 2-(4-bromomethyl-phenyl)-acetic acid are stirred at room temperature overnight in 50 ml of 2,2-dimethoxypropane with addition of 2 ml of aqueous conc. hydrochloric acid. After concentration, methanol is added twice in each case, the mixture is concentrated again and the residue is then dried in vacuo.

Yield: 5.3 g (>99% of theory).

EXAMPLE 13

2-[4-(2-Butyl-4-chloro-5-formyl-imidazol-1-yl-methyl)-phenyl]-acetic acid

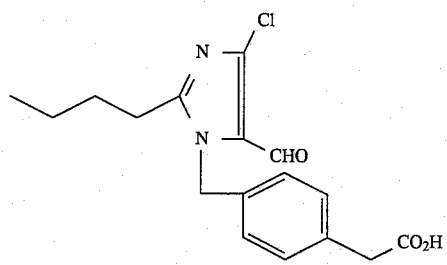

3.3 g (9.5 mmol) of methyl 2-[4-(2-butyl-4-chloro-5-formyl-imidazol-1-yl-methyl)-phenyl]-acetate are dissolved in 100 ml of dioxane/water (1:1) at 0° C. and a solution of 0.44 g (10.4 mmol) of lithium hydroxide monohydrate in 5 ml of water is added dropwise with stirring. After stirring at room temperature for 3 h, the mixture is concentrated to a half, diluted with water, washed with diethyl ether, and the aqueous phase is acidified with 1N hydrochloric acid and extracted three times with ethyl acetate. The combined ethyl acetate phases are dried over sodium sulphate and concentrated.

Yield: 3.2 g (>99% of theory).

EXAMPLE 14 tert-Butyl 2-(1H-imidazolyl)-2-oxo-acetate

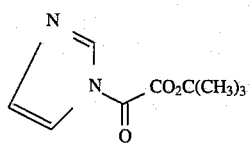

58.5 g (0.79 mol) of tert-butanol are added with stirring at 0° C. under argon to 100 g (0.79 mol) of oxalyl chloride in 1.3 l of THF. After stirring at 0° C. for 1 hour, 161 g (2.37 mol) of imidazole in 0.7 l of THF are added dropwise in the course of 60 min. After a further 15 min, the mixture is filtered, the solid is washed with 0.5 l of THF, and the filtrate is concentrated to a volume of 1 l, filtered again, then completely concentrated, allowed to stand overnight at 0° C. under argon and again filtered through a frit.

Yield: 137 g (89% of theory)

¹H-NMR (250 MHz, CDCl₃): δ=1.63 (s, 9H, tert-butyl).

EXAMPLE 15 tert-Butyl 2-(4-methyl-phenyl)-2-oxo-acetate

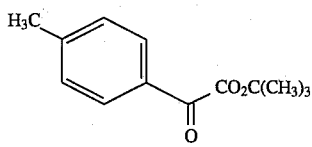

0.7 l of a 1M solution (0.7 mol) of p-toluenemagnesium bromide in diethyl ether is added dropwise with stirring at −78° C. under argon to 136.9 g (0.7 mol) of tert-butyl 2-(1 H-imidazolyl)-2-oxo-acetate in 2.5 l of THF. The mixture is then brought to 0° C. in the course of 3 h, poured into ice-water and extracted three times with diethyl ether with addition of acetic acid to prevent the formation of emulsion. The combined ether phases are washed with aqueous sodium chloride solution and dried over sodium sulphate, and the product is distilled.

Yield: 77.3 g (50% of theory)

Boiling point: 116°–119° C. (1 mm Hg).

EXAMPLE 16 tert-Butyl 2-(4-methyl-phenyl)-2-phenyl-2-hydroxy-acetate

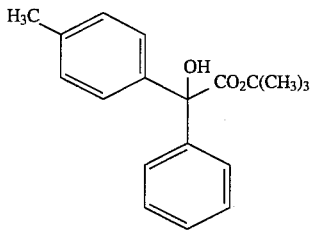

30 ml of a 2M solution (60 mmol) of phenyllithium in benzene/diethyl ether (3:1) are added dropwise at 0° C. with stirring to 13.2 g (60 mmol) of tert-butyl 2-(4-methyl-phenyl)-2-oxo-acetate under argon in 70 ml of THF and the mixture is stirred at room temperature for a further 1 h. The mixture is diluted with 80 ml of diethyl ether, poured into 150 ml of water with stirring, neutralised with 1N acetic acid and extracted three times with diethyl ether. The combined organic phases are dried over sodium sulphate and concentrated, and the product is chromatographed on silica gel 60 using 40–60 petroleum ether/ethyl acetate (4:1).

Yield: 13.3 g (74% of theory).

EXAMPLE 17

2-(4-Methyl-phenyl)-2-phenyl-acetic acid

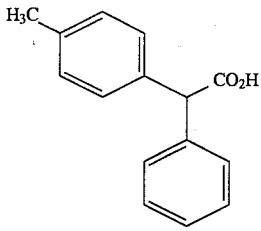

1.49 g (5 mmol) of tert-butyl 2-(4-methyl-phenyl)- 2-phenyl-2-hydroxy-acetate are stirred at room temperature in 60 ml of dichloromethane for 3 h with 6.3 ml (40 mmol) of triethylsilane and 12.6 ml (60 mmol) of trifluoroacetic acid. The mixture is diluted with 60 ml of water, adjusted to a pH of 2–3 with saturated aqueous bicarbonate solution and shaken. After removal of the organic phase, the aqueous phase is extracted twice more with dichloromethane. The combined organic phases are dried over sodium sulphate, filtered and concentrated. The product is chromatographed on silica gel 60 using 40–60 petroleum ether/ethyl acetate (6:4).

Yield: 0.80 g (71% of theory).

EXAMPLE 18

5-[(1-Cyclopentyl)-1-(3-methylphenyl)]-methyl-tetrazole

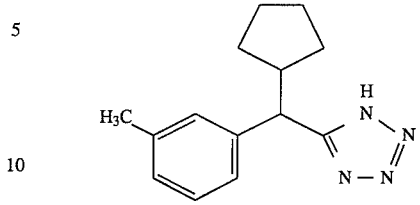

19.5 g (97.8 mmol) of 2-cyclopentyl-2-(3-methylphenyl)-acetonitrile are dissolved in 350 ml of DMF p.a., 63.6 g (97.8 mmol) of sodium azide and 134.33 g (97.8 mmol) of triethylammonium chloride are added and the mixture is boiled under reflux for 24 h. After cooling, 1M sulphuric acid is added and the mixture is extracted with ether. The organic phase is shaken with 2M sodium hydroxide solution and the alkaline aqueous phase is then acidified with 1M sulphuric acid. The product is extracted with ether, and the ethereal solution is dried with sodium sulphate and evaporated.

Yield: 20.0 g (82.4 mmol)

$R_f$ (dichloromethane:methanol=20:1):0.40.

EXAMPLE 19

5-[(1-Cyclopentyl)-1-(3-methylphenyl)]methyl- 2-triphenylmethyl-tetrazole

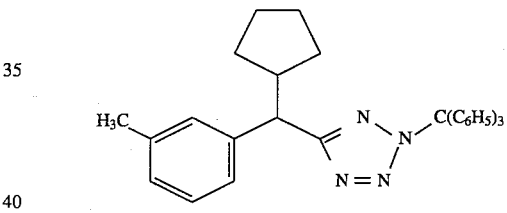

19.9 g (82.0 mmol) of the compound from Example 18 are dissolved in 250 ml of dichloromethane and reacted at room temperature for 24 h with 24.8 g (86.7 mmol) of triphenylmethyl chloride and 13.7 g (98.7 mmol) of triethylamine. The mixture is extracted successively with 250 ml of water, 200 ml of 1M aqueous citric acid and 200 ml of water. The organic phase is dried with sodium sulphate, concentrated and freed from residual solvent in a high vacuum.

Yield: 38.8 g (80.1 mmol)

$R_f$ (toluene): 0.40.

EXAMPLES 20 and 21

2-Cyclopentyl-2-(4-methylphenyl)-acetonitrile (20)

2,2-Dicyclopentyl-2-(4-methylphenyl)-acetonitrile (21)

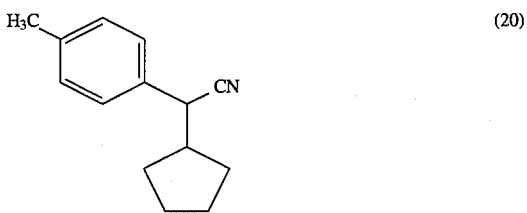

(20)

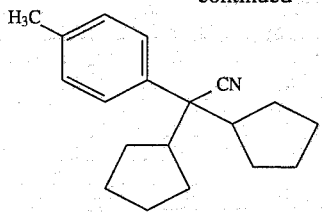

(21)

Potassium tert-butoxide (6.6 g; 59 mmol) was added at −10° C. to a solution of 4-methylphenyl-acetonitrile (5.0 g; 38 mmol) and cyclopentyl bromide (5.7 ml; 53 mmol) in DMF (70 ml) and the mixture was stirred overnight at room temperature. The reaction solution was acidified with 1M KHSO$_4$ solution (pH 3–4) and concentrated. The residue was taken up in methylene chloride, washed three times with water, dried over Na$_2$SO$_4$, filtered and concentrated. Filtration of the residue on silica gel (hexane/ethyl acetate—step gradient) and subsequent HPLC (Lichroprep Si60, hexane-:ethyl acetate=10:1) gave 3.45 g of 2,2-dicyclopentyl-2-p-tolyl-acetonitrile [33.8% of theory; R$_f$=0.53 (hexane:ethyl acetate=10:1)] and 4.29 g of 2-cyclopentyl-2-(4-methylphenyl)-acetonitrile (56.5% of theory; R$_f$=0.4) as a yellow oil.

EXAMPLE 22

5-[1-Cyclopentyl-1-(4-methylphenyl)methyl]-tetrazole

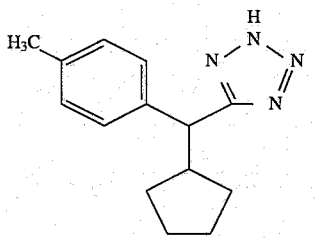

A solution of the compound from Example 20 (7.2 g; 36 mmol), triethylammonium chloride (18 g; 0.13 mol) and sodium azide (8.2 g; 0.13 mol) in DMF (110 ml) was boiled under reflux under argon for 60 h. The reaction solution was concentrated, acidified with 1M KHSO$_4$ solution and partitioned between water and ethyl acetate. The organic phase was washed, dried over Na$_2$SO$_4$ and concentrated to give 10.6 g of a yellow oil [theory: 8.7 g, residue DMF; R$_f$: 0.53 (dichloromethane:methanol:acetic acid=20:1:0.1)].

EXAMPLE 23

5-[1-Cyclopentyl-1-(4-methylphenyl)]-2-triphenylmethyl-tetrazole

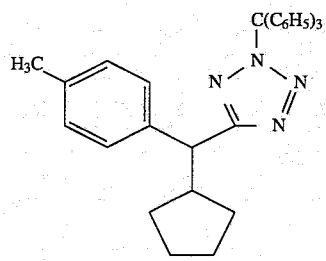

A solution of Example 22 (10.6 g crude; 36 mmol), triphenylmethyl chloride (11.5 g; 41 mmol) and triethylamine (7.0 ml; 49 mmol) in dichloromethane (160 ml) was boiled under reflux for 5 h, washed with 1M KHSO$_4$ solution after cooling, dried over Na$_2$SO$_4$ and concentrated. The residue was triturated with hexane/ethyl acetate (5:1) and filtered to give 12.7 g of yellowish crystals [63.8% of theory; m.p.: 138°–9° C.; R$_f$: 0.58 (hexane:ethyl acetate=5:1)].

EXAMPLES 24 and 25

5-[1-(4-Bromomethyl-phenyl)-1-cyclopentyl-methyl]-2-triphenylmethyl-tetrazole (24)
5-[1-bromo-1-(4-bromomethyl-phenyl)-1-cyclopentyl-methyl]-2-triphenylmethyl-tetrazole (25)

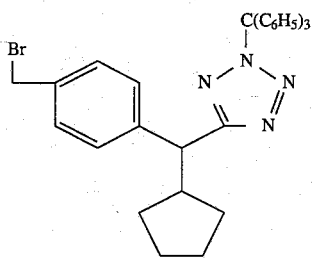

(24)

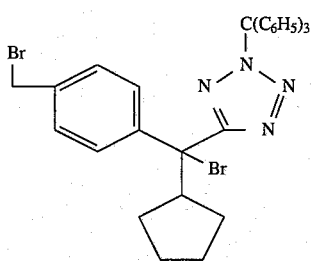

(25)

A solution of Example 23 (5.0 g; 11 mmol), N-bromosuccinimide (2.1 g; 11 mmol) and a spatula tip full of azoisobutyronitrile in carbon tetrachloride (500 ml) was boiled under reflux for 2 h, cooled, filtered and concentrated to give 6.6 g of a mixture of starting material, bromide and dibromide (theory: 5.9 g).

EXAMPLE 26

5-{1-Cyclopentyl-1-[4-(2-butyl-4-chloro-5-formyl-imidazol-1-yl-methyl)-phenyl]-methyl}-2-triphenylmethyl-tetrazole

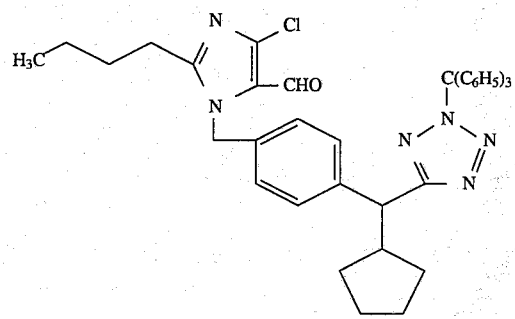

A solution of 2-butyl-4-chloro-5-formyl-imidazole (1.53 g; 8.2 mmol) in DMF (60 ml) was added dropwise at −10° C. to a suspension of 80% sodium hydride/paraffin oil dispersion (0.35 g; 12 mmol) in DMF (30 ml), and the mixture was stirred at 0° C. for 15 min. A solution of Example 24 (6.6 g crude; 11 mmol) in DMF (60 ml) was added dropwise at −10° C. and the mixture was stirred at room temperature overnight. Concentration and silica gel chromatography (toluene:ethyl acetate=9:1) yielded 2.28 g of a yellow oil [29% of theory; R$_f$: 0.57 (toluene:ethyl acetate=5:1)].

EXAMPLE 27

2-(4-Bromomethyl-phenyl)-2,2-dicyclopentyl-acetonitrile

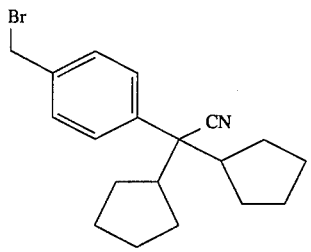

Bromination of Example 21 analogously to Example 24 yielded 1.88 g of a clear oil [70% of theory; $R_f$: 0.58 (hexane:ethyl acetate=10:1)].

EXAMPLE 28

2-Butyl-5-hydroxymethyl-4-iodo-imidazole

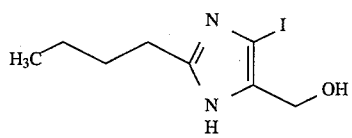

4-DMAP (1.2 g; 10 mmol) and N-iodosuccinimide (25 g; 111 mmol) were added to a solution of 2-butyl- 4-hydroxymethyl-imidazole (15.4 g; 100 mmol) in dioxane (210 ml) and 2-methoxyethanol (140 ml) and the mixture was stirred overnight at 50° C. Concentration gave 44.4 g of a brownish-yellow magma (theory; 28 g), which was further reacted without further purification.

For characterisation, 2 g of the crude product were dissolved using ethyl acetate and washed with 5% NaHCO$_3$ solution and saturated sodium chloride solution. Drying and concentration of the organic phases gave 1.2 g of a yellow solid [97% of theory; m.p.: 135°–40° C. (dec.); $R_f$: 0.24 (methylene chloride:methanol=10:1)].

EXAMPLE 29

2-Butyl-5-formyl-4-iodo-imidazole

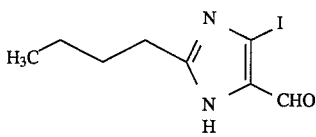

A solution of ammonium cerium nitrate (125 g; 228 mmol) in water (320 ml) was added to a solution of Example 28 (42 g crude; 95 mmol) in ethyl acetate (90 ml) and the mixture was stirred overnight. The aqueous phase was extracted three times with ethyl acetate, then rendered alkaline with NaHCO$_3$ and extracted again with ethyl acetate. The combined organic phases were washed with 5% strength NaHCO$_3$ solution and saturated sodium chloride solution, dried and concentrated. Silica gel chromatography of the residue (hexane/ethyl acetate step gradient) gave 19.2 g of a yellow solid [72% of theory; m.p. 80°–5° C.; $R_f$: 0.54 (methylene chloride:methanol=10:1)].

EXAMPLE 30

(2-Hydroxy-phenyl)-glycinol hydrochloride

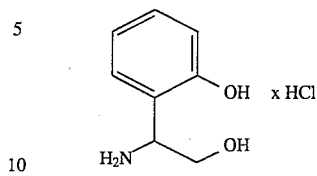

2.18 g (10 mmol) of (2-hydroxy-phenyl)-glycine methyl ester hydrochloride are dissolved in 20 ml of dry THF and reacted at room temperature (25° C.) for 18 hours with 3.34 g (33 mmol) of triethylamine and 2.39 g (22 mmol) of trimethylchlorosilane. The resulting precipitate is filtered off with suction and washed with dry THF, and the filtrate is reacted at 25° C. with lithium aluminium hydride (0.76 g/38.0 mmol). Excess reagent is then filtered off with suction, the filtrate is washed with dry THF, water is added and the mixture is diluted with ether (pH≈10). The aqueous phase is adjusted to pH=2 with 2M hydrochloric acid, washed with ether and lyophilised. Yield 1.20 g (6.3 mmol).

$R_f$=0.38 (eluent: BABA*)

* Preparation of the eluent BABA: 200 ml of n-butyl acetate, 36 ml of n-butanol, 100 ml of glacial acetic acid and 60 ml of buffer (87.9 ml of 1/15M aqueous potassium dihydrogen phosphate solution and 12.1 ml of 1/15M aqueous disodium hydrogen phosphate solution) are shaken and the organic phase is employed as the eluent.

The compounds shown in Table I are prepared in analogy to the procedure of Example 30.

TABLE I

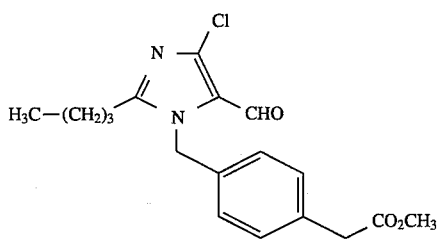

| Ex. No. | R | $R_f$ (eluent) |
|---|---|---|
| 31 | 3-OH | 0.23 dichloromethane:methanol = 5:1 |
| 32 | 4-OH | 0.34 BABA* |

EXAMPLE 33

Methyl-2-[4-(2-butyl-4-chloro-5-formyl-imidazole-1-yl-methyl)phenyl]-acetate

The compound is prepared in analogy to the procedure of Example 26.

PREPARATION EXAMPLES

EXAMPLE I tert-Butyl 2-[4-(2-butyl-4-chloro-5-formyl-imidazol-1-yl-methyl)phenyl]-2-cyclopentyl-acetate

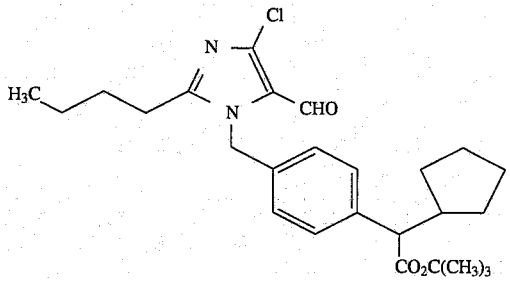

1.6 g (0.053 mol) of sodium hydride (80% strength) are suspended in 50 ml of DMF under protective gas, 10 g (0.053 mol) of 2-butyl-5-formyl-4-chloroimidazole (preparation according to EP 324,377) in 100 ml of DMF are added dropwise at 0° C., the mixture is then stirred at 0° C. for 15 min and 18.9 g (0.053 mol) of tert-butyl 2-(4-bromomethylphenyl-2-cyclopentylacetate in 100 ml of DMF are added dropwise. The mixture is stirred at 0° C. for 2 h, the solvent is evaporated, the residue is taken up in diethyl ether and filtered and, after concentration, chromatographed on silica gel 60 using dichloromethane.

Yield: 16.2 g (66.7% of theory)

Solidification point: 101°–102° C.

EXAMPLE II

2-[4-(2-Butyl-4-chloro-5-formyl-imidazol-1-yl-methyl)-phenyl]-2-cyclopentylacetic acid

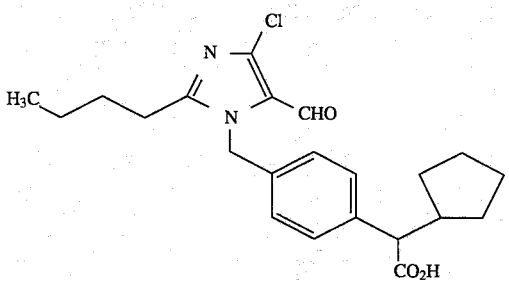

2.3 g (5 mmol) of the compound from Example I are stirred at 25° C. for 5 h in 5 ml of dichloromethane and 5 ml of trifluoroacetic acid. After concentration, the crude product is chromatographed on silica gel 60 using dichloromethane/methanol (100:5).

Yield: 1.8 g (87.6% of theory)
Solidification point: 95°–98° C.

EXAMPLE III

N-4-Tolylsulphonyl-2-[4-(2-butyl-4-chloro-5-formyl-imidazol-1-yl-methyl)-phenyl]-2-cyclopentyl-acetamide

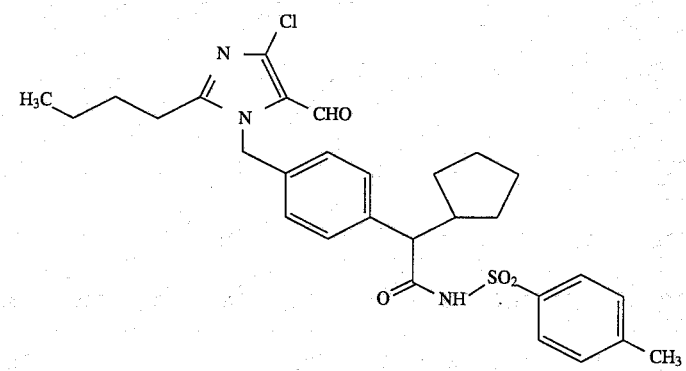

1.2 g (2.6 mmol) of the compound from Example II are dissolved in 30 ml of THF, then 0.72 mol (5.2 mmol) of triethylamine, 0.23 ml (2.9 mmol) of mesyl chloride, 320 mg (2.6 mmol) of DMAP and 535 mg (3.1 mmol) of 4-tolylsulphonamide in 10 ml of THF are added successively at 0° C. The mixture is stirred at 25° C. for 20 h, 0.4 ml of glacial acetic acid and 30 ml of water are added, the mixture is extracted three times with 30 ml of ethyl acetate, the organic is phase is concentrated and the residue is chromatographed on silica gel 60 using dichloromethane/methanol (100:2).

Yield: 1.3 g (90.3% of theory)
Solidification point: 85° C.

EXAMPLE IV

N-4-Tolylsulphonyl-2-[4-(2-butyl-4-chloro-5-hydroxy-methyl-imidazol-1-yl-methyl-phenyl]-2-cyclopentyl-acetamide

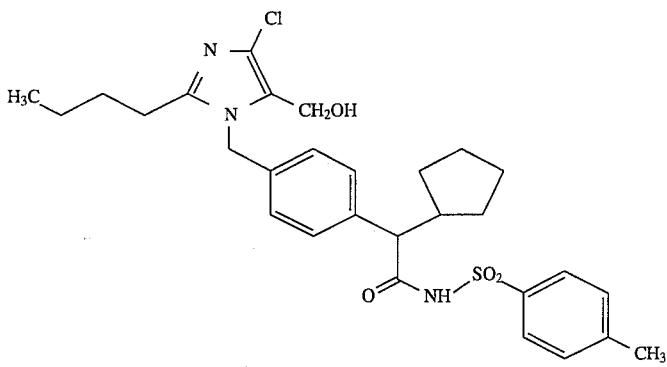

556 mg (1 mmol) of the compound from Example III are dissolved in 10 ml of ethanol and reacted with 37.8 mg (1 mmol) of sodium borohydride. After 15 min, 20 ml of water are added, and the mixture is acidified with dilute hydrochloric acid and extracted twice with 20 ml of ethyl acetate. The organic phase is dried over sodium sulphate, concentrated and chromatographed on silica gel 60 using ethyl acetate/petroleum ether (1:1).

Yield: 502 mg (90% of theory)
Solidification point: 96° C.

EXAMPLE V

2-[4-(2-Butyl-4-chloro-5-formyl-imidazol-1-yl-methyl)-phenyl]-2-cyclopentylacetic acid L-phenylglycinolamide

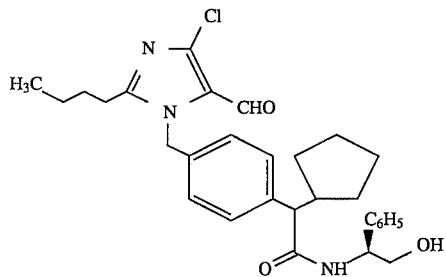

325 mg (0.79 mol) of the compound from Example II are dissolved in 5 ml of THF and 0.22 ml (1.58 mmol) of triethylamine and 0.07 ml (0.87 mmol) of mesyl chloride are added at −30° C. and the mixture is stirred for 30 min. After addition of 97 mg (0.79 mmol) of DMAP and 130 mg (0.96 mmol) of L-phenylglycinol in 5 ml of THF, the mixture is stirred at 25° C. for 20 h. After addition of 10 ml of water, the mixture is acidified with 0.15 ml of glacial acetic acid and extracted three times with 10 ml of glacial acetic acid, the organic phase is dried over sodium sulphate and concentrated, and the residue is chromatographed on silica gel 60 using ethyl acetate/petroleum ether (1:1).

Yield: 264 mg (64% of theory)
Solidification point: 110° C.

EXAMPLE VI tert-Butyl 2-[4-[(2-(Carboxy-propyl)-benzimidazol-1-yl)-methyl]phenyl]-2-cyclopropyl-acetate

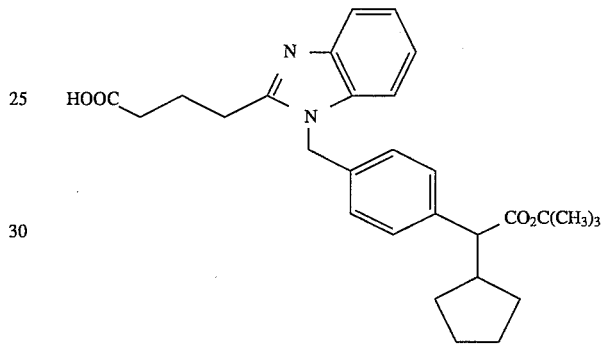

9.7 g (20 mmol) of the compound of Example XVI are dissolved in 100 ml of methanol and reacted with 40 ml of 1M sodium hydroxide solution at room temperature over the course of 2 h. The alcohol is evaporated, 100 ml of water are added to the mixture and the solution thus obtained is adjusted to pH 6 with 2M hydrochloric acid. The precipitate obtained is filtered off with suction, washed with water and dried in vacuo over phosphorus pentoxide.

Yield: 9.0 g
$R_f$=0.37 (dichloromethane:methanol=10:1).

The Examples shown in Tables I and II are prepared in analogy to the procedure of Examples I–VI:

TABLE I

[Structure: benzimidazole with L—(CH2)n substituent on C2, N1 bears CH2-C6H4-CH(R3)(cyclopentyl)]

| Example No. | L | n | R³ | R_f/solvent | Analogously to Example |
|---|---|---|---|---|---|
| VII | —CO₂H | 3 | —CO₂H | 0.03 A | II |
| VIII | —CO₂CH₃ | 3 | —CO₂H | 0.23 A | II |
| IX | H | 4 | —CO—NH—CH(C₆H₅)—CH₂OH | 0.10 B | V |
| X | H | 4 | —CO₂H | 0.20 C | II |
| XI | H | 0 | —CO—NH—CH(C₆H₅)—CH₂OH | 0.44 B | V |
| XII | H | 0 | —CO—NH—CH(C₆H₅)—CH₂OH | 0.39 B | V |
| XIII | H | 0 | —CO—NH—SO₂—C₆H₄—CH₃ | 0,26 B | IV |
| XIV | H | 0 | —CO₂H | 0,52 A | II |
| XV | —CO₂CH₃ | 3 | —CO₂C(CH₃)₃ | 0,45 D | I |

TABLE II

[Structure: 4,5-dichloroimidazole with L on C2, N1 bears CH2-C6H4-CH(R3)(cyclopentyl)]

| Example No. | L | R³ | R_f/solvent | Analogously to Example |
|---|---|---|---|---|
| XVI | (CH₃)₂—CH—NH—CO— | —CO—NH—CH(C₆H₅)—CH₂OH | 0.23 B | V |
| XVII | (CH₃)₂—CH—NH—CO— | —CO—NH—SO₂—C₆H₄—CH₃ | 0.39 E | IV |
| XVIII | CH₃CH₂— | —CO₂H | 0.57 A | II |
| XIX | (CH₃)₂—CH—NH—CO— | —CO₂H | 0.15 B | II |

EXAMPLE XX tert-Butyl 2-[4-[3-(2-butyl-4-chloro-5-formyl-imidazol-1-yl)propyl]phenyl]-2-cyclopentyl-acetate

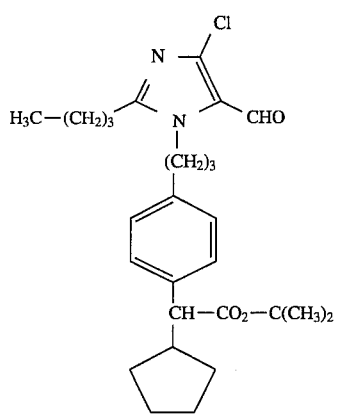

8 mg (0.25 mmol) of NaH are added to a solution of 47 mg (0.254 mmol) of 2-butyl-4-chloro-5-formyl-imidazole in 259 μl of DMF and the mixture is stirred at 0° C. for 0.5 h. 120 mg (0.25 mmol) of the compound of Example 10 and 5 mg of LiI are then added and the mixture is left at room temperature for 24 h and then stirred at 60° C. for 24 h. The aqueous work-up yields a crude product which, after chromatography on silica gel (petroleum ether/ether 10:1), yields 46 mg (38%) of the title compound.

$R_f$ (petroleum ether/ether 5:1):0.48.

EXAMPLE XXI tert-Butyl 2-[4-[2-(2-butyl-4-chloro-5-formyl-imidazol-1-yl)ethyl]phenyl]-2-cyclopentyl-acetate

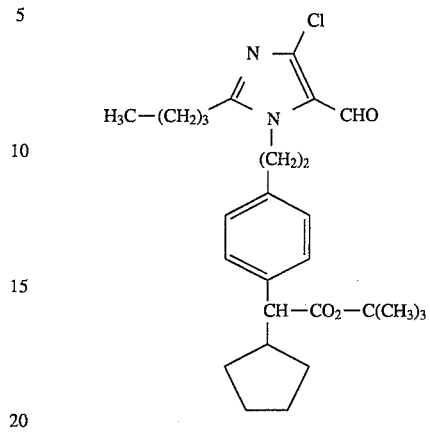

6.6 mg (0.22 mmol) of an 80% strength suspension of NaH in mineral oil are added at 0° C. to a solution of 43 mg (0.23 mmol) of 2-butyl-4-chloro-5-formyl-imidazole in 250 μl of DMF and the mixture is stirred at this temperature for 1 h. 100 mg (0.22 mmol) of the compound of Example 7 in 250 μl of DMF and 10 mg of LiI are added and the mixture is stirred at 0° C. for 4 h and then at room temperature for 16 h. The customary aqueous work-up yielded a crude product which, after chromatography on silica gel, yields 36 mg (33%) of the title compound.

$R_f$ (petroleum ether/ether 5:1):0.42.

The compounds shown in Tables III and IV are prepared in analogy to the Examples indicated therein:

TABLE III

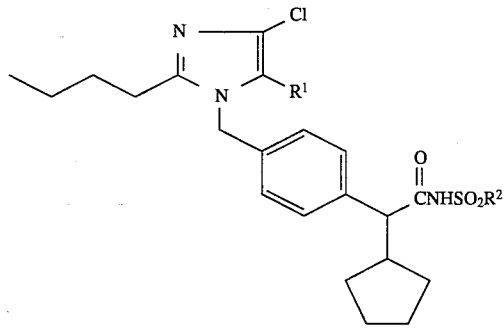

| Example No. | $R^1$ | $R^2$ | m.p. °C./$R_f$(*) | Preparation analogously to Example |
|---|---|---|---|---|
| XXII | CHO | —CH₃ | 79–81° C. | III |
| XXIII | CH₂OH | —CH₃ | 94–96° C. | IV |
| XXIV | CHO | —H₂C—C₆H₅ | 96–98° C. | III |
| XXV | CH₂OH | —H₂C—C₆H₅ | 188–190° C. | IV |
| XXVI | CHO | —C₆H₄—Cl | 72–74° C. | III |

TABLE III-continued

[Structure: imidazole with Cl, R¹, N=C-butyl, N-CH₂-phenyl-CH(cyclopentyl)-C(=O)NHSO₂R²]

| Example No. | R¹ | R² | m.p. °C./R_f(*) | Preparation analogously to Example |
|---|---|---|---|---|
| XXVII | CH₂OH | 4-Cl-C₆H₄– | 0.59 (F) | IV |
| XXVIII | CHO | 3-CF₃-C₆H₄– | 80–82° C. | III |
| XXIX | CH₂OH | 3-CF₃-C₆H₄– | 102–104° C. | IV |
| XXX | CHO | –CH=CH–C₆H₅ | 93–95° C. | III |
| XXXI | CH₂OH | –CH=CH–C₆H₅ | 124–126° C. | IV |

TABLE IV

[Structure: imidazole with Cl, CH₂OH, N=C-butyl, N-CH₂-phenyl-C(R¹)(R²)R³]

| Example No. | R¹ | R² | R³ | R_f(*) | * | Preparation analogously to Example |
|---|---|---|---|---|---|---|
| XXXII | –C₆H₅ | OH | –COOH | 0.10 (F) | rac | 14-16/IV |
| XXXIII | –C₆H₅ | OH | –CONH–CH(C₆H₅)–CH₂OH | 0.36 (F) | dia | 14-16/IV |
| XXXIV | –C₆H₅ | OH | –CONHSO₂p Tol** | 0,29 (F) | rac | 14-16/IV |
| XXXV | –C₆H₅ | H | –COOH | 0.29 (F) | rac | 14-17/IV |

TABLE IV-continued

| Example No. | R¹ | R² | R³ | $R_f$(*) | * | Preparation analogously to Example |
|---|---|---|---|---|---|---|
| XXXVI | —C₆H₅ | H | —CONH-CH(C₆H₅)-CH₂OH | | | |
| XXXVII | —C₆H₅ | H | —CONHSO₂p Tol** | | | |

**pTol = —C₆H₄—CH₃

EXAMPLE XXXVIII tert-Butyl 2-[4-(2-butyl-5-formyl-imidazol-1-yl-methyl)-phenyl]-2-cyclopentyl-acetate

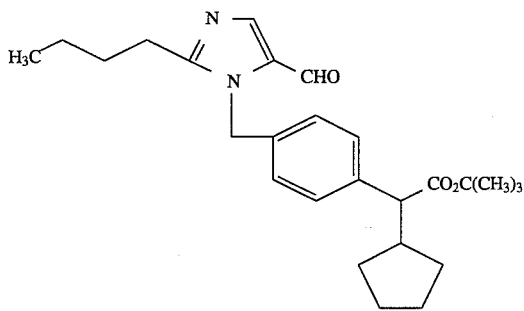

A solution of 21.8 g (47.5 mmol) of tert-butyl 2-[4-(2-butyl-4-chloro-5-formyl-imidazol-1-yl-methyl)phenyl]-2-cyclopentyl-acetate in 200 ml of methanol is hydrogenated at a hydrogen pressure of about 2 bar for 1 h at 25° C. in the presence of 2.18 g of palladium on active carbon (5 strength) and 6.47 g (47.5 mmol) of sodium acetate trihydrate. The solution is then filtered off from the catalyst and concentrated, and the residue is chromatographed on silica gel 60 using ethyl acetate/petroleum ether (1:1).

Yield: 14 g (70% of theory)

$R_f$ (ethyl acetate/petroleum ether—1:1):0.41.

EXAMPLE XXXIX

Ethyl (E,E)-[2-n-butyl-1-{(1-tert-butoxycarbonyl-1-cyclopentyl-methylphenyl- 4-yl)-methyl}-1H-imidazol-5-yl]2,4-pentadienoate

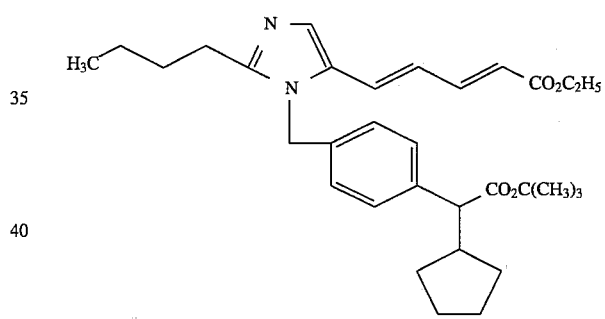

250 mg (10.4 mmol) of sodium hydride (80% strength) are suspended under protective gas in 20 ml of THF, 2.18 g (8.7 mmol) of triethyl 4-phosphonocrotonate are added dropwise at 25° C., the mixture is then stirred at 25° C. for 1 h and 2.54 g (6.0 mmol) of tert-butyl 2-[4-(2-n-butyl-5-formyl-imidazol-1-yl-methyl)phenyl]-2-cyclopentyl-acetate in 10 ml of THF are added dropwise. The mixture is stirred at 25° C. for 20 h. After concentration, the residue is partitioned between water/ethyl acetate, the organic phase is dried over sodium sulphate and concentrated, and the residue is chromatographed on silica gel 60 using ethyl acetate/petroleum ether (1:2).

Yield: 1.5 g (48% of theory)

$R_f$ (ethyl acetate/petroleum ether=1:1):0.55.

EXAMPLE XL

Ethyl(E,E)-[2-n-butyl-2-{(1-carboxy-1-cyclopentyl)methyl-phenyl-4-yl)methyl}-1H-imidazol-5-yl]-2,4-pentadienoate

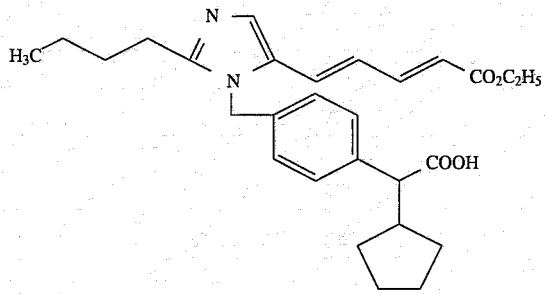

1.44 g (2.77 mmol) of the compound from Example XXXVIII are reacted analogously to Example II.

Yield: 1.29 g (100% of theory)

$R_f$ (ethyl acetate/petroleum ether=1:1):0.40.

EXAMPLE XLI

Methyl 3-[2-n-butyl-1-{(1-tert-butoxycarbonyl-1-cyclopentyl)methyl-phenyl- 4-yl)-methyl}-1H-imidazol-5-yl]-3-hydroxy-2-(2-thienyl)methyl-propionate

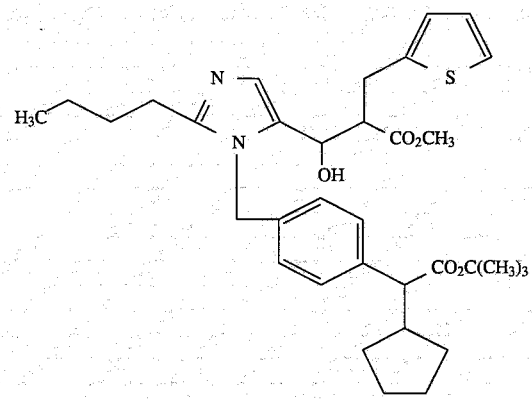

7.2 ml of a 1.6N solution of n-butyllithium in n-hexane are injected at −78° C. under protective gas into a solution of 1.24 g (12.25 mmol) of N,N-diisopropylamine in 15 ml of THF. The reaction mixture is then briefly warmed to 0° C. and is again cooled to −78° C., and 1.79 g (10.5 mmol) of methyl 3-thienylpropionate in 5 ml of THF are added. The mixture is stirred at −78° C. for 45 min, 2.98 g (7.0 mmol) of the compound from Example XL in 5 ml of THF are added and the mixture is stirred at −78° C. for 30 min. It is then slowly warmed to 25° C., 15 ml of satd. ammonia chloride solution are added and the mixture is extracted three times with 50 ml of ethyl acetate each time. The organic phase is dried over sodium sulphate and concentrated, and the residue is chromatographed on silica gel 60 using ethyl acetate/petroleum ether (4:1).

Yield: 3.0 g (76% of theory)

$R_f$ (ethyl acetate/petroleum ether=4:1):0.37.

EXAMPLE XLII

Methyl 3-acetoxy-3-[2-n-butyl-1-{1-tert-butoxycarbonyl-1-cyclopentyl)methylphenyl-4-yl)methyl}-1H-imidazol-5-yl]-2-(2-thienyl)methyl-propionate

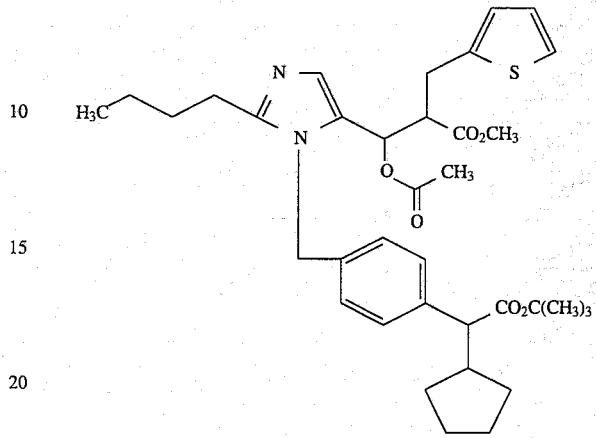

3.0 g (5.0 mmol) of the compound from Example XLI are dissolved in 70 ml of dichloromethane. 220 mg (1.8 mmol) of N,N-dimethylaminopyridine (DMAP) and 8.0 g (7.95 mmol) of acetic anhydride are then added successively and the mixture is stirred at 25° C. for 2 h. 150 ml of ether are added, the mixture is washed successively with 25 ml each of satd. sodium hydrogen carbonate solution and satd. sodium chloride solution, dried over sodium sulphate and concentrated, and the residue is chromatographed on silica gel 60 using ethyl acetate/petroleum ether (1:1).

Yield: 2.14 g (67% of theory)

$R_f$ (ethyl acetate/petroleum ether=1:1):0.34.

EXAMPLE XLIII

Methyl (E)-3-[2-n-butyl-1-{(1-tert-butoxycarbonyl- 1-cyclopentyl)methylphenyl-4-yl)-methyl}-1H-imidazol- 5-yl]-2-(2-thienyl)methyl-2-propenoate

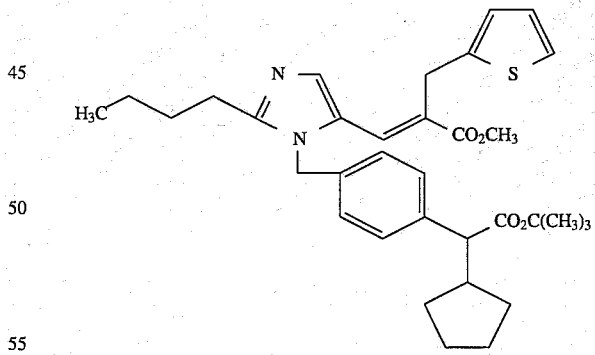

2.14 g (3.4 mmol) of the compound from Example XLII are dissolved in 30 ml of toluene. 1.28 g (8.4 mmol) of 1,8-diazabicyclo[5.4.0]undec-7-ene (DBU) are then added and the mixture is stirred at 80° C. for 3.5 h. After cooling, it is taken up in toluene/H$_2$O, the organic phase is washed with satd. sodium chloride solution, dried over sodium sulphate and concentrated, and the residue is chromatographed on silica gel 60 using ethyl acetate/petroleum ether (1:1).

Yield: 1.45 g (75% of theory)

$R_f$ (ethyl acetate/petroleum ether=1:2):0.36.

EXAMPLE XLIV

Methyl (E)-3-[2-n-butyl-1-{(1-carboxy-1-cyclopentyl)-methylphenyl- 4-yl)methyl}-1H-imidazol-5-yl]-2-(2-thienyl)methyl-2-propenoate

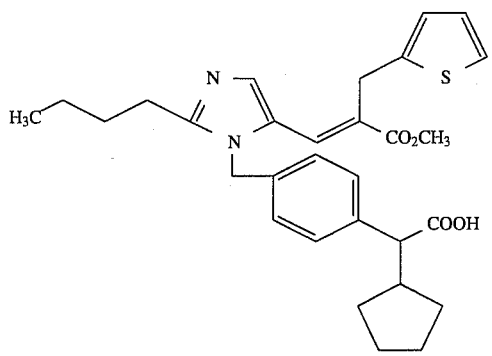

1.39 g (2.4 mmol) of the compound from Example XLIII are reacted analogously to Example II.
Yield: 1.25 g (100% of theory)
$R_f$ (ethyl acetate/petroleum ether=3:1):0.48.

EXAMPLE XLV (E)-3-[2-n-butyl-1-{(1-carboxy-1-cyclopentyl)methyl-phenyl- 4-yl)methyl}-1H-imidazol-5-yl]-2-(2-thienyl)-methyl-2-propenoic acid

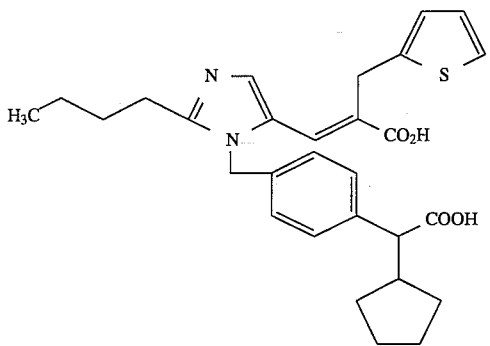

500 mg (0.96 mmol) of the compound from Example XLIV are dissolved in 20 ml of methanol, 5 ml of a 7N NaOH are added and the mixture is stirred at 25° C. for 2 h. The reaction mixture is acidified to pH 1 with hydrochloric acid, extracted twice with 20 ml of ethyl acetate each time, the organic phase is dried over sodium sulphate and concentrated, and the residue is chromatographed on silica gel 60 using ethyl acetate/methanol (30:1).
Yield: 150 mg (31% of theory)
$R_f$ (ethyl acetate/methanol=10:1):0.66.

EXAMPLE XLVI

Methyl (E)-3-[2-n-butyl-1-{(1-cyclopentyl-1-L-phenylglycinolcarbamoyl)methylphenyl- 4-yl)methyl}-1H-imidazol-5-yl]-2-(2-thienyl)methyl-2-propenoate

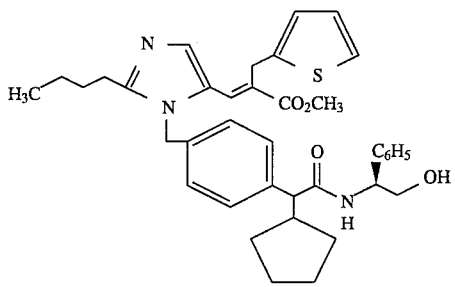

500 mg (0.96 mmol) of the compound from Example XLV are reacted analogously to Example V.
Yield: 270 mg (44% of theory)
$R_f$ (ethyl acetate/petroleum ether=4:1):0.53.

The examples shown in Table V are prepared in analogy to the procedures of Examples XLIII to XLVI:

TABLE V

| Ex. No. | $R^1$ | $R^2$ | $R^3$ |
|---|---|---|---|
| XLVII | —H | —$C_2H_5$ | —$OC(CH_3)_3$ |
| XLVIII | —$OCH_3$ | —$CH_3$ | —OH |

The examples shown in Table VI are prepared in analogy to the examples mentioned therein.

TABLE VI

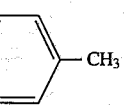

| Ex. No. | M | R² | X | Y | J | R_f(*) | Preparation analogously to Example |
|---|---|---|---|---|---|---|---|
| XLIX | H₃C—(CH₂)₃— | —CO₂H | N | CH | CH | 0.32 (C) | II |
| L | H₃C—(CH₂)₃— | —CONH—CH(C₆H₅)—CH₂OH | N | CH | CH | 0.45 (J) | III |
| LI | H₃C—(CH₂)₃— | —CO—NH—SO₂—C₆H₄—CH₃ | N | CH | CH | 0.38 (J) | V |
| LII | H₃C—(CH₂)₃— | —CONH—CH(C₆H₅)—CH₂OH | N | CH | CH | 0.27 (J) | V |
| LIII | H₃C—(CH₂)₃— | —CO₂H | HC | N | CH | 0.47 (A) | II |
| LIV | H₃C—(CH₂)₃— | —CO₂H | HC | CH | N | 0.40 (A) | II |
| LV | H₃C—(CH₂)₃— | —CO₂H | N | HC | C—Br | 0.65 (D) | II |
| LVI | H₃C—(CH₂)₃— | —CONH—CH(C₆H₅)—CH₂OH | N | HC | C—Br | 0.14 (K) | V |
| LVII | H₃C—(CH₂)₃— | —CO—NH—SO₂—C₆H₄—CH₃ | N | HC | C—Br | 0.66 (K) | III |
| LVIII | F₃C— | —CO₂H | N | HC | CH | 0.61 (L) | II |
| LIX | H₃C—CH₂—CH=CH— | —CO₂H | N | HC | CH | 0.52 (J) | II |
| LX | cyclopropyl | —CO₂H | N | HC | CH | 0.60 (A) | II |
| LXI | C₂H₅ | —CO₂H | N | HC | CH | 0.18 (B) | II |

EXAMPLES LXII and LXIII

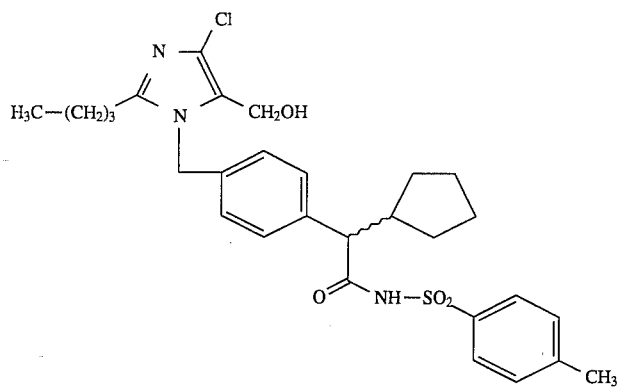

After separation of the racemate from Example IV on a chiral phase, the two enantiomers a) (+)-enantiomer of N-4-tolylsulphonyl-2-[4-(2-butyl-4-chloro-5-hydroxymethyl-imidazol-1-yl-methyl)-phenyl]-2-cyclopentylacetamide
$\alpha_D^{20}$=99.3 (c=1, $C_2H_5OH$) (LXII)

b) (−)-enantiomer of N-4-tolylsulphonyl-2-[4-(2-butyl-4-chloro-5-hydroxymethyl-imidazol-1-yl-methyl)-phenyl]-2-cyclopentylacetamide
$\alpha_D^{20}$=−91.4 (c=1, $C_2H_5OH$) (LXIII) are obtained.

EXAMPLE LXIV and LXV

2-[4-(2-Butyl-4-chloro-5-hydroxymethyl-imidazol-1-yl-methyl)phenyl]-2-cyclopentylacetic acid L-phenylglycinolamide

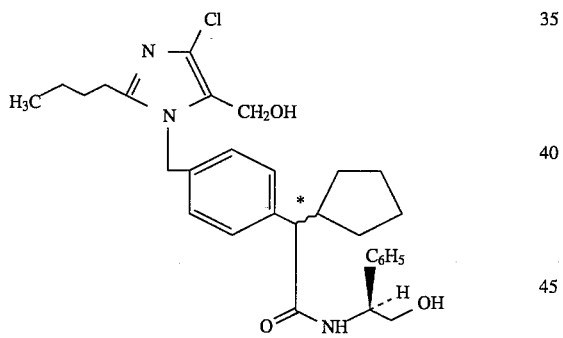

0.1 g (2.9 mmol) of sodium borohydride is added to 1.5 g (2.9 mmol) of the compound from Example V in 25 ml of ethanol. After 1 h at room temperature, the reaction mixture is acidified (pH 4) with 2N HCl and extracted three times with $CH_2Cl_2$. The organic phase is dried over $Na_2SO_4$ and concentrated, and the product is crystallised from ethyl acetate/petroleum ether. A 1:1 mixture of the diastereomers is obtained.

Solidification point: 112°–5° C.

Yield: 1.0 g (66% of theory).

The diastereomers are separated chromatographically by silica gel using petroleum ether/ethyl acetate (3:7).

Diastereomer A: solidification point 82°–87° C.

Diastereomer B: solidification point 151°–4° C.

EXAMPLE LXVI

N-4-Tolylsulphonyl-2-[4-(2-butyl-5-carboxy-4-chloro-imidazol-1-yl-methyl)-phenyl]-2-cyclopentylacetamide

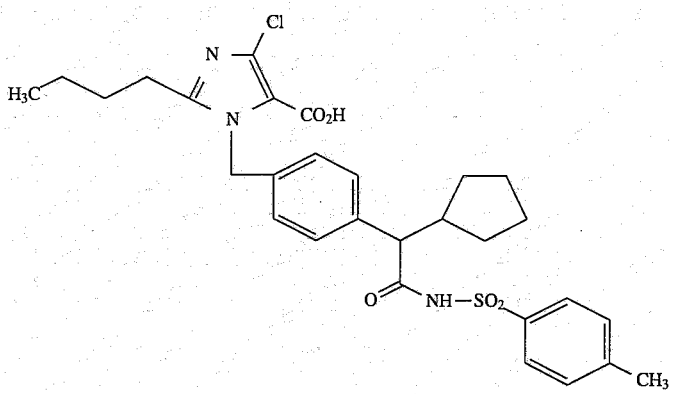

250 mg (0.45 mmol) of the compound from Example III are dissolved in 2.5 ml (0.45 mmol) of pyridine and 162 mg of tetrabutylammonium permanganate, dissolved in 1.5 ml of pyridine, are added at 60° C., and the mixture is stirred at 60° C. for 2 h. The pyridine is evaporated, and the residue is taken up in water, acidified with dilute HCl and extracted with ethyl acetate. The organic phase is concentrated and the residue is chromatographed on silica gel 60 using $CH_2Cl_2$/MeOH (10:1).

Solidification point: 138° C.

Yield: 90 mg (35% of theory).

EXAMPLE LXVII tert-Butyl 2-[4-(2-butyl-4-chloro-5-hydroxymethyl-imidazol-1-yl-methyl)phenyl]-2-cyclopentylacetate

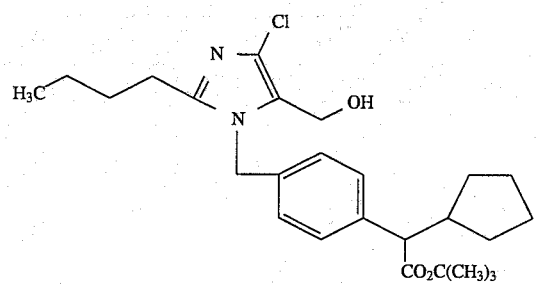

265 mg (7 mmol) of sodium borohydride are added to 3.2 g (7 mmol) of the compound from Example I in 30 ml of EtOH and the mixture is stirred at 25° C. for 1 h. After addition of dilute HCl (pH 6), the mixture is extracted three times with $CH_2Cl_2$, the organic phase is dried over $Na_2SO_4$ and concentrated, and the residue is chromatographed on silica gel 60 using petroleum ether/ethyl acetate (1:1).

Solidification point: 112°–4° C.

Yield: 2.4 g (74.4% of theory).

EXAMPLE LXVIII

2-[4-(2-Butyl-4-chloro-5-hydroxymethyl- imidazol-1-yl-methyl)phenyl]-2-cyclopentylacetic acid

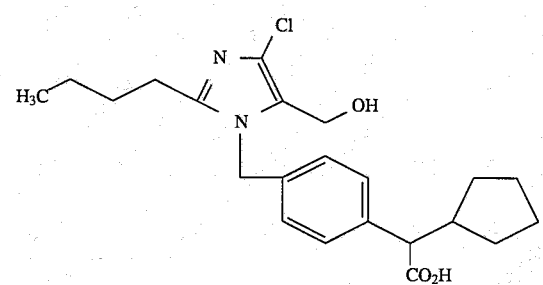

2.1 g (4.5 mmol) of the compound from Example IX are stirred at room temperature for 5 h in 10 ml of $CH_2Cl_2$ and 10 ml of trifluoroacetic acid. The reaction mixture is evaporated. The residue is taken up in $CH_2Cl_2$, washed with water, dried, concentrated and recrystallised from ethyl acetate/petroleum ether (1:1).

Yield: 0.6 g (33% of theory)

Solidification point: 160°–3° C.

EXAMPLE LXIX tert-Butyl 2-[4-(2-butyl-5-carboxy-4-chloro-imidazol- 1-yl-methyl)phenyl]-2-cyclopentyl-acetate

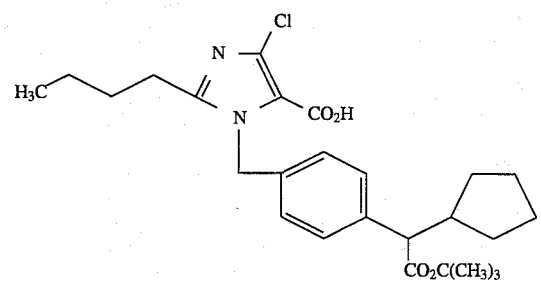

6.9 g (15 mmol) of the compound from Example I are oxidised with tetrabutylammoniumpermanganate analogously to Example XCV. The product is recrystallised from ethyl acetate/petroleum ether (1:1).

Solidification point: 75°–80° C.

Yield: 4.3 g (60.5% of theory).

EXAMPLE LXX

2-[4-(2-Butyl-5-carboxy-4-chloro-imidazol-1-yl-methyl)-phenyl]-2-cyclopentyl-acetic acid

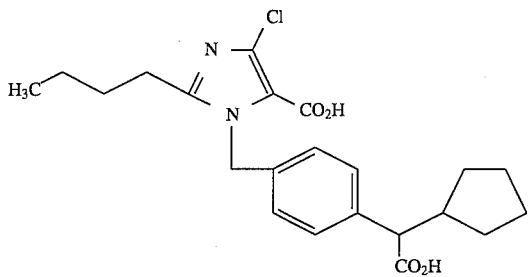

1.2 g (2.5 mmol) of the compound from Example LXIX are reacted with trifluoroacetic acid analogously to Example II. The residue is recrystallised from acetone/H₂O.
Yield: 0.85 g (81.1% of theory)
Solidification point: 196°–7° C.

EXAMPLE LXXI tert-Butyl 2-[4-(2-butyl-4-chloro-5-{N-(2-hydroxy-1(S)-phenyl-ethyl)carbamoyl}-imidazol-1-yl-methyl)phenyl]-2-cyclopentyl-acetate

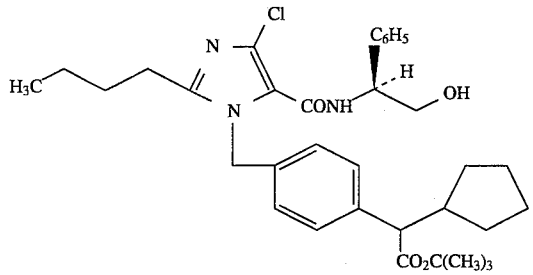

1.4 g (3 mmol) of the compound from Example LXIX are reacted with L-phenylglycinol analogously to Example V. The product is recrystallised from ethyl acetate. A 1:1 mixture of the two diastereomers is obtained.
Solidification point: 114°–8° C.
Yield: 1.3 g (73% of theory).

EXAMPLE LXXII

2-[4-(2-Butyl-4-chloro-5-{N-(2-hydroxy-1(S)-phenyl-ethyl)carbamoyl}-imidazol-1-yl-methyl)-phenyl]-2-cyclopentyl-acetic acid

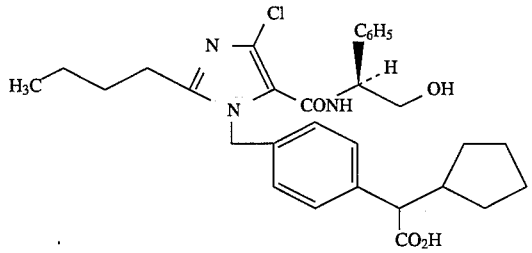

0.8 g (1.35 mmol) of the compound from Example LXXI are reacted with trifluoroacetic acid analogously to Example II. The product is recrystallised from ethanol. A 1:1 mixture of the diastereomers is obtained.
Solidification point: 183°–189° C.
Yield: 0.56 g (77.4% of theory).

EXAMPLE LXXIII

2-Butyl-4-chloro-1-(4-(1-cyclopentyl-1-tetrazol-5-yl)-methyl-benzyl)- 5-hydroxymethyl-imidazole

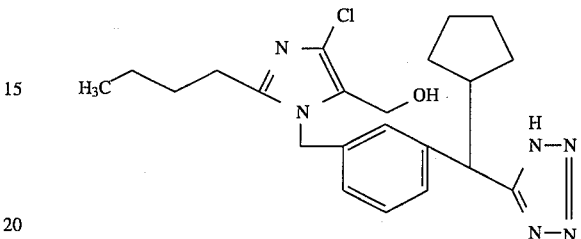

630 mg (1.04 mmol) of 2-butyl-4-chloro-1-(4-(1-cyclopentyl- 1-(2-triphenylmethyl-tetrazol-5-yl)-methyl-benzyl)-5-hydroxymethyl-imidazole are stirred (room temperature) in 5 ml of trifluoroacetic acid for 4 days. The mixture is adjusted to pH=13 with 2M sodium hydroxide solution and shaken with ether. The aqueous phase is brought to pH=5 with 1M hydrochloric acid and the precipitate obtained is filtered off with suction, washed with water and dried over phosphorus pentoxide in a high vacuum.
Yield: 217 mg
$R_f$ (dichloromethane/methanol=10:1):0.31.

EXAMPLE LXXIV

2-[3-(2-Butyl-4-chloro-5-formyl-imidazol-1-yl-methyl)-phenyl]-2-cyclopentyl-acetic acid L-phenylglycinolamide O-acetate

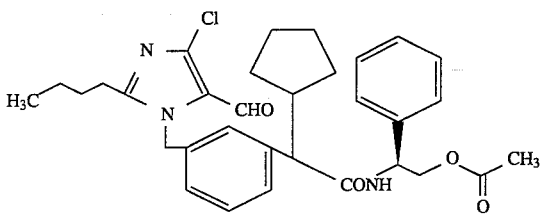

1.7 g (3.02 mmol) of 2-[3-(2-butyl-4-chloro-5-formyl-imidazol- 1-yl-methyl)phenyl]-2-cyclopentyl-acetic acid L-phenylglycinolamide are stirred at room temperature with 0.34 g (3.3 mmol) of acetic anhydride, 0.46 g (4.5 mmol) of triethylamine and 36 mg (0.3 mmol) of 4-(N,N-dimethylamino)-pyridine. After 4 h, the mixture is poured into ether/water, and the organic phase is washed with aqueous sodium hydrogen carbonate solution and 1M hydrochloric acid, dried (sodium sulphate) and evaporated. Chromatographic purification (silica gel 60, Merck, dichloromethane:methanol=100:1) yields 670 mg of product.
$R_f$ (dichloromethane/methanol=20:1):0.55.
The examples shown in Tables VII, VIII and IX are prepared in analogy to the examples mentioned therein.

TABLE VII

*[Structure: A-CH2-C6H4-CH(R)-cyclopentyl]*

| Ex. No. | A | R | R_f(*) | Preparation analogously to Example |
|---|---|---|---|---|
| LXXV | 1-methylbenzotriazol-5-yl | —CO$_2$C(CH$_3$)$_3$ | 0.23 (CH$_2$Cl$_2$) | I |
| LXXVI | 1-methylbenzotriazol-5-yl | —COOH | 0.19 C | II |
| LXXVII | 1-methylbenzotriazol-5-yl | —CONHSO$_2$-C$_6$H$_4$-CH$_3$ | 0.69 A | III |
| LXXVIII | 1-methylbenzotriazol-5-yl | —CONH-CH(C$_6$H$_5$)-CH$_2$OH | 0.36 C | V |
| LXXIX | 1-methylindazol-3-yl | —CO$_2$C(CH$_3$)$_3$ | 0.51 (M) | I |
| LXXX | 1-methylindazol-2-yl | —CO$_2$C(CH$_3$)$_3$ | 0.35 (M) | I |
| LXXXI | 1-methylindazol-3-yl | —COOH | 0.34 C | II |
| LXXXII | 1-methylindazol-3-yl | —CONH-CH(C$_6$H$_5$)-CH$_2$OH | 0.43 C | V |

TABLE VII-continued
| Ex. No. | A | R | $R_f$(*) | Preparation analogously to Example |
|---|---|---|---|---|
| LXXXIII | 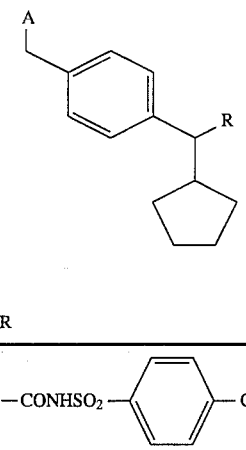 | —CONHSO$_2$—C$_6$H$_4$—CH$_3$ | 0.20 B | III |
| LXXXIV | 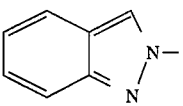 | —COOH | 0.31 C | II |
| LXXXV | 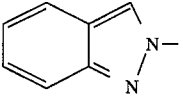 | —CONH—CH(C$_6$H$_5$)—CH$_2$OH | 0.39/0.42 C | V |
| LXXXVI | 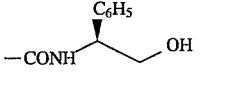 | —CONHSO$_2$—C$_6$H$_4$—CH$_3$ | 0.13 B | III |
| LXXXVII | 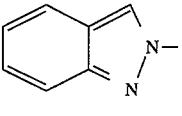 | —CO$_2$C(CH$_3$)$_3$ | 0.46 E | I |
| LXXXVIII | 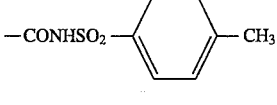 | —COOH | 0.10 E | II |
| LXXXIX | 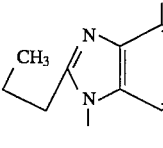 | —CONHSO$_2$—C$_6$H$_4$—CH$_3$ | 0.36 C | III |
| XC |  | —CONH—CH(C$_6$H$_5$)—CH$_2$OH | 0.10 C | V |

TABLE VIII

| Ex. No. | X | Y | $R_f$(*) | Preparation analogously to Example |
|---|---|---|---|---|
| XCI | —CHO | —CO$_2$C(CH$_3$)$_3$ | 0.25 (N) | I |
| XCII | —CHO | —COOH | 0.45 (C) | II |
| XCIII | —CH$_2$OH | —COOH | 0.21 (C) | II |
| XCIV | —CH$_2$OH | —CO$_2$C(CH$_3$)$_3$ | 0.05 (M) | IV |
| XCV | —CHO | —CONHSO$_2$—C$_6$H$_4$—CH$_3$ | 0.49 (A) | III |
| XCVI | —CHO | —CONH—CH(C$_6$H$_5$)—CH$_2$OH | 0.16 (B) | V |
| XCVII | —CH$_2$OH | —CONHSO$_2$—C$_6$H$_4$—CH$_3$ | 0.35 (C) | VI |
| XCVIII | —CH$_2$OH | —CONH—CH(C$_6$H$_5$)—CH$_2$OH | 0.23 (C) | IV |
| XCIX | —COOH | —CONHSO$_2$—C$_6$H$_4$—CH$_3$ | 0.31 (A) | XCVI |
| C | —CHO | —CONH—CH(C$_6$H$_5$)—CH$_2$OCOCH$_3$ | 0.32 (A) | XCVII |

TABLE IX

| Ex. No. | L | n | R$^3$ | $R_f$ | Preparation analogously to Example |
|---|---|---|---|---|---|
| CI | —CO$_2$CH$_3$ | 3 | —CONHSO$_2$—C$_6$H$_4$—CH$_3$ | 0,36 (C) | III |

TABLE IX-continued

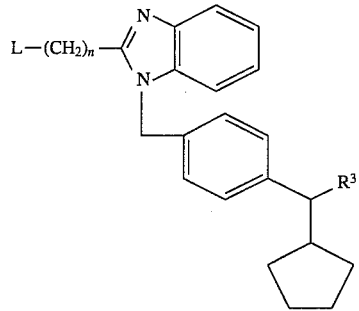

| Ex. No. | L | n | R³ | R_f | Preparation analogously to Example |
|---|---|---|---|---|---|
| CII | —CO₂CH₃ | 3 | —CONH–*(C₆H₅)*–⌒OH | 0,49 (A) | IV |

The examples shown in Table X are prepared in analogy to the procedures of Examples II and V:

TABLE X

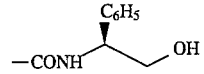

| Ex. No. | L | n | R³ | Preparation analogously to Example | MS |
|---|---|---|---|---|---|
| CIII | H₃C—CO—NH— | 3 | —CO₂H | II | (DCI): 434 (M⁺H, 100%) |
| CIV | H₃C—CO—NH— | 3 | CONH–*(C₆H₅)*–⌒OH | V (with DECI HOBt) | (FAB): 553 (M⁺H, 100%) |

The examples shown in Table XI are prepared in analogy to the examples mentioned therein:

TABLE XI

[Structure: pyrazole with R¹ substituents, N-CH₂-phenyl-CH(R³)-cyclopentyl]

| Ex. No. | R¹ | R² | R³ | Preparation analogously to Example | MS | |
|---|---|---|---|---|---|---|
| CV | H | H | COOH | II | (EI): | 248 (M⁺, 40%), 148 (100%) |
| CVI | COOCH₃ | COOCH₃ | COOH | II | (FAB): | 401 (M⁺H, 100%) |
| CVII | H₃C—(CH₂)₄— | COOH | COOH | II | (SIMS): | 505 (M⁺Ag), 421 (M⁺Na) |
| CVIII | COOCH₃ | COOCH₃ | —CONH-CH(C₆H₅)-CH₂OH | IV* (with DCC, HOBt) | (FAB): | 520 (M⁺H, 100%) |

EXAMPLE CIX

5-{1-Cyclopentyl-1-[4-(2-butyl-4-chloro-5-formyl-imidazol-1-yl-methyl)-phenyl]-methyl}-tetrazole

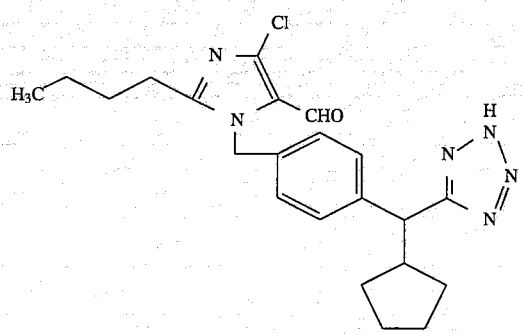

Example 26 (1.7 g; 2.5 mmol) was stirred overnight in 4N HCl/dioxane (160 ml), rendered alkaline with 1N sodium hydroxide solution and concentrated. The residue was partitioned between water and ether. The aqueous phase was rendered acidic and extracted with ether. The organic phase was dried and concentrated to give 0.89 g of a yellow oil [83.9% of theory; $R_f$ 0.29 (dichloromethane:methanol= 10:1)].

EXAMPLE CX

5-{1-Cyclopentyl-1-[4-(2-butyl-4-chloro-5-hydroxymethyl-imidazol-1-yl-methyl)-phenyl]-methyl}-tetrazole

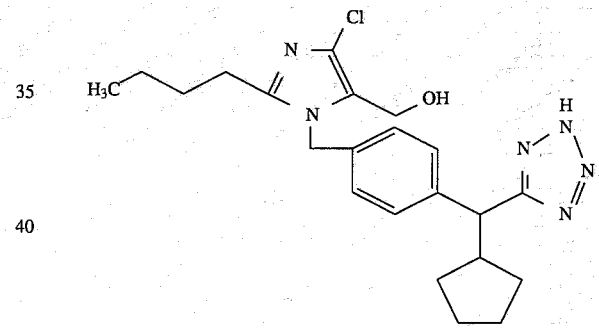

Sodium borohydride (36 mg; 0.94 mmol) was added to a solution of Example 20 (400 mg; 0.94 mmol) in methanol (100 ml) and the mixture was stirred overnight. To complete the reaction, the solution was concentrated to 5 ml, the same amount of sodium borohydride was added and the mixture was stirred overnight. After concentration, 1M KHSO₄ solution was added to the residue and the mixture was extracted with ethyl acetate. The organic phase was dried, concentrated and purified by means of HPLC (Licroprep RP18, 35–80% acetonitrile/water/0.05% trifluoroacetic acid) to give 72 mg of a white solid (18% of theory).

EXAMPLE CXI 2,2-Dicyclopentyl-2-[4-(2-butyl-4-chloro-5-formyl-imidazol-1-yl-methyl)-phenyl]-acetonitrile

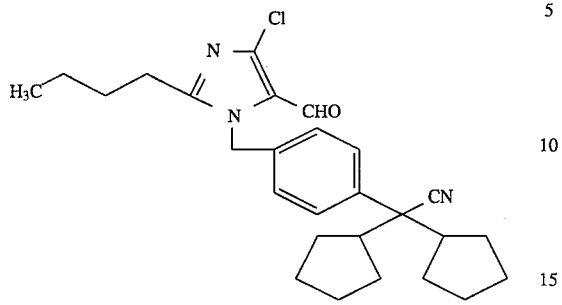

Alkylation using Example 27 (0.93 g; 2.7 mmol) analogously to Example 26 and silica gel chromatography (toluene/ethyl acetate step gradient) gave 1.3 g of a yellow oil [54% of theory; $R_f$ 0.57 (toluene:ethyl acetate=5:1)].

EXAMPLE CXII 2,2-Dicyclopentyl-2-[4-(2-butyl-4-chloro-5-hydroxymethyl-imidazol-1-yl-methyl)-phenyl]-acetonitrile

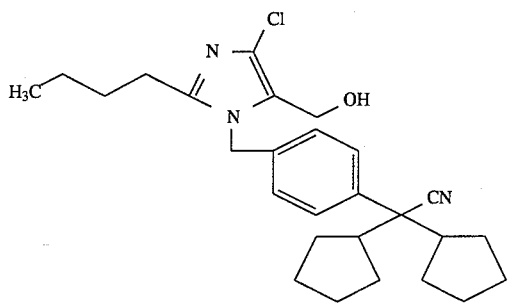

1M diisobutylaluminium hydride/tetrahydrofuran (0.48 ml) was added dropwise at 10° C. under argon to a solution of Example XCI (100 mg; 0.22 mmol) in toluene (4 ml) and the mixture was stirred at room temperature overnight. After addition of water (0.5 ml), the emulsion was added to intensively stirred 5% strength sulphuric acid, adjusted to pH 7 and extracted with ether. Drying and concentration of the organic phase, followed by silica gel chromatography (methylene chloride:methanol=20:1) yielded 58 mg of an oil [59% of theory; $R_f$ 0.44 (methylene chloride:methanol=20:1)].

EXAMPLE CXIII tert-Butyl 2-{4-[2-butyl-4-chloro-5-(1-hydroxy)-ethyl-imidazol-1-yl-methyl]-phenyl}-2-cyclopentyl-acetate

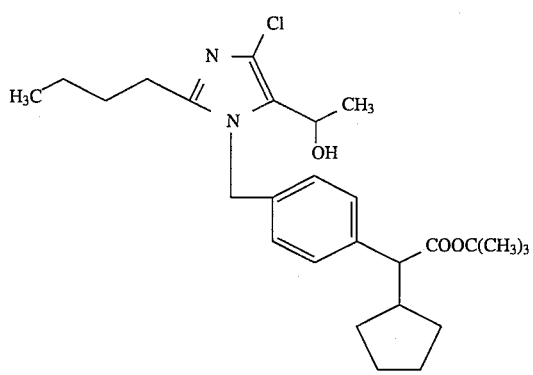

3M MeMgCl/THF (0.18 ml; 0.55 mmol) was added under argon at −78° C. to a solution of Example I (230 mg; 0.50 mmol) in tetrahydrofuran (5 ml) and the mixture was stirred overnight at room temperature. After concentration, the residue was taken up in ethyl acetate, washed twice with 5% $Na_2CO_3$ solution, then with saturated sodium chloride solution, dried and concentrated to obtain 206 mg of an oil [93.9% of theory; $R_f$ 0.10 (methylene chloride:ethyl acetate=10:1)].

EXAMPLE CXIV

2-{4-[2-Butyl-4-chloro-5-(1-hydroxy)-ethyl-imidazol-1-yl-methyl]-phenyl}-2-cyclopentyl-acetic acid

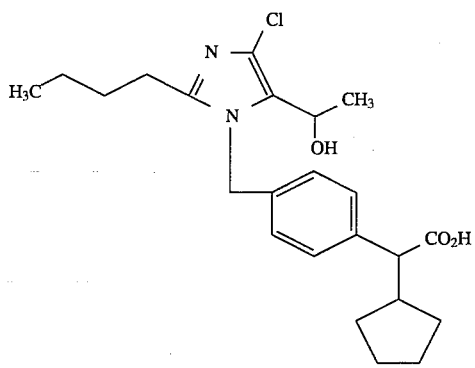

A solution of Example CXIII (356 mg; 0.38 mmol) in dichloromethane (10 ml) and trifluoroacetic acid (10 ml) was kept at room temperature for 1.5 h and then concentrated. Water was added to the residue, and the mixture was adjusted to pH 3 with saturated sodium hydrogen carbonate solution and extracted with ether. Drying, concentration and silica gel chromatography (methylene chloride:methanol=20:1) yielded 97 mg of a colourless, amorphous substance [29% of theory; $R_f$ 0.33 (methylene chloride:methanol:acetic acid=20:1:0.1)].

EXAMPLE CXV

N-4-Tolylsulphonyl-2-{4-[2-butyl-4-chloro-5-(1-hydroxy)-ethyl-imidazol- 1-yl-methyl]-phenyl}-2-cyclopentyl-acetamide

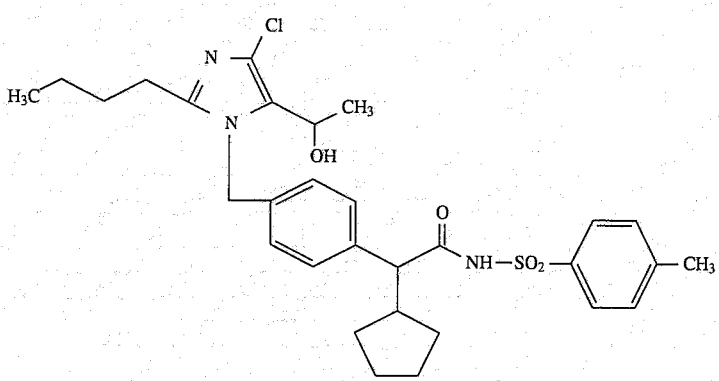

80% sodium hydride/paraffin oil dispersion (6.0 mg; 0.2 mmol) was added at 0° C. under argon to a solution of Example III (100 mg; 0.18 mmol) in THF (5 ml), the mixture was stirred at room temperature for 15 min, 3M MeMgCl/THF (0.1 ml) was then added at 0° C. and the mixture was stirred at room temperature for 40 h. The reaction solution was acidified to pH 3 with 1M KHSO$_4$ solution and extracted three times with ethyl acetate. The organic phases were washed with saturated sodium chloride solution, dried and concentrated. Silica gel chromatography yielded 36 mg of a partly solid substance [36% of theory; R$_f$ 0.25 (methylene chloride:methanol:conc. ammonia water= 10:1:0.1)].

EXAMPLE CXVI

2-{4-[2-Butyl-4-chloro-5-(1-hydroxy)-propyl-imidazol-1-yl-methyl]-phenyl}-2-cyclopentyl-acetic acid

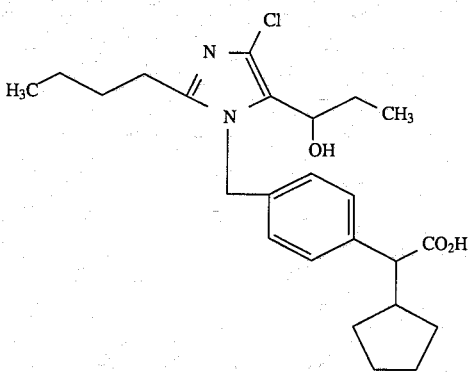

3M ethylmagnesium bromide/ether (2.1 ml) was added dropwise under argon at −20° C. to a solution of Example II (1.13 g; 1.2 mmol) in THF (10 ml) (until starting material was no longer present according to TLC). After addition of 1M KHSO$_4$ solution, the mixture was extracted with ethyl acetate. The organic phase was dried, concentrated, purified using HPLC (Licrosorp RP18, 40–90% acetonitrile/water/ 0.05% trifluoroacetic acid) to give 189 mg of a white solid [36% of theory; R$_f$ 0.50 (methylene chloride:ethyl acetate:acetic acid=5:2:0.1)].

EXAMPLE CXVII

2-{4-[2-Butyl-4-chloro-5-(1-propen-1-yl)-imidazol-1-yl-methyl]-phenyl}-2-cyclopentyl-acetic acid

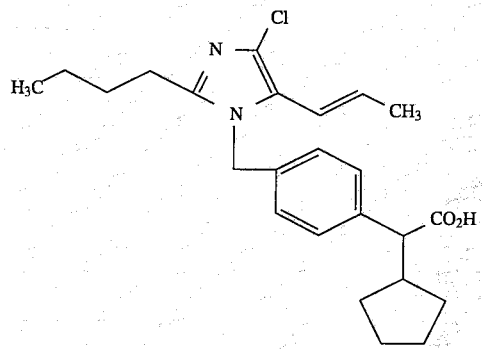

The HPLC purification of Example CXVI yielded 19 mg of a white solid (3.8% of theory) as a non-polar by-product.

EXAMPLE CXVIII

2-{4-[2-Butyl-4-chloro-5-(1-hydroxy)-isobutyl-imidazol-1-yl-methyl]-phenyl}-2-cyclopentyl-acetic acid

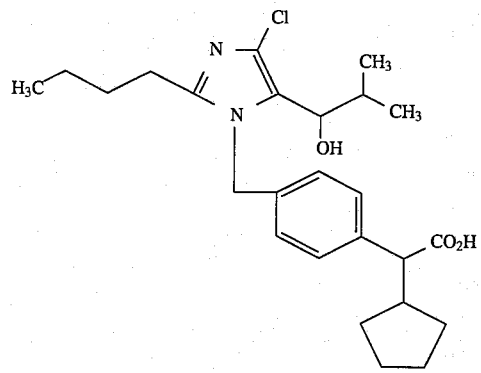

Analogously to Example CXVII 113 mg of a white solid (21% of theory; R$_f$ 0.50) were obtained from Example II (1.13 g crude; 1.2 mmol) using isopropylmagnesium chloride.

EXAMPLE CXIX

2-{4-[2-Butyl-4-chloro-5-(1-hydroxy)-neopentyl-imidazol-1-yl-methyl]-phenyl}-2-cyclopentyl-acetic acid

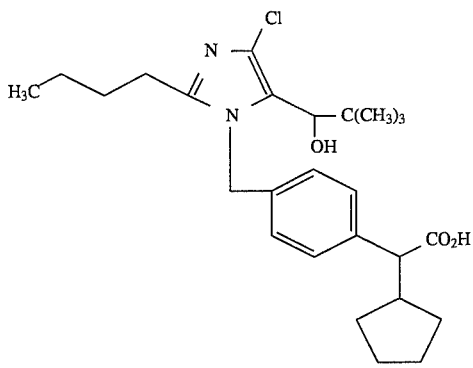

Analogously to Example CXVII 68 mg of a white solid (12% of theory; $R_f$ 0.50) were obtained from Example II (1.13 g crude; 1.2 mmol) using tert-butylmagnesium chloride.

EXAMPLE CXX tert-Butyl 2-{4-[2-(1-bromo-butyl)-4-chloro-5-formyl-imidazol-1-yl-methyl]-phenyl}-2-cyclopentyl-acetate

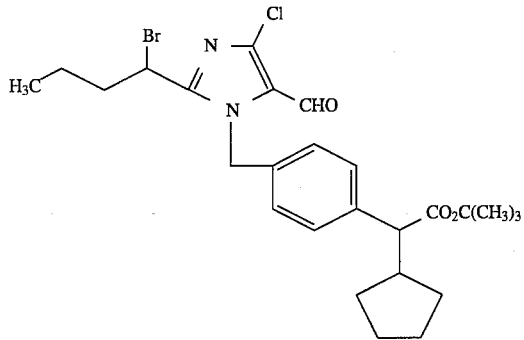

Analogously to Example 24, 7.7 g of a yellow oil [43% of theory; $R_f$ 0.46 (methylene chloride)] were obtained from Example I (15 g; 33 mmol) after silica gel chromatography (hexane:ethyl acetate=5:1).

EXAMPLE CXXI tert-Butyl 2-{4-[2-(1-buten-1-yl)-4-chloro-5-formyl-imidazol-1-yl-methyl]-phenyl}-2-cyclopentyl-acetate

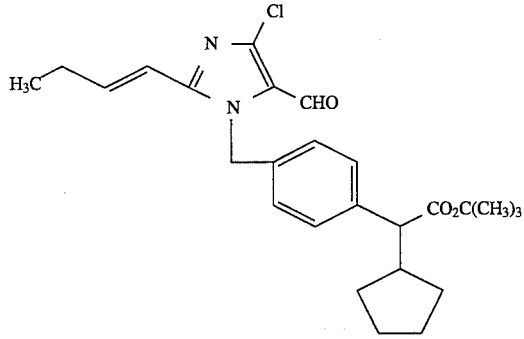

DBU (5.3 ml; 35 mmol) was added to a solution of Example CXX (7.7 g; 14 mmol) in THF (250 ml) and the mixture was allowed to stand for 3 d. After addition of water and extraction with ether, the organic phase was washed with dilute hydrochloric acid, dried and concentrated. Silica gel chromatography of the residue (methylene chloride) gave 4.4 g of an oil (67% of theory; $R_f$ 0.2).

EXAMPLE CXXII

2-{4-[2-(1-Buten-1-yl)-4-chloro-5-formyl-imidazol-1-yl-methyl]-phenyl}-2-cyclopentyl-acetic acid

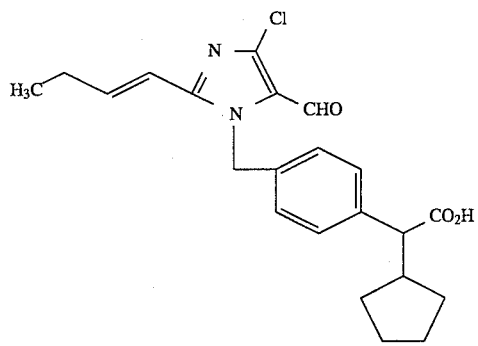

Ester cleavage of Example CXXI (4.6 g; 9.6 mmol) analogously to Example CXIII gave 3.5 g of a yellow oil [91% of theory; $R_f$ 0.40 (methylene chloride:methanol= 20:1)].

EXAMPLE CXXIII

2-{4-[2-(1-Buten-1-yl)-4-chloro-5-hydroxymethyl-imidazol-1-yl-methyl]-phenyl}-2-cyclopentyl-acetic acid

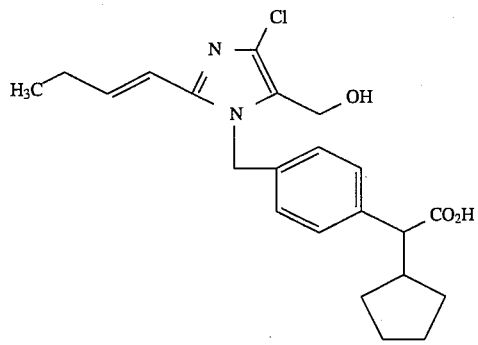

Reduction of Example CXXI (68 mg; 0.17 mmol) analogously to Example CIX and silica gel chromatography (methylene chloride:methanol=20:1) gave 30 mg of a white solid (44% of theory; $R_f$ 0.18).

EXAMPLE CXXIV

N-4-Tolylsulphonic acid-2-{4-[2-(1-buten-1-yl)-4-chloro-5-formyl-imidazol-1-yl-methyl]-phenyl}-2-cyclopentyl-acetamide

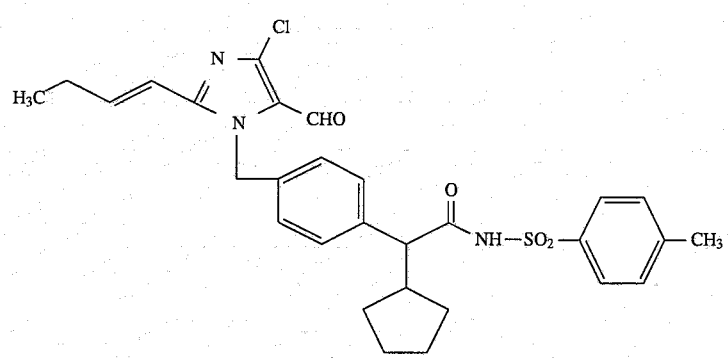

A few drops of DBU and tosyl isocyanate (0.62 ml; 4.1 mmol) were added to a solution of Example CXXIII (1.5 g; 3.7 mmol) and the mixture was boiled under reflux overnight. Concentration and silica gel chromatography (methylene chloride:methanol:conc. ammonia water=20:1:0.1) gave 1.5 g of a yellowish solid [72% of theory; m.p. 99° C.; $R_f$ 0.39 (methylene chloride:methanol:conc. ammonia water=10:1:0.1)].

EXAMPLE CXXV tert-Butyl 2-[4-(2-butyl-5-formyl-4-iodo-imidazol-1-yl-methyl)-phenyl]-2-cyclopentyl-acetate

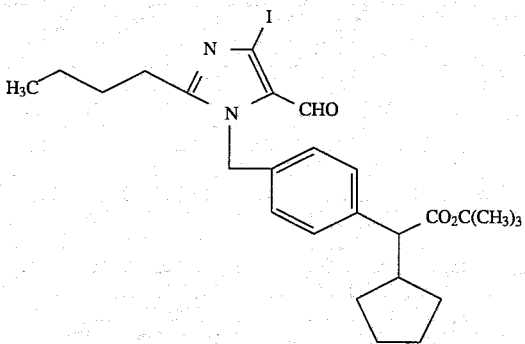

Coupling of Example 29 (9.3 g; 33 mmol) with Example 3 (11.8 g; 33 mmol) analogously to Example 26 gave, after silica gel chromatography (petroleum ether:methylene chloride=1:1), 12.7 g of a yellow solid [70% of theory; m.p. 95°–7° C.; $R_f$ 0.18 (methylene chloride)].

EXAMPLE CXXVI

2-[4-(2-Butyl-5-formyl-4-iodo-imidazol-1-yl-methyl)-phenyl]-2-cyclopentyl-acetic acid

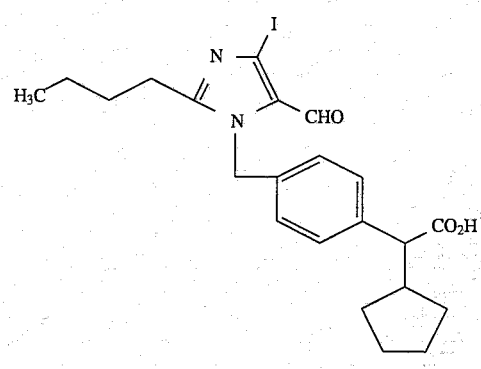

Ester cleavage of Example CXXV (3.4 g; 6.2 mmol) analogously to Example CXXIV gave 3.15 g of a yellow resin [theory: 3.05 g; $R_f$ 0.21 (methylene chloride:methanol:conc. ammonia water=10:1:0.1)].

EXAMPLE CXXVII

N-4-Tolylsulphonic acid-2-[4-(2-butyl-5-formyl-4-iodo-imidazol- 1-yl-methyl)-phenyl]-2-cyclopentyl-acetamide

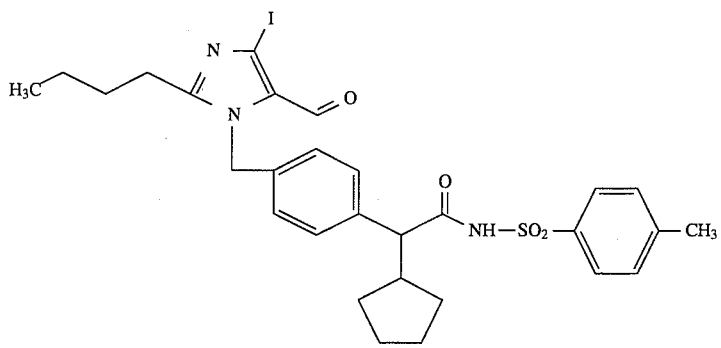

Reaction of Example CXXVI (2.55 g; 5.16 mmol) analogously to Example CXXIII gave, after silica gel chromatography (methylene chloride:methanol:conc. ammonia water=20:1:0.1), 2.32 g of a solid foam [69% of theory; $R_f$ 0.40 (methylene chloride:methanol:conc. ammonia water= 10:1:0.1)].

EXAMPLE CXXVIII

N-4-Tolylsulphonic acid-2-[4-butyl-5-hydroxymethyl-4-iodo-imidazol-1-yl-methyl)-phenyl]-2-cyclopentyl-acetamide

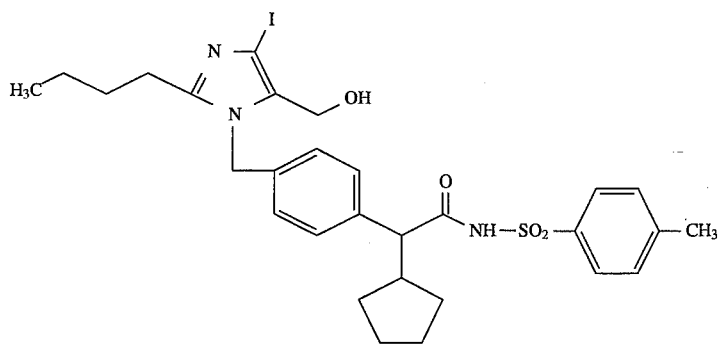

Reduction of Example CXXVII (1.3 g; 2.0 mmol) analogously to Example CIX gave, after silica gel chromatography (methylene chloride:methanol=20:1), 1.1 g of a white solid (85% of theory; $R_f$ 0.19).

EXAMPLE CXXIX tert-Butyl 2-[4-(2-butyl-5-hydroxymethyl-4-iodo-imidazol-1-yl-methyl)-phenyl]-2-cyclopentyl-acetate

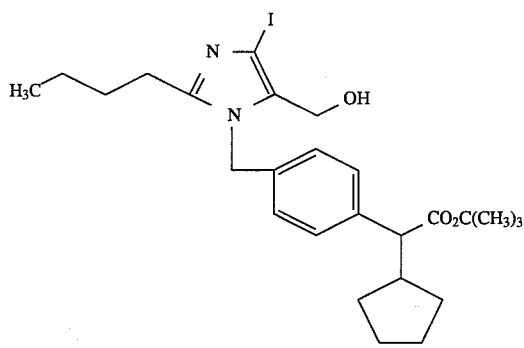

Reduction of Example CXXV (5.4 g; 9.8 mmol) analogously to Example CIX gave, after silica gel chromatography (methylene chloride:methanol=20:1), 4.3 g of an oil (80% of theory; $R_f$ 0.34).

EXAMPLE CXXX tert-Butyl 2-[4-{2-butyl-5-[(2-methoxy)ethoxy-methoxy-methyl]-4-iodo-imidazol-1-yl-methyl}-phenyl}-2-cyclopentyl-acetate

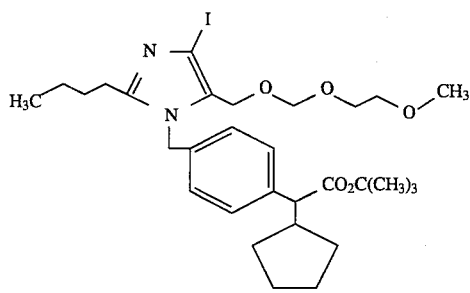

A solution of Example CXXIX (3.94 g; 7.13 mmol) in THF (100 ml) was added dropwise under argon at −5° C. to a suspension of 80% sodium hydride/paraffin oil (4.71 mg; 15.7 mmol) in THF (10 ml). After stirring at 0° C. for 15 min, 2-methoxy-ethoxy-methyl chloride (1.8 ml; 15.7 mmol) was added dropwise at −5° C. After 2 h at room temperature and 2 h at 50° C., the reaction mixture was concentrated, partitioned between ether and water and adjusted to pH 8–9 with NaHCO₃. The aqueous phase was extracted four times with ether, and the combined organic phases were washed with saturated sodium chloride solution, dried and concentrated. Silica gel chromatography (methylene chloride:methanol—step gradient) yielded 2.15 g of an oil [47% of theory; $R_f$ 0.54 (methylene chloride:methanol=20:1)].

EXAMPLE CXXXI tert-Butyl 2-{4-{2-butyl-5-[(2-methoxy)ethoxy-methoxy-methyl]-trifluoromethyl-imidazol-1-yl-methyl}-phenyl}-2-cyclopentyl-acetate

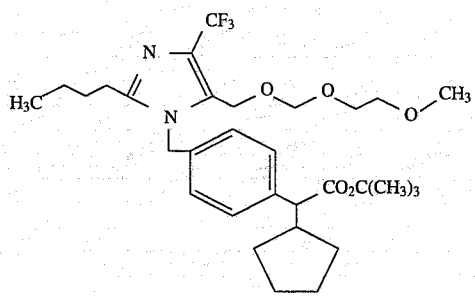

Dibromodifluoromethane (8.6 ml; 94 mmol; dry ice condenser) was slowly added dropwise under argon to a suspension of cadmium powder (22.4 g; 0.200 g atom) in DMF (50 ml). After stirring for 2 h, the suspension was filtered under argon through a Schlenck frit to give a brown, about 1.6M bistrifluoromethylcadmium/DMF stock solution.

Copper(I) bromide (3.78 g; 26.4 mmol) and Example CXXX (4.64 g; 7.2 mmol) were added under argon to a solution of 1.6M bistrifluoromethylcadmium/DMF (27 ml) and HMPT (36 ml). After stirring at 75° C. for 8 h, water (100 ml) and methylene chloride (500 ml) were added. The precipitate was filtered off, and the organic phase was separated off and concentrated. The residue was dissolved in ethyl acetate (500 ml) and petroleum ether (500 ml), washed five times with water, dried and concentrated. Silica gel chromatography (methylene chloride/methanol—step gradient) gave 3.75 g of an oil (89% of theory; $R_f$ 0.45 (hexane:ethyl acetate=2:1)].

EXAMPLE CXXXII

2-{4-{2-Butyl-5-[(2-methoxy)ethoxy-methoxy-methyl]-4-trifluoromethyl-imidazol-1-yl-methyl}-phenyl}-2-cyclopentyl-acetic acid

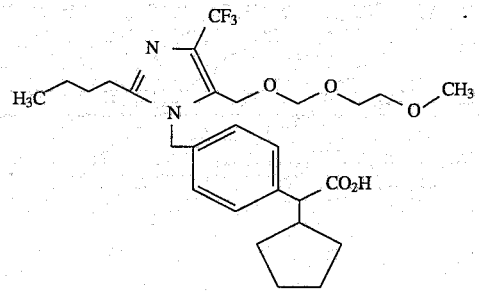

Trifluoroacetic acid (40 ml) was added at 0° C. to a solution of Example CXXXI (3.73 g; 6.48 mmol) in methylene chloride (40 ml) and the mixture was stirred at room temperature for 3 h. After concentration, the residue was taken up in 100 ml of ethyl acetate and adjusted to pH 7 with 5% $NaHCO_3$ solution. The aqueous phase was extracted four times with ethyl acetate, and the combined organic phases were washed with saturated sodium chloride solution, dried and concentrated to give 2.65 g of an oil. Rendering the combined aqueous phases alkaline with $Na_2CO_3$ solution and ethyl acetate extraction yielded a further 0.32 g [87% of theory; $R_f$ 0.40 (methylene chloride:methanol=20:1)].

EXAMPLE CXXXIII

2-[4-(2-Butyl-5-hydroxymethyl-4-trifluoromethyl-imidazol-1-yl-methyl)-phenyl]-2-cyclopentyl-acetic acid

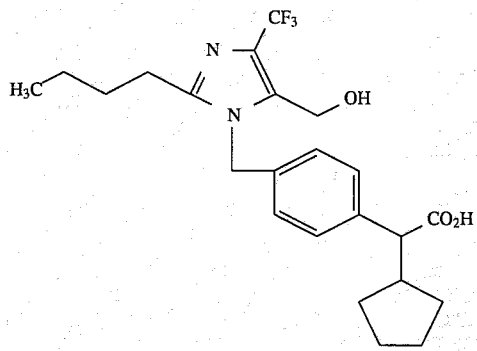

4N HCl/dioxane (5 ml) and water (10 ml) were added to a solution of Example CXXXII (160 mg; 0.304 mmol) in dioxane (5 ml) and the mixture was stirred for 1 h. After concentration, the pH was adjusted to 7 with 5% $NaHCO_3$ solution, and the solution was extracted five times with ethyl acetate. The combined organic phases were washed with saturated sodium chloride solution, dried and concentrated to give 141 mg of an oil [theory: 133 mg; $R_f$ 0.24 (methylene chloride:methanol=20:1)].

EXAMPLE CXXXIV

N-4-Tolylsulphonic acid-2-{4-{2-butyl-5-[(2-methoxy)-ethoxy-methoxy-methyl]-4 -trifluoromethyl-imidazol-1-yl-methyl}-phenyl}-2-cyclopentyl-acetamide

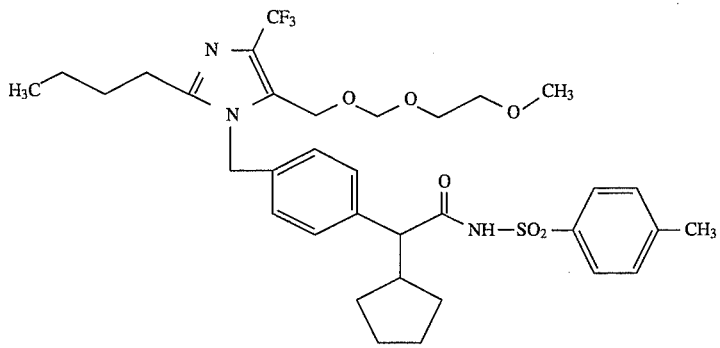

Example CXXXII (650 mg; 1.23 mmol) was reacted analogously to Example CXXVII Silica gel chromatography (hexane/ethyl acetate 4:1 to 2:1, then methylene chloride/ methanol 50:1 to 12.5:1) gave 410 mg of an oil [49% of theory; $R_f$ 0.35 (hexane:ethyl acetate=1:1)].

EXAMPLE CXXXV

N-4-Tolylsulphonic acid-2-[4-(2-butyl-5-hydroxymethyl-4-trifluoromethyl-imidazol-1-yl-methyl)-phenyl]-2-cyclopentyl-acetamide

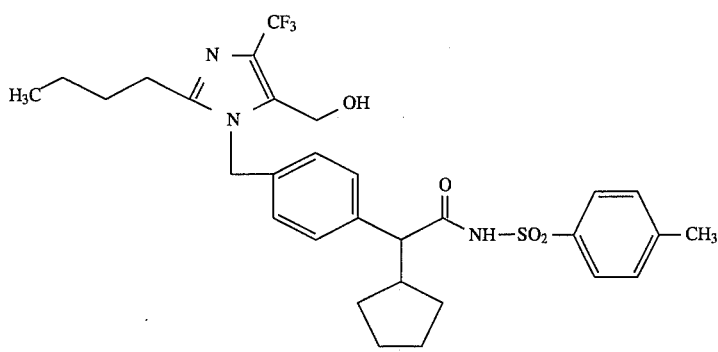

Example CXXXIV (200 mg; 0. 294 mmol) were deprotected analogously to Example CXXXIII to give 160 mg of an oil [92% of theory; $R_f$ 0.41 (methylene chloride:methanol=20:1)].

EXAMPLE CXXXVI tert-Butyl 2-[4-(5-acetoxymethyl-2-butyl-4-iodo-imidazol-1-yl-methyl)-phenyl]-2-cyclopentyl-acetate

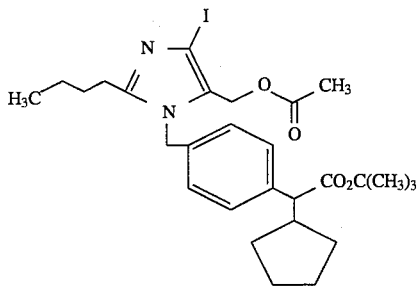

4-DMAP (0.21 g; 1.7 mmol) was added to a solution of Example CXXIX (9.5 g; 17 mmol) in pyridine (20 ml) and acetic anhydride (20 ml) and the mixture was stirred at room temperature overnight and then at 50° C. for 2 h. The reaction mixture was concentrated, adjusted to pH 3 with 1M KHSO$_4$ solution and extracted with ethyl acetate. Drying and concentration of the organic phases and silica gel chromatography (methylene chloride) yielded 9.2 g of a yellow oil (93% of theory; $R_f$ 0.34).

EXAMPLE CXXXVII tert-Butyl 2-[4-(5-acetoxymethyl-2-butyl-4-perfluorobutyl-imidazol- 1-yl-methyl)-phenyl]-2-cyclopentyl-acetate

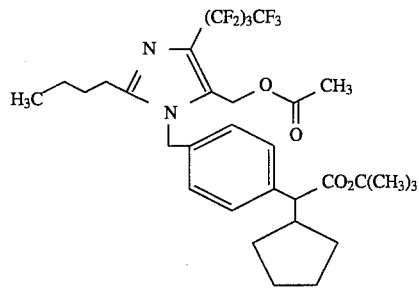

Perfluorobutyl iodide (12.9 ml; 75 mmol; dry ice condenser) was slowly added dropwise under argon to a suspension of cadmium powder (12.3 g; 0.110 g atom) in DMF (100 ml). After stirring at room temperature for 2 h and at 35° C. for 1 h, the suspension was filtered under argon through a Schlenck frit.

Copper(I) bromide (1.5 g; 11 mmol) and a solution of Example CXXXVI (886 mg; 1.49 mmol) in DMF (10 ml) were added under argon to bisperfluorobutylcadmium/DMF solution (15 ml) and HMPT (7 ml). After stirring at 75° C. for 6 h, water (100 ml) and methylene chloride (500 ml) were added. The precipitate was filtered off, and the organic phase was separated off and concentrated. The residue was dissolved in ethyl acetate/petroleumether (1:1), washed five times with water, dried and concentrated. Silica gel chromatography (methylene chloride:methanol=1:1) gave 235 mg of an oil (23% of theory; $R_f$ 0.48 (hexane:ethyl acetate= 3:1)].

EXAMPLE CXXXVIII

2-[4-(5-Acetoxymethyl-2-butyl-4-perfluorobutyl-imidazol-1-yl-methyl)-phenyl]-2-cyclopentyl-acetic acid

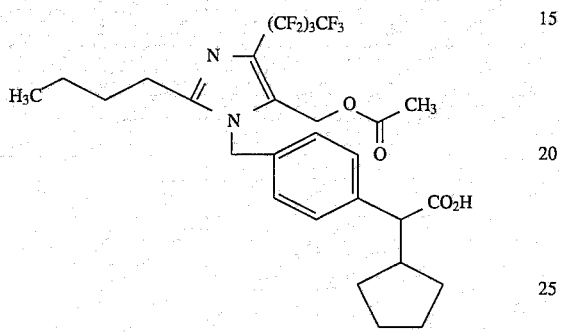

Ester cleavage of Example CXXXVII analogously to Example CXXXII led to 172 mg of an oil [96% of theory; $R_f$ 0.34 (methylene chloride:methanol=20:1)].

EXAMPLE CXXXIX

N-4-Tolylsulphonic acid-2-{4-[2-(1-buten-1-yl)-4-chloro-5-hydroxymethyl-imidazol-1-yl-methyl]-phenyl}-2-cyclopentyl-acetamide

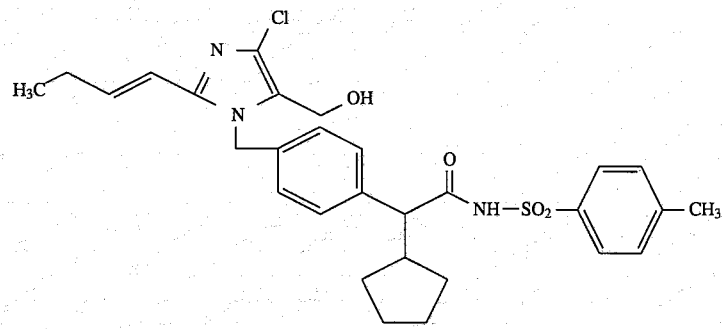

Reduction of Example CXXIV (0.50 g; 0.90 mmol) analogously to Example CX and silica gel chromatography (methylene chloride:methanol=20:1) gave 322 mg of a white solid (64% of theory; m.p. 116°–8° C.; $R_f$ 0.25).

The compounds shown in Tables XII to XV are prepared in analogy to the procedures indicated therein.

TABLE XII

Structure: 2-butyl-4-chloro-5-formyl-1-[[4-(CR¹R²-CO₂H)phenyl]methyl]imidazole

| Ex. No. | R¹ | R² | * | Preparation analogously to Example | R_f (eluent) */m.p. °C. |
|---|---|---|---|---|---|
| CXL | H | H | — | 11 | 0.43 F |
| CXLI | —CH₃ | —CH₃ | — | 11/II | 132 |
| CXLII | H | —(CH₂)₃CH₃ | rac | II | 72 |
| CXLIII | H | cyclohexyl (6) | rac | II | 153 |
| CXLIV | H | cycloheptyl (7) | rac | II | 135 |
| CXLV | H | —CH₂—C₆H₅ | rac | II | 0.49 O |
| CXLVI | H | —(CH₂)₄—CH₃ | rac | II | 0.30 P |
| CXLVII | H | —(CH₂)₅—CH₃ | rac | II | 0.56 P |
| CXLVIII | H | —(CH₂)₂—CH(CH₃)₂ | rac | II | 0.67 F |

TABLE XIII

Structure: 2-butyl-4-chloro-5-hydroxymethyl-1-[[4-(CR¹R²-CO₂H)phenyl]methyl]imidazole

| Ex. No. | R¹ | R² | * | Preparation analogously to Example | R_f (eluent) */m.p. °C. |
|---|---|---|---|---|---|
| CXLIX | H | H | — | 12/IV | 0.48 |
| CL | —CH₃ | —CH₃ | — | 11/IV | 163 |
| CLI | H | —(CH₂)₃CH₃ | rac | IV | 0.74 O |

TABLE XIII-continued

[Structure: chloro-imidazole derivative with N-CH2-phenyl-CHR1R2-CO2H substituent, 2-butyl group, and hydroxymethyl]

| Ex. No. | R¹ | R² | * | Preparation analogously to Example | $R_f$ (eluent) */m.p. °C. |
|---|---|---|---|---|---|
| CLII | H | cyclohexyl | rac | IV | 0.46P |
| CLIII | H | cycloheptyl | rac | IV | 186 |
| CLIV | H | -CH₂-C₆H₅ (benzyl-ethyl) | rac | IV | 0.49F |
| CLV | H | —(CH₂)₄—CH₃ | rac | IV | 0.26F |
| CLVI | H | —(CH₂)₅—CH₃ | rac | IV | 0.26F |
| CLVII | H | —(CH₂)₂—CH(CH₃)₂ | rac | IV | 0.30F |

TABLE XIV

[Structure: 4-chloro-2-butyl-5-hydroxymethyl-imidazole with N-CH2-phenyl-CHR1R2-C(O)-NH-CH(phenyl)-CH2OH substituent]

| Ex. No. | R¹ | R² | * | Preparation analogously to Example | $R_f$ (eluent) */m.p. °C. |
|---|---|---|---|---|---|
| CLVIII I | H | H | S | 12/IV | 0.37 F |
| CLIX | —CH₃ | —CH₃ | S | 11/IV | 0.26 H |
| CLX | H | —(CH₂)₃CH₃ | dia | IV | 92 |
| CLXI | H | cyclohexyl | dia | IV | 0.77 F |

TABLE XIV-continued

[Structure: imidazole with Cl, CH2OH substituents, N-butyl, N-benzyl linked to phenyl-CHR1R2-C(O)NH-CH(phenyl)-CH2OH]

| Ex. No. | R¹ | R² | * | Preparation analogously to Example | $R_f$ (eluent) */m.p. °C. |
|---|---|---|---|---|---|
| CLXII | H | cycloheptyl | dia A | IV | 102 |
| CLXIII | H | cycloheptyl | dia B | IV | 105 |
| CLXIV | H | -CH₂-phenyl | dia | IV | 0.18/0.27 I |
| CLXV | H | —(CH₂)₄—CH₃ | dia | IV | 0.49F |
| CLXVI | H | —(CH₂)₅—CH₃ | dia | IV | 0.54F |

TABLE XV

[Structure: imidazole with Cl, CHO substituents, N-butyl, N-benzyl linked to phenyl-CHR1R2-C(O)NH-CH(phenyl)-CH2OH]

| Ex. No. | R¹ | R² | * | Preparation analogously to Example | $R_f$ (eluent) */m.p. °C. |
|---|---|---|---|---|---|
| CLXVII | H | H | S | 12 | 0.54F |
| CLXVIII | —CH₃ | —CH₃ | S | 11/V | 0.45F |
| CLXIX | H | —(CH₂)₃CH₃ | dia | V | 65 |
| CLXX | H | cyclohexyl | dia | V | 79 |
| CLXXI | H | cycloheptyl | dia | V | 84 |

TABLE XV-continued

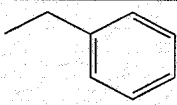

| Ex. No. | R[1] | R[2] | * | Preparation analogously to Example | $R_f$ (eluent) */m.p. °C. |
|---|---|---|---|---|---|
| CLXXII | H | (CH₂-phenyl) | dia | V | 0.6 F |
| CLXXIII | H | $-(CH_2)_4-CH_3$ | dia | V | 0.60F |
| CLXXIV | H | $-(CH_2)_5-CH_3$ | dia | V | 0.68F |

EXAMPLE CLXXV

N-(2-acetoxy-1,S-phenyl-ethyl)-2-[4-(2-Butyl-4-chloro-5-carboxy-imidazol-1-yl-methyl)phenyl]-2-cyclopentyl-acetamide

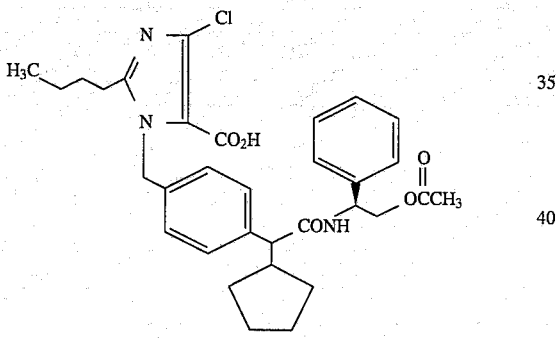

564 mg of N-(2-acetoxy-1,S-phenyl-ethyl)-2-[4-(2-butyl-4-chloro-5-formyl-imidazol-1-yl-methyl)phenyl]-2-cyclopentylacetamide are dissolved in 6 ml of tert-butanol, and 4 ml of 1.25M aqueous $NaH_2PO_4$ solution (pH 7) and then 6 ml of 1M $KMnO_4$ solution (aqueous) are added. After stirring for 10 minutes, 6 ml of saturated $Na_2SO_3$ solution are added in an ice bath, and the solution is brought to pH 3 with 1M HCl. After extracting three times with ethyl acetate, the organic phase is dried over $Na_2SO_4$, filtered and concentrated.

Yield: 340 mg (63% of theory).

EXAMPLE CLXXVI

N-(2-Hydroxy-1,S-phenyl-ethyl)-2-[4-(2-butyl-4-chloro-5-carboxy-imidazol-1-yl-methyl)-phenyl]-2-cyclopentyl-acetamide

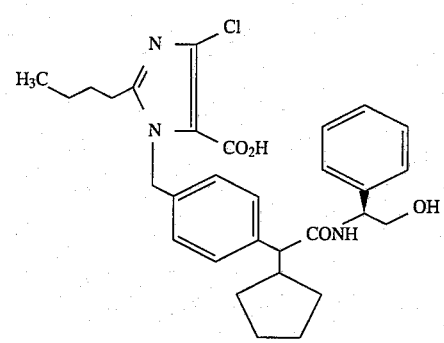

200 mg of N-(2-acetoxy-1,S-phenyl-ethyl)2-[4-(2-butyl-4-chloro-5-carboxy-imidazol-1-yl-methyl)phenyl-2-cyclopentyl-acetamide are dissolved in 1.2 ml of dioxane/0.8 ml of $H_2O$ and 44 mg of LiOH dissolved in 0.3 ml of $H_2O$ are added. After stirring overnight, the mixture is washed with ether, brought to pH 4 (1N HOAc) and extracted three times with ethyl acetate. The combined ethyl acetate phases are dried over $Na_2SO_4$, filtered and concentrated.

Yield: 179 mg (95% of theory).

The examples shown in Table XVI are prepared in analogy to the procedure of Example II.
TABLE XVI
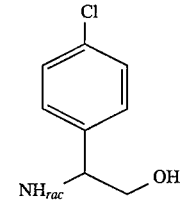
| Ex. No. | R | * | $R_f$ (eluent)* |
|---|---|---|---|
| CLXXVII | 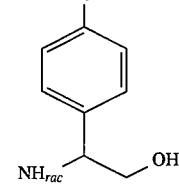 | dia A (rac) | 0.45 I |
| CLXXVIII | 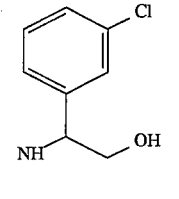 | dia B (rac) | 0.36 I |
| CLXXIX | 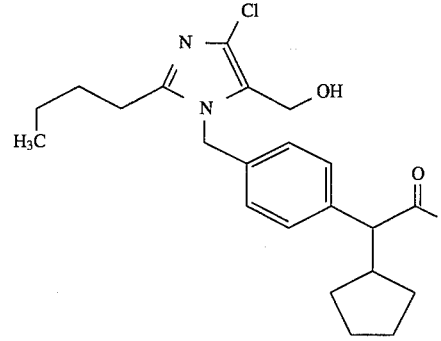 | dia (rac) | 0.50/0.47 F |
TABLE XVI-continued
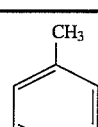
| Ex. No. | R | * | $R_f$ (eluent)* |
|---|---|---|---|
| CLXXX | 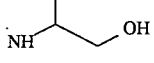 | dia (rac) | 0.39/0.30 H |
| CLXXXI | 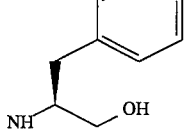 | dia | 0.28 I |
| CLXXXII | 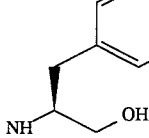 | dia | 0.11 I |

TABLE XVII
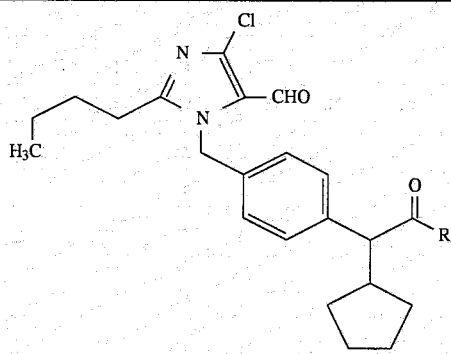
| Ex. No. | R | * | Preparation analogous to Ex. | $R_f$ (eluent)* |
|---|---|---|---|---|
| CLXXXIII(a) | 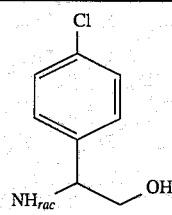 | 4 dia | V | 0.62 I |
| CLXXXIV | 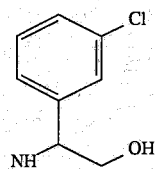 | 4 dai | V | 0.52 F |
| CLXXXV | 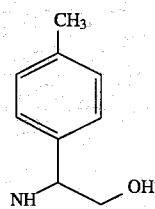 | 4 dia | V | 0.81 F |
| CLXXXVI | 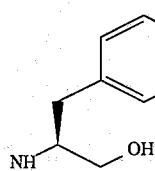 | 2 dia/ent | V | 0.73 F |
| CLXXXVII | 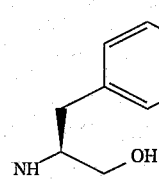 | 2 dia/ent | V | 0.47 F |

TABLE XVIII

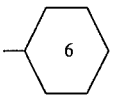

| Ex. No. | R¹ | R² | * | Preparation analogously to Example | $R_f$ (eluent)*/ m.p. °C. |
|---|---|---|---|---|---|
| CLXXXVIII | H | H | — | β/IV | 0.52 F |
| CLXXXIX | —CH₃ | —CH₃ | — | α/IV | 184 |
| CXC | H | —(CH₂)₃CH₃ | rac | IV | 125 |
| CXCI | H | cyclohexyl | rac | IV | 123 |
| CXCII | H | cycloheptyl | rac | IV | 103–106 |
| CXCIII | H | —CH₂—C₆H₅ | rac | IV | 0.57 F |
| CXCIV | H | —(CH₂)₄—CH₃ | rac | IV | 0.49 F |
| CXCV | H | —(CH₂)₅—CH₃ | rac | IV | 0.51 F |

TABLE XIX

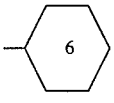

| Ex. No. | R¹ | R² | * | Preparation analogously to Example | $R_f$ (eluent)*/ m.p. °C. |
|---|---|---|---|---|---|
| CXCVI | H | H | — | β | 0.55 F |
| CXCVII | —CH₃ | —CH₃ | — | α/III | 191 |
| CXCVIII | H | —(CH₂)₃CH₃ | rac | III | 0.87 F |
| CXCIX | H | cyclohexyl | rac | III | 92 |

TABLE XIX-continued

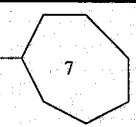

| Ex. No. | R¹ | R² | * | Preparation analogously to Example | $R_f$ (eluent)*/ m.p. °C. |
|---|---|---|---|---|---|
| CC | H | cycloheptyl (7-ring) | rac | III | 84 |
| CCI | H | –CH₂–C₆H₅ | rac | III | 0.73 F |
| CCII | H | –(CH₂)₄–CH₃ | rac | III | 0.83 F |
| CCIII | H | –(CH₂)₄–CH₃ | rac | III | 0.85 F |
| CCIV | H | –(CH₂)₂–CH(CH₃)₂ | rac | III | 0.76 F |

The compounds shown in Table XX are prepared in analogy to the present procedure of Example CLXXV:

TABLE XX

[Structure: 2-butyl-5-chloro-imidazole with N-CH₂-phenyl bearing CH(cyclopentyl)-CO-R² and R¹ at imidazole 4-position]

| Ex. No. | R¹ | R² | * | $R_f$ (eluent)* |
|---|---|---|---|---|
| CCV | –CHO | –NH–CH(C₆H₅)–CH₂–O–C(O)–CH₃ | dia | 0.76 H |
| CCVI | –CH₂OH | –NH–CH(C₆H₅)–CH₂–O–C(O)–CH₃ | dia | 0.49 H |

TABLE XXI

[Structure: imidazole with H3C-CH2-CH2-CH2- chain, Cl substituent, R1 group, N-CH2-phenyl-CH(cyclopentyl)-CO-R2]

| Ex. No. | R¹ | R² | $R_f$ (eluent) |
|---|---|---|---|
| CCVII | —CHO | 4-F-phenyl-CH(NH—)-CH2OH | 0.29 A |
| CCVIII | —CHO | 2-F-phenyl-CH(NH—)-CH2OH | 0.41 B |
| CCIX | —CH2OH | 4-F-phenyl-CH(NH—)-CH2OH | 0.46 C |
| CCX | —CH2OH | 4-F-phenyl-CH(NH—)-CH2OH | 0.31 C |
| CCXI | —CH2OH | 2-F-phenyl-CH(NH—)-CH2OH | 0.42 D |
| CCXII | —CH2OH | 2-F-phenyl-CH(NH—)-CH2OH | 0.32 D |

TABLE XXI-continued

| Ex. No. | R¹ | R² | $R_f$ | Isomer |
|---|---|---|---|---|
| CCXIII | CHO | —NH—CH(phenyl)-CH(OH)— | 0,39 A | 4 dia |
| CCXIV | CHO | phenyl-CH(N(CH3)—)-CH2OH | 0,69 A | 4 dia |
| CCXV | CH2OH | phenyl-CH(N(CH3)—)-CH2OH | 0,26 A | 4 dia |
| CCXVI | CH2OH | —NH—CH(phenyl)-CH(OH)— | 0,11 A | 4 dia |
| CCXVII | CHO | 3-F-phenyl-CH(NH—)-CH2OH | 0,22 C | 4 dia |
| CCXVIII | CH2OH | 3-F-phenyl-CH(NH—)-CH2OH | 0,25 D | dia A/rac |
| CCXIX | CH2OH | 3-F-phenyl-CH(NH—)-CH2OH | 0,16 D | dia B/rac |
| CCXX | CHO | 3-OH-phenyl-CH(NH—)-CH2OH | 0,41 D | 4 dia |

TABLE XXI-continued

| Ex. No. | | | Rf | * |
|---|---|---|---|---|
| CCXXI | CHO | (4-OH-phenyl)-CH(NH-)-CH2OH | 0,38 D | 4 dia |
| CCXXII | CH2OH | (3-OH-phenyl)-CH(NH-)-CH2OH | 0,26 J | dia A/rac |
| CCXXIII | CH2OH | (3-OH-phenyl)-CH(NH-)-CH2OH | 0,20 J | dia B/rac |
| CCXXIV | CH2OH | (4-OH-phenyl)-CH(NH-)-CH2OH | 0,27 J | dia A/rac |
| CCXXV | CH2OH | (4-OH-phenyl)-CH(NH-)-CH2OH | 0,19 J | dia B/rac |
| CCXXVI | CHO | (2-OH-phenyl)-CH(NH-)-CH2OH | 0,59 K | 4 dia |
| CCXXVII | CH2OH | (2,4-diOH-phenyl)-CH(NH-)-CH2OH | 0,20 D | dia A/rac |
| CCXXVIII | CH2OH | (2-OH-phenyl)-CH(NH-)-CH2OH | 0,13 D | dia B/rac |
| CCXXIX | CH2OH | (3,4-diOH-phenyl)-CH(NH-)-CH2OH | 0,42 A | 4 dia |

The compounds shown in Tables XXII to XXXI are prepared in analogy to the procedures indicated therein.

TABLE XXII

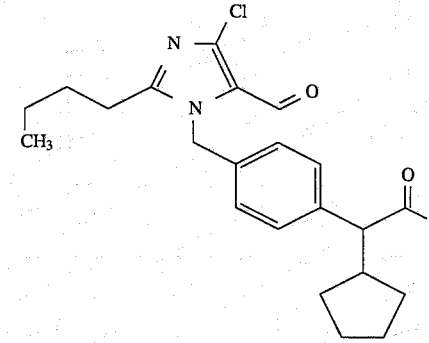

| Ex. No. | R | * | preparat. analogously to example | Rf (eluent) |
|---|---|---|---|---|
| CCXXX | (4-Cl-phenyl)-CH(NHrac)-CH2OH | dia (rac) | V | 0,62 (I) |
| CCXXXI | NH-CH2CH2-OH | (rac) | V | 0,48 (H) |

TABLE XXIII

Structure: imidazole with Cl, N=C-butyl, carboxylic acid, N-CH2-phenyl-CH(R1)-C(=O)-R2

| Ex. No. | R¹ | R² | * | preparat. analogously to Ex. | R_f (eluent) |
|---|---|---|---|---|---|
| CCXXXII | benzyl (CH2-C6H5) | NHSO2-C6H4-CH3 (p-tolyl) | rac | XCVI | 0,40 (G) |
| CCXXXIII | isobutyl (CH2-CH(CH3)2) | NHSO2-C6H4-CH3 (p-tolyl) | rac | XCVI | 0,48 (G) |

TABLE XXIV

Structure: imidazole with Cl, N=C-butyl, CH2OH, N-CH2-phenyl-C(R1)(R2)-COOH

| Ex. No. | R¹ | R² | * | Prep. analogously to Ex. | R_f (eluent) |
|---|---|---|---|---|---|
| CCXXXIV | H | isopropyl (CH(CH3)2) | rac | IV | 0,36 (F) |
| CCXXXV | H | n-propyl (CH2CH2CH3) | rac | IV | 0,18 (F) |
| CCXXXVI | H | cyclohexylmethyl | rac | IV | 0,36 (F) |
| CCXXXVII | cyclohexylmethyl | cyclohexylmethyl | — | IV | 0,46 (F) |
| CCXXXVIII | H | sec-butyl (CH(CH3)CH2CH3) | rac | IV | 0,39 (F) |

TABLE XXIV-continued
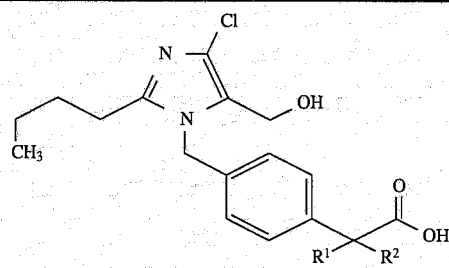
| Ex. No. | R¹ | R² | * | Prep. analogously to Ex. | $R_f$ (eluent) |
|---|---|---|---|---|---|
| CCXXXIX | OH | (cycloheptyl) | rac | 16/IV | 0,20 (F) |
TABLE XXV
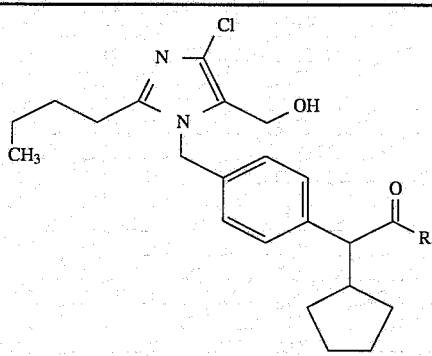
| Ex. No. | R | * | Prep. analogously to Exam. | $R_f$ (eluent) |
|---|---|---|---|---|
| CCXL | NH—CH₂CH₂—OH | rac | IV | 0,09 (I) |
| CCXLI | NH—CH₂CH₂—OAc | rac | CCIV | 0,42 (F) |
TABLE XXVI
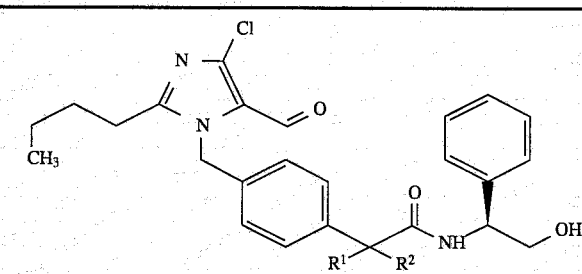
| Ex. No. | R¹ | R² | * | Prep. analogously to Ex. | $R_f$ (eluent) |
|---|---|---|---|---|---|
| CCXLII | H | H | S | 13/V | 0,54 (F) |

TABLE XXVI-continued

[Structure: 5-chloro-2-butyl-1-[4-(substituted)benzyl]-imidazole-4-carbaldehyde with N-(1-phenyl-2-hydroxyethyl)amide group, R¹ and R² on α-carbon]

| Ex. No. | R¹ | R² | * | Prep. analogously to Ex. | R_f (eluent) |
|---|---|---|---|---|---|
| CCXLIII | H | –CH₂–C₆H₅ (benzyl) | dia | V | 0,6 (F) |
| CCXLIV | H | –CH₂–cyclohexyl | dia | V | 0,51 (F) |
| CCXLV | H | (CH₃)₂CH–CH₂– (isobutyl) | dia | V | 0,73/0,77 (H) |
| CCXLVI | H | (CH₃)₂CH–CH₂–CH₂–CH₃ | dia | V | 0,61 (G) |
| CCXLVII | H | (CH₃)₂CH–CH₂–CH₃ | dia | V | 0,54 (F) |
| CCXLVIII | OH | cycloheptyl | dia | 16/V | 0,63 (P) |

TABLE XXVII

[Structure: 5-chloro-2-butyl-1-[4-(substituted)benzyl]-imidazole-4-carbaldehyde with α-substituted acetamide linked to N–SO₂–(4-methylphenyl)]

| Ex. No. | R¹ | R² | * | Prep. analogously to Ex. | R_f (eluent) |
|---|---|---|---|---|---|
| CCXLIX | H | (CH₃)₂CH–CH₂– | rac | III | 0,69 (K) |
| CCL | H | H₃C–CH₂–CH₂– | rac | III | 0,85 (F) |

TABLE XXVII-continued

[Structure: imidazole with Cl, CHO, N-butyl, N-CH2-C6H4-CR1R2-C(O)-NH-SO2-C6H4-CH3]

| Ex. No. | R¹ | R² | * | Prep. analogously to Ex. | $R_f$ (eluent) |
|---|---|---|---|---|---|
| CCLI | H | CH2-cyclohexyl | rac | III | 0,89 (F) |
| CCLII | H | CH(CH3)CH2CH2CH3 | rac | III | 0,72 (H) |

TABLE XXVIII

[Structure: imidazole with Cl, CH2OH, N-butyl, N-CH2-C6H4-CR1R2-C(O)-NH-CH(Ph)-CH2OH]

| Ex. No. | R¹ | R² | * | Prep. analogously to Ex. | $R_f$ (eluent) |
|---|---|---|---|---|---|
| CCLIII | H | CH(CH3)2 | dia | IV | 34 (H) |
| CCLIV | H | CH2CH2CH3 | dia | IV | 0,58 (F) |
| CCLV | H | CH(CH3)CH2CH3 | dia | IV | 0,54 (F) |
| CCLVI | H | CH(CH3)CH2CH2CH3 | dia | IV | 0,42 (F) |
| CCLVII | OH | cycloheptyl | dia | 16/IV | 0,28 (P) |
| CCLVIII | H | CH2-cyclohexyl | dia | IV | 0,44 (F) |

TABLE XXIX

| Ex. No. | R¹ | R² | * | Prep. analogously to Ex. | $R_f$ (eluent) |
|---|---|---|---|---|---|
| CCLIX | H | H₃C–CH(CH₃)– | rac | IV | 0,43 (F) |
| CCLX | H | CH₃CH(CH₃)CH₂CH₂CH₃ | rac | IV | 0,49 (F) |
| CCLXI | H | H₃C–CH₂CH₂CH₂– | rac | IV | 0,43 (F) |
| CCLXII | H | cyclohexyl-CH₂CH₂– | rac | IV | 0,48 (F) |
| CCLXIII | H | H₃C–CH(CH₃)CH₂CH₂CH₃ | rac | IV | 0,51 (H) |

TABLE XXX

| Ex. No. | R¹ | R² | $R_f$ (eluent) | Preparation analogously to Example |
|---|---|---|---|---|
| CCLXIV | H | —OH | 0,36 Q | XLV |
| CCLXV | C₂H₅ | NHSO₂–C₆H₄–CH₃ | 0,11 D | III |

EXAMPLE CCLXVI

2-[4-(2-Butyl-5-hydroxymethyl-4-pentafluoroethyl imidazol-1-yl-methyl)phenyl]-2-cyclopentyl-acetic acid N-4-tolylsulfonamide

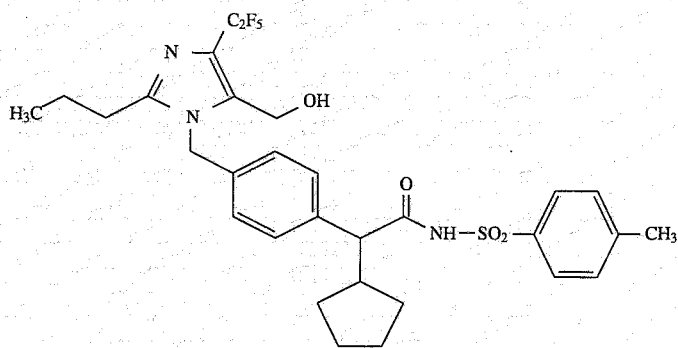

Example 4 (280 mg; 0,409 mmol) was left at room temperature for three days in methanol saturated with ammonia (60 ml). After evaporation the residue was distributed between 5%-aqueous sodium bicarbonate solution and ethylacetate. The aqueous phase was acidified to pH3 with aqueous potassiumhydrogensulfate-solution, then extracted with ethylacetate. Drying and evaporation of the organic phases yielded 255 mg of a resin [97% of theoretical yield; $R_f$=0,27 (C)].

TABLE XXXI

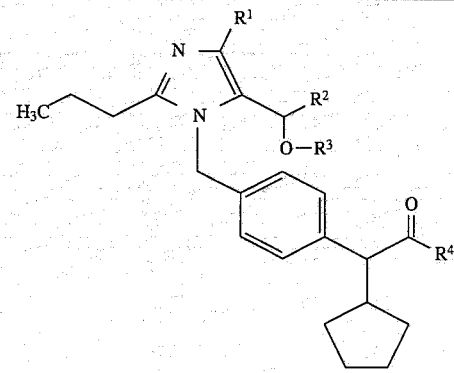

| Ex. No. | $R^1$ | $R^2$ | $R^3$ | $R^4$ | $R_f$ (eluent) | Preparation analogously to Example |
|---|---|---|---|---|---|---|
| CCLXVII | $-C_2F_5$ | H | Ac | OH | 0,46 A | CLXVIII |
| CCLXVIII | $-C_2F_5$ | H | H | OH | 0,58 C | CCLXVI |
| CCLXIX | $-C_2F_5$ | H | Ac | $-NH-Tos^*$ | 0,57 C | CXXVII |
| CCLXX | $-nC_4F_9$ | H | H | $-NH-Tos^*$ | 0,19 C | CCLXVI |
| CCLXXI | Cl | $-CH_2-C_6H_5$ | H | $-NH-Tos^*$ | 0,24 C | CXV |
| CCLXXII | Cl | $-CH_2CH_2CH_2CH_3$ | H | $-NH-TOs^*$ | 0,21 C | CXV |
| CCLXXIII | Cl | $-C_6H_5$ | H | $-NH-Tos^*$ | 0,20 C | CXV |

*Tos = 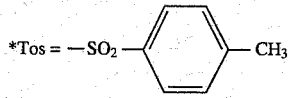

What we claim is:

1. A heterocyclically substituted phenylacetic acid derivative of the formula

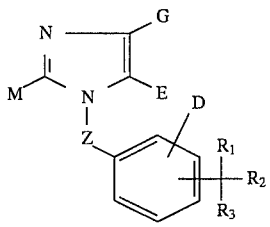

in which

M is straight-chain or branched alkyl having up to 6 carbon atoms;

G is halogen;

E is —CO—$R^5$ or straight-chain or branched alkyl having up to 6 carbon atoms which is substituted by $OR^{4''}$ wherein $R^5$ and $R^{4''}$ are both hydrogen Z is —$CH_2$—, —$(CH_2)_2$— or —$(CH_2)_3$—

D is hydrogen or methyl, $R^1$ and $R^2$ each identical or different represent hydrogen, hydroxyl, phenyl which is optionally substituted by fluorine, chlorine, $C_1$ to $C_4$ alkyl, $C_1$ to $C_4$ alkoxy, cyclopentyl or cycloheptyl, or $R^1$ represents hydrogen and $R^2$ represents cyclopentyl, cyclohexyl, cycloheptyl, cyclcoctyl which is optionally substituted by fluorine, chlorine, methyl, ethyl or methoxy, $R^3$ represents a group of the formula

—$CONR^{19}R^{20}$ in which $R^{19}$ is hydrogen and $R^{20}$ is a group of the formula

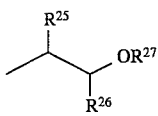

in which $R^{25}$ and $R^{26}$ are identical or different and denote hydrogen, phenyl or benzyl which is optionally mono- or disubstituted by fluorine, chlorine, or straight-chain or branched alkyl having up to 4 carbon atoms, $R^{27}$ is H or $C_1$ to $C_4$ alkyl, or a pharmaceutically acceptable salt thereof.

2. A compound according to claim 1, wherein $R^1$ represents hydrogen and $R^2$ represents cyclopentyl which is optionally substituted by fluorine, chlorine, methyl or ethyl, $R^{25}$ and $R^{26}$ are identical or different and denote hydrogen or phenyl, and $R^{27}$ is hydrogen or a pharmaceutically acceptable salt thereof.

3. A compound according to claim 1, which has the formula

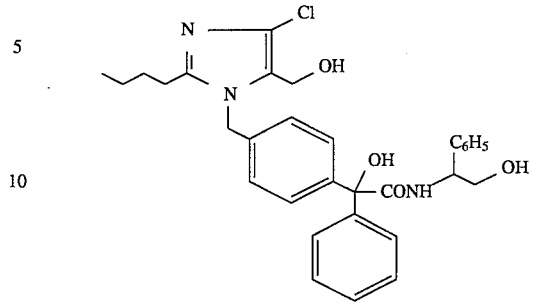

or a pharmaceutically acceptable salt thereof.

4. A compound according to claim 1, wherein such compound is 2-[4-(2-butyl-4-chloro-5-formyl-imidazol-1-yl-methyl)-phenyl]-2-cyclopentyl acetic acid 2-phenylglycinolamide of the formula

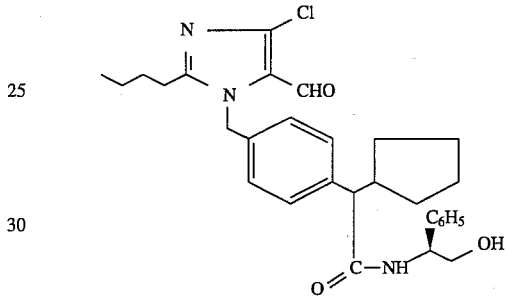

or a pharmaceutically acceptable salt thereof.

5. A compound according to claim 1, which has the formula

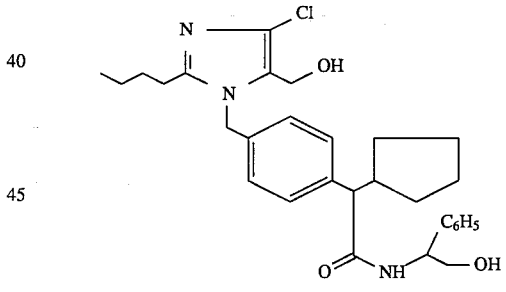

or a pharmaceutically acceptable salt thereof.

6. A composition for the treatment of arterial hypertension and atherosclerosis which comprises an effective amount of a compound or salt thereof according to claim 1 and a pharmaceutically acceptable diluent.

7. A method for treating arterial hypertension in a patient in need thereof which comprises administering to such patient an amount effective therefor of a compound or salt thereof according to claim 1.

* * * * *